(12) United States Patent
Zhou et al.

(10) Patent No.: US 8,426,191 B2
(45) Date of Patent: *Apr. 23, 2013

(54) MATERIALS AND METHODS FOR EFFICIENT LACTIC ACID PRODUCTION

(75) Inventors: Shengde Zhou, Dekalb, IL (US); Lonnie O'Neal Ingram, Gainesville, FL (US); Keelnatham T. Shanmugam, Gainesville, FL (US); Lorraine Yomano, Gainesville, FL (US); Tammy B. Grabar, Gainesville, FL (US); Jonathan C. Moore, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 657 days.

This patent is subject to a terminal disclaimer.

(21) Appl. No.: 12/632,041

(22) Filed: Dec. 7, 2009

(65) Prior Publication Data

US 2010/0203602 A1 Aug. 12, 2010

Related U.S. Application Data

(63) Continuation of application No. 11/501,137, filed on Aug. 8, 2006, now Pat. No. 7,629,162.

(60) Provisional application No. 60/706,887, filed on Aug. 10, 2005, provisional application No. 60/761,576, filed on Jan. 24, 2006, provisional application No. 60/799,619, filed on May 11, 2006.

(51) Int. Cl.
*C12N 1/21* (2006.01)
*C12P 7/56* (2006.01)

(52) U.S. Cl.
USPC ...... 435/252.33; 435/139; 435/170; 537/23.7

(58) Field of Classification Search .................. 435/139, 435/170, 252.33; 536/23.7
See application file for complete search history.

(56) References Cited

U.S. PATENT DOCUMENTS

| | | | |
|---|---|---|---|
| 5,821,093 A | 10/1998 | Ingram et al. | |
| 7,629,162 B2 * | 12/2009 | Zhou et al. | 435/252.33 |
| 2004/0152159 A1 | 8/2004 | Causey et al. | |
| 2009/0148914 A1 | 6/2009 | Causey et al. | |

OTHER PUBLICATIONS

Chang, D. -E. et al. "Homofermentative Production of D- or L-Lactate in Metabolically Engineered *Escherichia coli* RR1" *Applied and Environmental Microbiology*, Apr. 1999, pp. 1384-1389, vol. 65, No. 4.

Zhou, S. et al. "Production of Optically Pure D-Lactic Acid in Mineral Salts Medium by Metabolically Engineered *Escherichia coli* W3110" *Applied and Environmental Microbiology*, Jan. 2003, pp. 399-407, vol. 69, No.1.

Dien, B. S. et al. "Recombinant *Escherichia coil* engineered for production of L- lactic acid from hexose and pentose sugars" *Journal of Industrial Microbiology and Biotechnology*, 2001, pp. 259-264, vol. 27.

Zhou, S. et al. "Fermentation of 10% (w/v) sugar to D(-)-lactate by engineered *Escherichia coli* B" *Biotechnology Letters*, 2005, pp. 1891-1896, vol. 27.

Zhou, S. et al. "Fermentation of 12% (w/v) glucose to 1.2 M lactate by *Escherichia coli* strain SZ194 using mineral salts medium" *Biotechnology Letters*, 2006, pp. 663-670, vol. 28.

Grabar, T. B. et al. "Methylglyoxal bypass identified as source of chiral contamination in L(+) and D(-)-lactate fermentations by recombinant *Escherichia coli*" *Biotechnology Letters*, 2006, pp. 1527-1535, vol. 28.

Zhou, S. et al. "Betaine tripled the volumetric productivity of D(-)-lactate by *Escherichia coli* strain SZ132 in mineral salts medium" *Biotechnology Letters*, 2006, pp. 671-676, vol. 28.

Totemeyer, S. et al. "From famine to feast: the role of methylglyoxal production in *Escherichia coli*" *Molecular Microbiology*, 1998, pp. 553-562, vol. 27, No. 3.

Weber, J. et al. "Metabolic flux analysis of *Escherichia coli* in glucose-limited continuous culture. II. Dynamic response to famine and feast, activation of the methylgyloxal pathway and oscillatory behaviour" *Microbiology*, 2005, pp. 707-716, vol. 151, Pt. 3.

Zhu, M. M. et al. "Accumulation of Methylglyoxal in Anaerobically Grown *Escherichia coli* and Its Detoxification by Expression of the *Pseudomonas putida* Glyoxalase I Gene" *Metabolic Engineering*, 2001, pp. 218-225, vol. 3.

Shibata, T. et al. "Functional overlap between RecA and MgsA (RarA) in the rescue of stalled replication forks in *Escherichia coli*" *Genes to Cells*, Mar. 2005, pp. 181-191 and Supp. pp. 1-2, vol. 10, No. 3.

Zhou, S. et al. "Functional Replacement of the *Escherichia coli* D-(-)-Lactate Dehydrogenase Gene (*ldhA*) with the L-(+)-Lactate Dehydrogenase Gene (*ldhL*) from *Pediococcus acidilactici*" *Applied and Environmental Microbiology*, Apr. 2003, pp. 2237-2244, vol. 69, No. 4.

Jantama, K. et al. "Eliminating Side Products and Increasing Succinate Yields in Engineered Strains of *Escherichia coli* C" *Biotechnology and Bioengineering*, Dec. 1, 2008, pp. 881-892. vol. 101, No. 5.

Jantama, K. et al. "Combining Metabolic Engineering and Metabolic Evolution to Develop Nonrecombinant Strains of *Escherichia coli* C That Produce Succinate and Malate" *Biotechnology and Bioengineering*, Apr. 1, 2008, pp. 1140-1153, vol. 99, No. 5.

Yomano, L.P. et al. "Deletion of methylglyoxal synathase gene (*mgsA*) increased sugar co-metabolism in ethanol-producing *Escherichia coli*" *Biotechnology Letters*, 2009, pp. 1389-1398, vol. 31, No. 9.

(Continued)

*Primary Examiner* — Kevin Hill
(74) *Attorney, Agent, or Firm* — Saliwanchik, Lloyd & Eisenschenk

(57) ABSTRACT

The present invention provides derivatives of *Escherichia coli* constructed for the production of lactic acid. The transformed *E. coli* of the invention are prepared by deleting the genes that encode competing pathways followed by a growth-based selection for mutants with improved performance. These transformed *E. coli* are useful for providing an increased supply of lactic acid for use in food and industrial applications.

8 Claims, 19 Drawing Sheets

OTHER PUBLICATIONS

Zhang, X. et al. "Production of L-alanine by metabolically engineered *Escherichia coli*" *Applied Genetics and Molecular Biotechnology*, 2007, pp. 355-366, vol. 77, No. 2.

Zhou, S. et al. "Novel *Escherichia coli* Biocatalysts for the Efficient Production of (L+) and D(−)-Lactic Acids from Hexose and Pentose Sugars in Mineral Salts Medium" *Abstracts of the General Meeting of the American Society for Microbiology*, Jan. 1, 2003, p. 487, vol. 103, Abstract only.

Shukla et al., "Production of Lactic Acid from Sucrose by Metabolic Engineered *Escherichia coli*," Abstracts of the General Meeting of the American Society for Microbiology, 2003, p. 476, 0-052.

Misra et al., "Glyoxalase III from *Escherichia coli*: a single novel enzyme for the conversion of methylglyoxal into D-lactate without reduced glutathione," *Biochem. J.*, 1995, pp. 999-1003, vol. 305.

Moniruzzaman et al., "Isolation and Molecular Characterization of High-Performance Cellobiose-Fermenting Spontaneous Mutants of Ethanologenic *Escherichia coif* K011 Containing the *Klebsiella oxytoca* casAB Operon," *Applied and Environmental Microbiology*, Dec. 1997, pp. 4633-4637, vol. 63, No. 12.

Underwood et al., "Genetic Changes to Optimize Carbon Partitioning between Ethanol and Biosynthesis in Ethanologenic *Escherichia coli*," *Applied and Environmental Microbiology*, Dec. 2002, pp. 6263-6272, vol. 68, No. 12.

Zhou et al., "Gene Integration and Expression and Extracellular Secretion of *Erwinia chrysanthemi* Endoglucanase CeIY (*celY*) and CelZ (*celZ*) in Ethanologenic *Klebsiella oxytoca* P2," *Applied and Environmental Microbiology*, Jan. 2001, pp. 6-14, vol. 67, No. 1.

* cited by examiner

+ and − 1 mM betaine

+ and − 1 mM betaine, cleaner products, higher yields.

SZ186 is improved strain, cleaner products, higher yields.

Acclimation of SZ186 to mineral media, resulting strain SZ194 pH 7.5 and 8.0 are better than pH 6.5 and pH 6.0

Above 10% sugar, cultures take off slowly.

Fed batch helps improve rates, >1 M lactate in broth after 72-96 h.

MATERIALS AND METHODS FOR EFFICIENT LACTIC ACID PRODUCTION

CROSS-REFERENCE TO RELATED APPLICATIONS

This application is a continuation of U.S. patent application Ser. No. 11/501,137, filed Aug. 8, 2006, now U.S. Pat. No. 7,629,162, which claims the benefit of U.S. Provisional Application Ser. No. 60/706,887, filed Aug. 10, 2005; Ser. No. 60/761,576, filed Jan. 24, 2006; and Ser. No. 60/799,619, filed May 11, 2006. Each of these applications is hereby incorporated by reference in its entirety, including all figures and sequences.

GOVERNMENT SUPPORT

This invention was made with government support under a grant awarded from the Department of Energy under grant number USDOE-DE FG02-96ER20222 and Department of Energy in conjunction with the United States Department of Agriculture under grant number USDA & DOE Biomass RDI DE FG36-04GO14019. This invention was also made with government support from the U.S. Department of Agriculture under grant numbers 01-35504-10669 and 00-52104-9704. The government has certain rights in the invention.

BACKGROUND OF THE INVENTION

Lactic acid is commonly used as a food additive for preservation, flavor, and acidity. Lactic acid is also used in the manufacture of biodegradable plastic, namely polylactic acid (PLA). The use of PLA as a renewable alternative to petroleum-based products is rapidly expanding (Agrawal, 2003). Physical properties and rate of biological degradation of PLA can be controlled by manipulating the ratio of the chiral substrates, D-lactic acid and L-lactic acid (Narayanan et al., 2004). The global lactic acid market is estimated to be in excess of 100,000 tons per year and is expected to increase substantially in the next few years as new PLA facilities become operational.

For example, demand for the biodegradable solvent ethyl lactate (a derivative of lactic acid) is expected to increase substantially in the near future. It has been estimated that lactate esters could potentially replace as much as 80% of the 3.8 million tons of solvents used each year in the U.S. This solvent is non-toxic and has many useful applications, including in electronic manufacturing, in paints and coatings, in textiles, cleaners and degreasers, adhesives, printing, and de-inking.

Fermentative methods for production of lactic acid are often preferred over chemical synthesis, which results in a mixture of both D and L isomers. The products of microbiological fermentations are dependent on the organism used. Microbiological fermentation can yield a mixture of the two isomers or optically pure lactic acid in a stereospecific form. The desired stereospecificity of the product depends on the intended use.

Bacterial fermentations with Lactobacilli are common for industrial production of lactic acid, but these fermentations rarely yield optically pure product. Additionally, the fastidious nature of these bacteria requires that considerable amounts of supplemental nutrients be added to the growth medium, adding additional cost and making purification more difficult. Moreover, fermentation methods for producing lactic acid are highly inefficient and must be improved to ensure the economic feasibility of the aforementioned anticipated market expansions.

Yeast are not capable of producing appreciable levels of lactic acid, although recombinant *Saccharomyces cerevisiae* strains have been described that contain the ldh gene from either *Lactobacillus* or bovine origins (Patent WO 99/14335 and Adachi et al., 1998). While capable of producing up to 2-4% (w/v) lactic acid, these strains exhibit poor productivity and a significant portion of the glucose is converted to ethanol.

The filamentous fungus *Rhizopus oryzae* (syn. *R. arrhizus*) is also used for industrial production of lactic acid. *R. oryzae* is able to aerobically convert glucose, in a chemically defined medium, to large amounts of optically pure L-(+)-lactic acid. Research on lactic acid production by *Rhizopus* has continued primarily because of the ease of product purification in a minimal growth medium and the ability of the fungus to utilize both complex carbohydrates and pentose sugars (U.S. Pat. No. 4,963,486). This allows the fungus to be utilized for conversion of low value agricultural biomass to lactic acid. Unfortunately, the ability to modify lactic acid production by genetic modification in *Rhizopus* and other fungi has been limited.

*Escherichia coli* K-12-based biocatalysts have been engineered for D-(−)-lactate production but were unable to ferment 10% glucose or sucrose to completion in complex or minimal medium (Chang et al., 1999; Dien et al., 2001; Zhou et al., 2003; Zhu and Shimizu 2004).

One of the *E. coli* biocatalysts, SZ63 (pLOI3501), was developed for sucrose fermentation by functionally expressing the cscR' cscA' cscKB' genes from *E. coli* B on a plasmid (Shukla et al. 2004). Although capable of efficient fermentation of 5% glucose or sucrose, higher sugar concentrations were incompletely metabolized by this biocatalyst and continuous antibiotic selection was required for plasmid maintenance.

Other biocatalysts derived from *E. coli* strain B, such as KO11 (Deposit No. ATCC 55124), have the native ability to ferment sucrose (Moniruzzaman et al., 1997). As with the strain SZ63, higher sugar concentrations are incompletely metabolized by this biocatalyst and continuous antibiotic selection is required for plasmid maintenance.

Accordingly, a need still exists for improved lactic acid biocatalysts with increased fermentation rates, product titer, and yields to reduce costs associated with the bio-based production of commodity chemicals (Arntzen et al., 1999; Chotani et al., 2000; Datta et al., 1995; Hofvendahl and Hahn-Hagerdal, 2000; and Ohara et al., 2001).

BRIEF SUMMARY OF THE INVENTION

The subject invention provides novel microorganisms useful in the production of lactic acid. Additionally, the subject invention provides novel constructs for use in transforming any of numerous host organisms, preferably *Escherichia coli*, to express and/or suppress certain genes to produce lactic acid when the host organism is cultivated in a fermentable medium. Accordingly, the materials and methods of the subject invention can be used to enhance lactic acid production in host organisms thereby providing an increased supply of lactic acid for use in food and industrial applications.

In certain embodiments, derivatives of ethanologenic *Escherichia coli* (also referred to herein as *E. coli*) KO11 are constructed for the production of D-(−)-lactate. In other embodiments of the invention, E. coli are engineered in accordance with the subject invention for the production of L-(+)-lactate.

In accordance with the subject invention, novel E. coli KOH-based biocatalysts are prepared by deleting the genes that encode competing pathways followed by a growth-based selection for mutants with improved performance for fermenting glucose and/or sucrose.

The engineered microbes of the invention preferably contain native genes for sucrose utilization. Certain engineered E. coli strains of the invention can ferment 10% glucose or sucrose to produce over 1 mole D-(−)-lactate/1 of fermentation broth, with yields based on metabolized sugar ranging from about 88% to about 95%, depending on the fermentation broth. Other engineered E. coli strains of the invention can ferment glucose or sucrose to produce L-(+)-lactate.

Additional advantages of this invention will become readily apparent from the ensuing description.

BRIEF DESCRIPTION OF THE FIGURES

FIG. 6 illustrates the metabolic evolution of SZ132 for improved growth and lactate production in 10% sucrose (pH 7.0). Strain SZ132 was sequentially transferred in mineral salts medium containing 10% (w/v) sucrose to enrich for spontaneous mutants with improved growth and lactate production without betaine. One clone, SZ186, was isolated from the final transfer.

FIG. 7 illustrates the metabolic evolution of SZ186 for improved growth and lactate production in 10% glucose (pH 7.0). Strain SZ186 was sequentially transferred in mineral salts medium containing 10% (w/v) glucose and 1 mM betaine to enrich for spontaneous mutants with improved growth and lactate production. One clone, SZ194, was isolated from the final transfer.

FIG. 8 illustrates the comparison of lactate production by SZ194 in batch and fed-batch fermentations. Fermentations were carried out in mineral salts medium containing 1 mM betaine (pH 7.5).

FIG. 9A is the Dihydroxyacetone-P node. FIG. 9B is the Methylglyoxal Bypass. Abbreviations: DHAP, dihydroxyacetone phosphate; Gly3P, glyceraldehyde 3-phosphate.

FIG. 10A shows the organic acid production by D-(−)-lactate strains. FIG. 10B shows the growth of D-(−)-lactate strains. Symbols for FIGS. 10A and 10B: Δ, SZ194; ○, TG112 (10% w/v glucose); ◇, TG113; □, TG114. FIG. 10C shows the effect of mgsA deletion on organic acid production by L-(+)-lactate strains (10% glucose+1 mM betaine). FIG. 10D shows the effect of mgsA deletion on growth of L-(+)-lactate strains (10% glucose). Symbols for FIGS. 10C and 10D: ●, TG102 (mgsA$^+$, 10% w/v glucose, no betaine); ○, TG 103 (mgsA$^+$, 10% w/v glucose, no betaine); ■, TG105 (mgsA deleted, 1 mM betaine); *, TG103 (mgsA$^+$, 1 mM betaine). FIG. 10E shows the organic acid production by L-(+)-lactate strains. FIG. 10F shows the growth of L-(+)-lactate strains. Symbols for FIGS. 10E and 10F: ■, TG105; ■, TG106; ▲, TG107; ♦, TG108.

FIG. 11A shows the total organic acids (mM) calculated from base consumed to maintain pH 7. FIG. 11B shows cell Mass (g/L). Symbols: ▲, SZ194, 12% (w/v) glucose; ○, TG112, 10% (w/v) glucose, 1:100 dilution, 24 hour transfers; ●, TG112, 12% (w/v) glucose, 1:100 dilution, 24 hour transfers; □, TG113, 12% (w/v) glucose, 1:350 dilution, 24 hour transfers; and ♦, TG113, 12% (w/v) glucose, 1:100 dilution, 48 hour transfers.

BRIEF DESCRIPTION OF THE SEQUENCES

Figure 1:
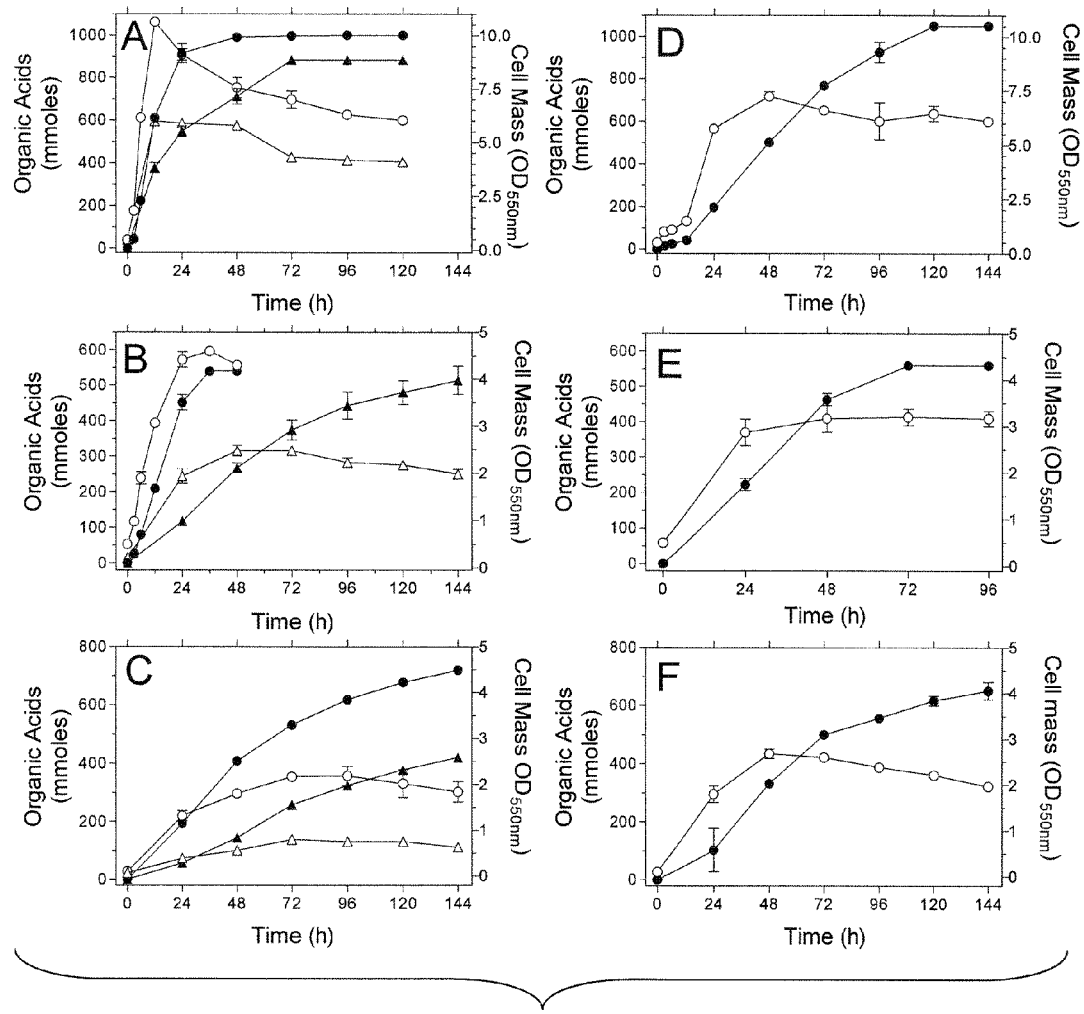
FIGS. 1A-1F graphically illustrate the difference in activity between an embodiment of the invention as compared to strain SZ63. Symbols for FIG. 1A: ●, SZ132 (lactate); ▲, SZ63 (lactate); ○, SZ132 (cell mass); Δ, SZ63 (cell mass). Symbols for FIG. 1B: ●, SZ132 (cell mass); ▲, SZ63 (cell mass); ○, SZ132 (lactate); Δ, SZ63 (lactate). Symbols for FIG. 1C: ●, SZ132 (lactate); ▲, SZ63 (lactate); ○, SZ132 (cell mass); Δ, SZ63 (cell mass). Symbols for FIG. 1D: ○, SZ63; ●, SZ132. Symbols for FIG. 1E: ○, 10% sucrose; ●, 5% sucrose. Symbols for FIG. 1F: ○, 10% sucrose; ●, 5% sucrose.
Figure 2A:
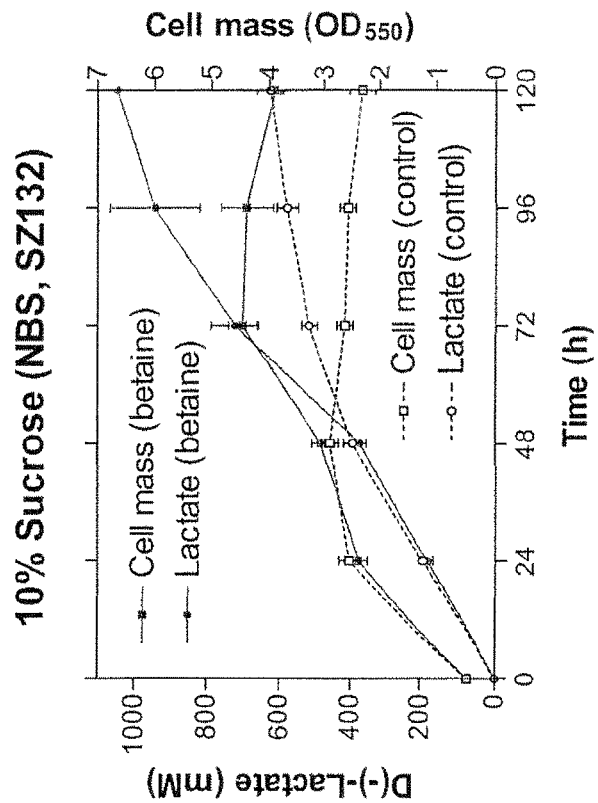
FIGS. 2A-2D illustrate progress of lactic acid production by various embodiments of the invention under fermentation conditions in NBS mineral salts medium.
Figure 2B:
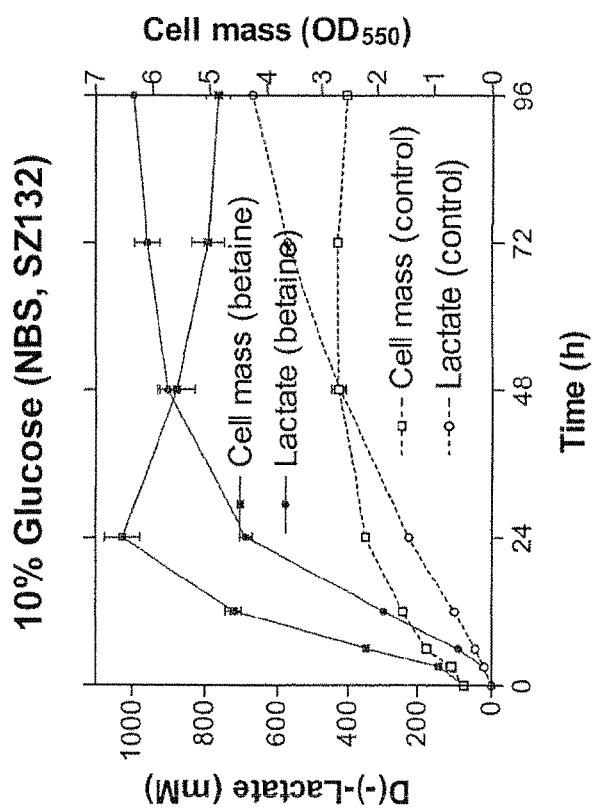
Figure 2D:
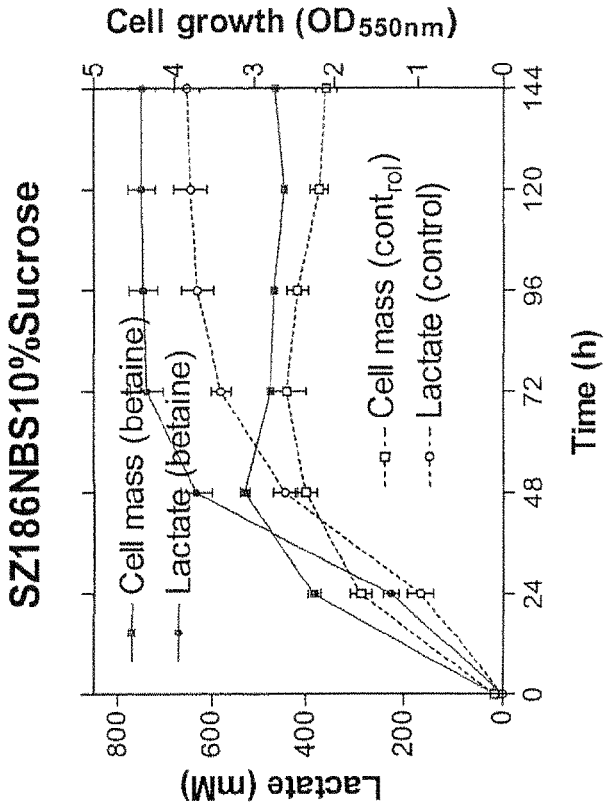
Figure 2C:
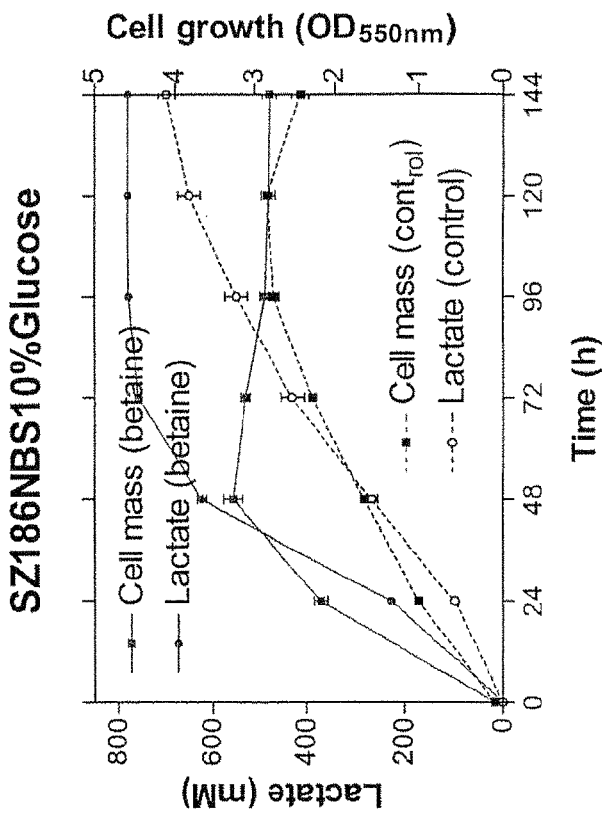

SEQ ID NO:1 is the nucleotide sequence for a sense primer for frdBC deletion.

SEQ ID NO:2 is the nucleotide sequence for an antisense primer for frdBC deletion.

SEQ ID NO:3 is the nucleotide sequence for a sense primer for adhE deletion.

SEQ ID NO:4 is the nucleotide sequence for an antisense primer for adhE deletion.

SEQ ID NO:5 is the nucleotide sequence for a sense primer for celY deletion.

SEQ ID NO:6 is the nucleotide sequence for an antisense primer for celY deletion.

SEQ ID NO:7 is the nucleotide sequence for a sense primer for mgsA deletion.

SEQ ID NO:8 is the nucleotide sequence for an antisense primer for mgsA deletion.

SEQ ID NO:9 is the nucleotide sequence for a sense primer for amplification of FRT-cat-sacB.

SEQ ID NO:10 is the nucleotide sequence for an antisense primer for amplification of FRT-cat-sacB.

SEQ ID NO:11 is the nucleotide sequence for a sense primer for amplification of cat-sacB with 5' NheI site.

SEQ ID NO:12 is the nucleotide sequence for an antisense primer for amplification of cat-sacB with 5' NheI site.

SEQ ID NO:13 is the nucleotide sequence for a sense primer for cloning frdABCD.

SEQ ID NO:14 is the nucleotide sequence for an antisense primer for cloning frdABCD.

SEQ ID NO:15 is the nucleotide sequence for a sense primer for cloning ackA.

SEQ ID NO:16 is the nucleotide sequence for an antisense primer for cloning ackA.

SEQ ID NO:17 is the nucleotide sequence for a sense primer for cloning lacZ-cynX SEQ ID NO:18 is the nucleotide sequence for an antisense primer for cloning lacZ-cynX.

SEQ ID NO:19 is the nucleotide sequence for a sense primer for cloning mgsA.

SEQ ID NO:20 is the nucleotide sequence for an antisense primer for cloning mgsA.

SEQ ID NO:21 is the nucleotide sequence for a sense primer for cloning focA-pflB.

SEQ ID NO:22 is the nucleotide sequence for an antisense primer for cloning focA-pflB.

SEQ ID NO:23 is the nucleotide sequence for a sense primer for cloning adhE.

SEQ ID NO:24 is the nucleotide sequence for an antisense primer for cloning adhE.

SEQ ID NO:25 is the nucleotide sequence for a sense primer for deleting frdBC.

SEQ ID NO:26 is the nucleotide sequence for an antisense primer for deleting frdBC.

SEQ ID NO:27 is the nucleotide sequence for a sense primer for deleting ackA.

SEQ ID NO:28 is the nucleotide sequence for an antisense primer for deleting ackA.

SEQ ID NO:29 is the nucleotide sequence for a lacZ antisense primer with 5' NheI site.

SEQ ID NO:30 is the nucleotide sequence for a cynX antisense primer with 5' NheI site.

SEQ ID NO:31 is the nucleotide sequence for a sense primer for deleting mgsA.

SEQ ID NO:32 is the nucleotide sequence for an antisense primer for deleting mgsA. SEQ ID NO:33 is the nucleotide sequence for a sense primer for deleting focA-pflB.

SEQ ID NO:34 is the nucleotide sequence for an antisense primer for deleting focA-pflB.

SEQ ID NO:35 is the nucleotide sequence for a sense primer for deleting adhE.

SEQ ID NO:36 is the nucleotide sequence for an antisense primer for deleting adhE.

SEQ ID NOs:37-46 depict the partial sequence of the genetic regions in which FRT scars were deleted. Partial sequences of the 5' and 3' region of the gene(s) are shown in bold, italics are used to designate the FRT scar and the underlined region was deleted in strain TG128.

DETAILED DESCRIPTION OF THE INVENTION

The present invention provides novel microorganisms that are capable of producing lactic acid when grown in a variety of fermentation conditions. The present invention also provides methods for engineering such microorganisms as well as methods for efficiently and stably producing lactic acid using the novel microbes of the invention, so that a high yield of lactic acid is provided from relatively inexpensive raw products such as glucose or sucrose.

The term "lactic acid" in this application refers to 2-hydroxypropionic acid in either the free acid or salt form. The salt form of lactic acid is referred to as "lactate" regardless of the neutralizing agent, i.e., calcium carbonate or ammonium hydroxide. As referred to herein, lactic acid can refer to either stereoisomeric form of lactic acid (L-(+)-lactic acid or D-(−)-lactic acid). The term lactate can refer to either stereoisomeric form of lactate (L-(+)-lactate or D-(−)-lactate). The present invention provides microbes that produce a single stereoisomer of lactic acid or lactate. The lactic acid stereoisomer or lactate stereoisomer that is produced in accordance with some aspects of this invention is "chirally pure". The phrase "chirally pure" indicates that there is no detectable contamination of one stereoisomeric form of lactic acid or lactate with the other stereoisomeric form (the chiral purity of the specified stereoisomer is at least, greater than (or greater than or equal to) 99.9%). Genetically modified microorganisms disclosed herein that have had the methylglyoxal pathway (mgsA) deleted or inactivated are able to produce "chirally pure" D-(−)-lactic acid or L-(+)-lactic acid.

For certain embodiments of the invention, L-(+)-lactic acid is produced using the engineered microbes of the invention. In other embodiments of the invention, D-(−)-lactic acid is produced using the engineered microbes of the invention.

In one embodiment, the invention uses *Escherichia coli* (or *E. coli*) as a biocatalyst for the enhanced conversion of glucose and/or sucrose to lactic acid. In accordance with the present invention, the metabolism of a microorganism can be modified by introducing and expressing various genes. In accordance with the subject invention, various novel plasmids can be introduced into *E. coli* so that the transformed microorganism can produce large quantities of lactic acid in various fermentation conditions. The recombinant *E. coli* of the invention are preferably modified so that lactic acid is stably produced with high yield when grown on a medium comprising glucose and/or sucrose.

*E. coli* hosts containing the plasmids of the subject invention were deposited with the Agricultural Research Service Culture Collection, 1815 N. University Street, Peoria, Ill., 61604 U.S.A. The accession numbers and deposit dates are as follows:

| Culture | Accession number | Deposit date |
| --- | --- | --- |
| SZ132 | NRRL B-30861 | Aug. 3, 2005 |
| SZ186 | NRRL B-30862 | Aug. 3, 2005 |
| SZ194 | NRRL B-30863 | Aug. 3, 2005 |
| TG103 | NRRL B-30864 | Aug. 9, 2005 |
| TG102 | NRRL B-30921 | May 5, 2006 |
| TG105 | NRRL B-30922 | May 5, 2006 |
| TG106 | NRRL B-30923 | May 5, 2006 |
| TG107 | NRRL B-30924 | May 5, 2006 |
| TG108 | NRRL B-30925 | May 5, 2006 |
| TG112 | NRRL B-30926 | May 5, 2006 |
| TG113 | NRRL B-30927 | May 5, 2006 |
| TG114 | NRRL B-30928 | May 5, 2006 |
| TG128 | NRRL B-30962 | Jul. 25, 2006 |
| TG129 | NRRL B-30963 | Jul. 25, 2006 |
| TG130 | NRRL B-30964 | Jul. 25, 2006 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

One embodiment of the present invention provides an *E. coli* B strain ("SZ132"; Deposit No. NRRL B-30861) that is engineered to enhance cell growth and lactate production in various media. In one embodiment, the SZ132 strain can be constructed to produce D-lactate (lactic acid) via the following steps:

(a) constructing strain LY52 from *E. coli* K011 by integrating the *Klebsiella oxytoca* (Deposit No. ATCC 68564) casAB genes for cellobiose utilization behind the stop codon of lacY and integrating the *Erwinia chysanthem* (Deposit No. ATCC 55124) celY gene encoding endoglucanase into the frdA gene (Ohta et al., 1991; Moniruzzaman et al., 1997; Zhou and Ingram, 1999);

(b) sequentially transducing into LY52 certain mutations in *E. coli* K-12 (strain W3110), which were used to construct the strain SZ63 (Zhou et al., 2003);

(c) eliminating *Z. mobilis* genes for ethanol production by P1 transduction of the ΔfocA-pflB deletion from strain SZ31 (strain W3110);

(d) inactivating native *E. coli* alcohol dehydrogenase production by P1 transduction of the adhE mutation from strain TC20 (Zhou et al., 2003);

(e) deleting acetate kinase (ackA) using the mutation from strain SZ61 (strain W3110) (Zhou et al., 2003);

(f) removing antibiotic genes, which were used for selection, by FLP recombinase (Zhou et al., 2003); and (g) during removal of antibiotic genes of step (f), deleting an internal segment of casAB (or deleting an internal segment of the casAB gene after the step of removing antibiotic genes).

Related embodiments of the invention further involve transforming strain SZ132 to remove all foreign genes. In one embodiment, the *Klebsiella oxytoca* casAB and *Erwinia chrysanthemi* celY genes were deleted from strain SZ132 by homologous recombination using linear DNA; then FLP recombinase was used to eliminate antibiotic genes used during construction of strain SZ132. The resulting strain, SZ186 (Deposit No. NRRL B-30862), contains only native *E. coli* genes.

Another embodiment of the present invention provides an *E. coli* B strain ("TG103") that is engineered to enhance cell growth and the production of the L isomer of lactic acid in various media. In one embodiment, the TG103 strain can be constructed via the following steps:

(a) engineering strain SZ186 using methods as described herein;

(b) subjecting strain SZ186 to serial cultivation to select for increased growth and/or increased lactic acid production, wherein the selected strains are strain SZ194;

(c) integrating a heterologous L-lactic acid gene and kanamycin marker into the native ldhA (D-lactate dehydrogenase) gene of SZ194 and deleting the central part of the coding region to produce TG101;

(d) removing antibiotic genes by FLP recombinase to produce TG102; and (e) subjecting strain TG102 to serial transfer for several days (such as from about 7 to 21 days, preferably for 13 days), with 1:100 dilution of broth from previously inoculated culture each day and selecting strains that demonstrate improved growth and/or increased L-lactic acid production, wherein the selected strains are TG103.

According to certain embodiments of the subject invention, increased growth and increased lactic acid production are linked. The co-selection process for strains with improved growth and lactic acid production is referred to as "Metabolic Evolution." Certain embodiments of the invention also provide for the inactivation or deletion of certain genes within the genetically modified organisms provided by this application. In one aspect of the invention, the genes are deleted in order to inactivate the desired activity. Deletions provide maximum stability because there is no opportunity for a reverse mutation to restore function. Alternatively, genes can be inactivated by insertion of nucleic acid sequences that disrupt the function and/or expression of the gene (e.g., P1 transduction or other methods known in the art). The inactivation or deletion of one or more particular polynucleotide sequence as discussed herein can also be referred to as genetic "modifications."

The vector used for introducing specific genes into a host microorganism may be any vector so long as it can replicate in the host microorganism. Vectors of the present invention can be operable as cloning vectors or expression vectors in the selected host cell. Numerous vectors are known to practitioners skilled in the art, and selection of an appropriate vector and host cell is a matter of choice. The vectors may, for example, be bacteriophage, plasmids, viruses, or hybrids thereof, such as those described in Maniatis et al., 1989; Ausubel et al., 1995; Miller, J. H., 1992; Sambrook and Russell, 2001. Further, the vectors of the invention may be non-fusion vectors or fusion vectors.

Within each specific vector, various sites may be selected for insertion of a nucleotide sequence of interest. These sites are usually designated by the restriction enzyme or endonuclease that cuts them. The vector can be digested with a restriction enzyme matching the terminal sequence of the gene and the sequences can be ligated. The ligation is usually attained by using a ligase such as T4 DNA ligase.

The particular site chosen for insertion of the selected nucleotide fragment into the vector to form a recombinant vector is determined by a variety of factors. These include size and structure of the polypeptide to be expressed, susceptibility of the desired polypeptide to enzymatic degradation by the host cell components and contamination by its proteins, expression characteristics such as the location of start and stop codons, and other factors recognized by those of skill in the art. None of these factors alone absolutely controls the choice of insertion site for a particular polypeptide. Rather, the site chosen reflects a balance of these factors, and not all sites may be equally effective for a given protein.

A variety of vector-host cell expression systems may be employed in practicing the present invention. Strains of bacteria, such as *E. coli*, are particularly useful in producing lactic acid in the practice of the invention. However, the novel invention described here can be applied with numerous hosts that would be desirable for various lactic acid producing schemes. Host strains may be of bacterial, fungal, or yeast origin. Factors that can be considered in choosing host strains include substrate range, hardiness, sugar tolerance, salt tolerance, temperature tolerance, pH tolerance, and lactate tolerance. Ascertaining the most appropriate host-vector system is within the skill of the person in the art.

Methods for chromosomal deletions, integration, and removable antibiotic resistance genes have been previously described (Causey et al., 2004; Datsenko and Wanner, 2000; Martinez-Morales et al., 1999; Zhou et al., 2003). Any one or combination of such known methods may be employed in practicing the present invention.

As the promoter for the expression of the gene(s) to be presented in the host microorganism (for example, *K. oxytoca* casAB or *E. chrysanthemi* celY genes), when a promoter specific for the gene functions in host cells, this promoter can be used. Alternatively, it is also possible to ligate a foreign promoter to a DNA encoding the gene so as to obtain the expression under the control of the promoter. As such a promoter, when an *Escherichia* bacterium is used as the host, lac promoter, trp promoter, trc promoter, tac promoter, $P_R$ promoter and $P_L$ promoter of lambda phage, tet promoter, amyE promoter, spac promoter and so forth can be used. Further, it is also possible to use an expression vector containing a promoter like pUC19, and insert a DNA fragment, encoding for example *K. oxytoca* casAB, into the vector so that the fragment can be expressed under the control of the promoter.

Methods for preparation of chromosome DNA, PCR, preparation of plasmid DNA, digestion and ligation of DNA, transformation, design and synthesis of oligonucleotides used as primers and so forth may be usual ones well known to those skilled in the art. Such methods are described in, for example, Sambrook, J. et al. (1989) and so forth.

Lactic acid can be produced by allowing a transformed microorganism, as described above, to convert glucose and/or sucrose into lactic acid, and collecting the produced lactic acid. In one aspect of the invention, lactic acid can be produced at levels of greater than 0.5M when transformed organisms are cultured in a mineral salts medium, such as NBS mineral salts medium.

The vectors of the invention may be replicated autonomously or integrated into the genome of the host. Integration typically occurs by homologous recombination (for example, arginine selectable marker integrating in the chromosomal arginine gene) or at a chromosomal site unrelated to any genes on the vector. Integration may occur by either a single or double cross-over event. It is also possible to have any number of these integration and replication types occurring in the same constructed microorganism.

In certain embodiments, cultivation of the engineered microorganisms of the invention is carried out under aerobic condition for about 0.5 to 240 hours. The cultivation temperature is preferably controlled at about 25° C. to 45° C., and pH is preferably controlled at 5-8 during cultivation. Inorganic or organic, acidic, or alkaline substances as well as ammonia gas or the like can be used for pH adjustment.

The microorganism of the present invention can be obtained by transforming a bacterium belonging to *Escherichia* to express certain enzymes useful in the production of lactic acid. In a preferred embodiment, a bacterium belonging to *Escherichia* that can be used in the present invention is *Escherichia coli*.

In other embodiments of the invention, bacterium that can be used in the present invention include, but are not limited to, *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus* sp. CCM825, *Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Escherichia freundii, Microbacterium ammoniaphilum, Serratia marcescens, Salmonella typhimurium, Salmonella schottmulleri, Xanthomonas citri* and so forth.

Lactic acid can be produced in a reaction mixture by contacting a culture containing transformed microorganisms prepared in accordance with the present invention with sucrose and/or glucose. In other embodiments of the invention, cells are separated and collected from a culture of transformed microorganisms; processed transformed microorganism cells subjected to acetone treatment or lyophillization; a cell free extract prepared from such transformed microorganism cells or processed cells; fractions such as membrane fractions fractioned from such cell free extract; or immobilized materials can be produced by immobilizing transformed microorganism cells, processed cells, cell free extract and fractions, any of which independently or combined contacted with sucrose and/or glucose to produce lactic acid. The microorganism can consist of one kind of microorganism, or can be used as an arbitrary mixture of two or more kinds of microorganisms.

Fermentation parameters are dependent on the type of host organism used for production of the recombinant enzyme. Growth medium may be minimal/defined or complete/complex. Fermentable carbon sources could include hexose and pentose sugars, starch, cellulose, xylan, oligosaccharides, and combinations thereof. One form of growth media that can be used in accordance with the subject invention includes modified Luria-Bertani (LB) broth (with 10 g Difco tryptone, 5 g Difco yeast extract, and 5 g sodium chloride per liter) as described by Miller J. H. (1992). In other embodiments of the invention, cultures of constructed strains of the invention can be grown in NBS mineral salts medium (as described by Causey et al., 2004) and supplemented with 2% to 20% sugar (w/v) or either 5% or 10% sugar (glucose or sucrose). The microorganisms can be grown in or on NBS mineral salts medium. NBS mineral salts medium comprises, consists essentially of, or consists of the following components (per liter): 3.5 g of $KH_2PO_4$; 5.0 g of $K_2HPO_4$; 3.5 g of $(NH_4)_2HPO_4$; 0.25 g of $MgSO_4.7H_2O$; 15 mg $CaCl_2.2H_2O$; 0.5 mg of thiamine; and 1 ml of trace metal stock, glucose (e.g., 2% in plates or 3% in broth), and 1.5% agar (for plates). The trace metal stock is prepared in prepared in 0.1 M HCl and comprises, consists essentially of or consists of (per liter): 1.6 g of $FeCl_3$; 0.2 g of $CoCl_2.6H_2O$; 0.1 g of $CuCl_2$; 0.2 g of $ZnCl_2.4H2O$; 0.2 g of $NaMoO_4$; 0.05 g of $H_3BO_3$.4-Morpholinopropanesulfonic acid (0.1 M, pH 7.1) can be added to both liquid and solid media (filter-sterilized) when needed for pH control (and is optionally included in medium used for 10-liter fermentations). Minimal medium can also be prepared by using succinate (1 g·liter$^{-1}$) as a sole source of carbon (nonfermentable substrate) and can be added as a supplement to glucose-minimal medium when needed. In certain embodiments, antibiotics can be included as needed for strain construction.

Growth and production of the lactate can be performed in normal batch fermentations, fed-batch fermentations or continuous fermentations. In certain embodiments, it is desirable to perform fermentations under reduced oxygen or anaerobic conditions for certain hosts. In other embodiments, lactate production can be performed with oxygen; and, optionally with the use of air-lift or equivalent fermentors.

The pH of the fermentation should be sufficiently high enough to allow growth and lactate production by the host. Adjusting the pH of the fermentation broth may be performed using neutralizing agents such as calcium carbonate or hydroxides. Alternatively, lactic acid can be removed continuously during the fermentation using methods such as membrane technology, electro-dialysis, solvent extraction, and absorbent resins. The selection and incorporation of any of the above fermentative methods is highly dependent on the host strain and the preferred downstream process.

Various non-limiting embodiments of the subject invention include:

1. A genetically modified *E. coli* strain that comprises the following genetic modifications to *E. coli* strain K011 (ATCC 55124): a) insertion of the *Klebsiella oxytoca* casAB gene behind the stop codon of lacY; b) integration of the *Erwinia chrysanthemi* celY gene into the frdA gene; c) inactivation or deletion of focA-Z. *mobilis* pdc-adhB-pflB; d) inactivation or deletion of the native *E. coli* alcohol dehydrogenase gene; and e) inactivation or deletion of the acetate kinase (ackA) gene;

2. The genetically modified *E. coli* strain according to embodiment 1, wherein said genetically modified *E. coli* strain further comprises inactivated or deleted antibiotic resistance genes;

3. The genetically modified *E. coli* strain according to embodiment 1, wherein the *Klebsiella oxytoca* casAB gene and the *Erwinia chrysanthemi* celY gene are inactivated or deleted in said genetically modified *E. coli* strain after insertion;

4. The genetically modified *E. coli* strain according to embodiment 2, wherein the *Klebsiella oxytoca* casAB gene and the *Erwinia chrysanthemi* celY gene are inactivated or deleted in said genetically modified *E. coli* strain after insertion;

5. The genetically modified *E. coli* strain according to embodiment 2, wherein said genetically modified *E. coli* strain is metabolically evolved;

6. The genetically modified *E. coli* strain according to embodiment 1 or embodiment 3, wherein said genetically modified *E. coli* strain is metabolically evolved;

7. The genetically modified *E. coli* strain according to embodiment 4, wherein said genetically modified *E. coli* strain is metabolically evolved;

8. The genetically modified *E. coli* strain according to embodiments 1, 2, 3, 4, 5, 6, or 7, wherein the antibiotic genes are deleted with FLP recombinase;

9. The genetically modified *E. coli* strain according to embodiment 7, wherein said genetically modified *E. coli* strain is SZ186;

10. The genetically modified *E. coli* strain according to embodiment 5, wherein said genetically modified *E. coli* strain is SZ132;

11. The genetically modified *E. coli* strain according to embodiment 1, 2, 3, 4 or 5, wherein the mgsA gene of said strain is inactivated or deleted in said genetically modified *E. coli* strain;

12. A genetically modified *E. coli* strain comprising *E. coli* strain SZ194 (NRRL B30863) in which the mgsA gene has been inactivated or deleted;

13. The genetically modified *E. coli* strain according to embodiment 12, wherein said genetically modified *E. coli* strain is metabolically evolved;

14. The genetically modified *E. coli* strain according to embodiment 13, wherein said genetically modified *E. coli* strain is TG112, TG113 or TG114;

15. The genetically modified *E. coli* strain according to embodiment 11 or 12, wherein said genetically modified *E. coli* strain further comprises an inactivated or deleted native ldhA gene and a recombinantly inserted heterologous gene encoding an L-specific lactate dehydrogenase;

16. The genetically modified *E. coli* strain according to embodiment 15, wherein said heterologous L-specific lactate dehydrogenase gene is a ldhL gene (for example, a ldhL gene obtained from *P. acidilactici*);

17. The genetically modified *E. coli* strain according to embodiment 15 or embodiment 16, wherein said strain is metabolically evolved;

18. A genetically modified *E. coli* strain selected from TG112, TG113 or TG114, SZ194, SZ132, SZ186, or TG103;

19. A method of culturing or growing a genetically modified *E. coli* strain comprising inoculating a culture medium with one or more genetically modified *E. coli* strain according to any one of embodiments 1, 2, 3, 4, 5, 6, 7, 8, 9, 10, 11, 12, 13, 14, 15, 16, 17 or 18 and culturing or growing said a genetically modified *E. coli* strain;

20. A method of producing D-(−)-lactate or D-(−)-lactic acid comprising culturing one or more genetically modified *E. coli* strain according to any one of embodiments 1, 2, 3, 4, 5, 6, 7, 8, 9, 10, 11, 12, 13, or 14 under conditions that allow for the production of D-(−)-lactic acid and optionally neutralizing the D-(−)-lactic acid to form D-(−)-lactate;

21. The method according to embodiment 20, wherein said one or more genetically modified *E. coli* strain is selected from TG112, TG113, TG114 or SZ194;

22. A method of producing L-(+)-lactate or L-(+)-lactic acid comprising culturing one or more genetically modified E. coli strain according to any one of embodiments 15, 16 or 17 under conditions that allow for the production of L-(+)-lactic acid and optionally neutralizing the L-(+)-lactic acid to form L-(+)-lactate;

23. The method according to embodiment 22, wherein said one or more genetically modified E. coli strain is TG103, TG105, TG106, TG107, or TG108;

24. The method according to any one of embodiments 19, 20, 21, 22, or 23, wherein said genetically modified E. coli strain is cultured in a mineral salts medium;

25. The method according to embodiment 24, wherein the mineral salts medium comprises between 2% and 20% (w/v) of a sugar;

26. The method according to embodiment 25, wherein the mineral salts medium contains 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5% or 20% (w/v) of a sugar;

27. The method according to embodiment 25 or 26, wherein the sugar is glucose or sucrose or a combination of glucose and sucrose;

28. The method according to embodiment 20, wherein a genetically modified E. coli strain as set forth in embodiment 11 is cultured under conditions that allow for the production of chirally pure D-(−)-lactate or D-(−)-lactic acid;

29. The method according to embodiment 22, wherein a genetically modified E. coli strain as set forth in embodiment 15, 16 or 17 is cultured under conditions that allow for the production of chirally pure L-(+)-lactate or L-(+)-lactic acid;

30. The method according to embodiment 21, wherein said method produces chirally pure D-(−)-lactate or D-(−)-lactic acid;

31. The method according to embodiment 23, wherein said method produces chirally pure L-(+)-lactate or L-(+)-lactic acid;

32. The method according to embodiment 28, 29, 30 or 31, further comprising the step of purifying the chirally pure lactate (L-(+)-lactate or D-(−)-lactate);

33. The method according to any one of embodiments 20, 21, 22, 23, 24, 25, 26, 27, 28, 29, 30, 31 or 32, wherein lactate (e.g., the L-(+)-lactate or D-(−)-lactate) is produced at concentrations of at least 0.5M;

34. The method according to embodiment 33, wherein the culture medium is a chemically defined mineral salts medium such as NBS mineral salts medium;

35. The method according to embodiment 20, 21, 22, 23, 24, 25, 26, 27, 28, 29, 30, 31, 32, 33 or 34, wherein the yield of lactic acid (L-(+)-lactic acid or D-(−)-lactic acid) is at least or greater than (or greater than or equal to) 90%;

36. The method according to embodiment 35, wherein the yield is at least 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, or 99%;

37. The method according to embodiment 29, 30, 31, 32, 33, 34, 35 or 36, wherein there is no detectable contamination of one stereoisomeric form of lactic acid or lactate with the other stereoisomeric form (e.g., the chiral purity of the specified stereoisomer is at least, greater than (or greater than or equal to) 99.9%); or 38. A composition comprising one or more genetically modified E. coli strain according to any one of embodiments 1, 2, 3, 4, 5, 6, 7, 8, 9, 10, 11, 12, 13, 14, 15, 16, 17 or 18 and medium.

Following are examples that illustrate procedures for practicing the invention. These examples should not be construed as limiting. All percentages are by weight and all solvent mixture proportions are by volume unless otherwise noted.

EXAMPLE 1

Preparation and Analysis of E. Coli Strains SZ132 and SZ186

E. coli strains used in this Example are listed in Table 1. Strain SZ63 is a derivative of E. coli K-12 (ATCC 27325). KO11 (ATCC 55124) is a derivative of E. coli B (ATCC 11303) that contains the Zymomonas mobilis ethanol production genes integrated into the pflB gene.

TABLE 1

E. coli strains

| Strains | Relevant Characteristics | Sources |
|---------|--------------------------|---------|
| DH5α | ΔlacZ M15 recA | Invitrogen |
| S17-1 | thi pro recA hsdR RP4-2-tet::Mu aphA::Tn7 λpir | Simon et al. 1983 |
| TC20 | ΔadhE::FRT-tet-FRT | Zhou et al. 2003 |
| SZ31 | W3110, Δ(focA-pflB)::FRT-kan-FRT | Zhou et al. 2003 |
| SZ61 | W3110, ΔackA::FRT-tet-FRT | Zhou et al. 2003 |
| SZ63 | W3110, ΔfocA-pflB::FRT Δfrd ΔadhE::FRT ΔackA::FRT | Zhou et al. 2003 |
| NC3 | E. coli B/r, hsdR | Dien et al. 2001 |
| KO11 | pflB::Z. mobilis pdc adhB cat, Δfrd | Ohta et al. 1991 |
| LY52 | KO11, frdA::K. oxytoca casAB, lacY:: E. chrysanthemi celY | This example |
| SZ132 | LY52, Δ(focA-pdc-adhB-pflB) ΔadhE::FRT ΔackA::FRT, ΔcasA | This example |
| SZ186 | SZ132, ΔK. oxytoca casAB ΔE. chrysanthemi celY | This example |

Cultures were grown at 37° C. in modified Luria-Bertani (LB) broth (per liter: 10 g Difco tryptone, 5 g Difco yeast extract, 5 g sodium chloride) or in NBS mineral salts medium supplemented with either 5% or 10% sugar (glucose or sucrose). Antibiotics were included as needed for strain constructions.

Standard methods were used for plasmid construction. Methods for chromosomal deletions, integration, and removable antibiotic resistance genes have been previously described. Strains E. coli DH5α and S17-1 were used as hosts for plasmid construction. Strain NC3 was used as an intermediate host to minimize problems associated with restriction enzymes during P1 transduction from K-12 strains to B strains (Dien et al., 2001).

Seed cultures were prepared as described previously by Shukla et al. (2004) and Zhou et al., (2003) and used to inoculate small fermentation vessels (350 ml working volume, 35° C., 150 rpm agitation). Broth was maintained at pH 7.0 by the automatic addition of 6 N KOH. Plotted data represent an average of 2 or more replicates. Bars denoting the standard error of the mean are included for averages of 3 or more fermentations. Maximum volumetric productivity for lactate was estimated from the steepest region of each graph. No antibiotics were included during the growth of seed cultures or in fermentation broths.

Cell mass was estimated by measuring optical density at 550 nm (330 mg dry cell wt/l at 1.0 OD$_{550nm}$) Total organic acid production (primarily lactate) was measured by base (KOH) consumption. Acidic products were analyzed at the end of fermentation by high-performance liquid chromatography. Ethanol was measured by gas chromatography.

Construction of Strain SZ132

Strain LY52 was constructed from KO11 by integrating the *Klebsiella oxytoca* casAB genes (Moniruzzaman et al. 1997) for cellobiose utilization behind the stop codon of lacY and integrating the *Erwinia chrysanthemi* celY gene encoding endoglucanase (Zhou and Ingram, 1999) into the frdA gene. Previously characterized mutations in *E. coli* K-12 (strain W3110) used to construct SZ63 (Zhou et al., 2003) for lactate production were sequentially transduced into LY52. *Z. mobilis* genes for ethanol production were eliminated by P1 transduction of the ΔfocA-pflB deletion from SZ31. The native *E. coli* alcohol dehydrogenase was inactivated by P1 transduction of the adhE mutation from TC20. Acetate kinase (ackA) was deleted using the mutation in SZ61. Antibiotic genes used for selection were removed by FLP recombinase (Zhou et al., 2003). During the removal of antibiotic genes with FLP recombinase, an internal segment of casAB was also deleted. Sequence analysis of casAB and promoter revealed the presence of DNA regions very similar to the recognition site for FLP recombinase and are presumed to be responsible for this deletion.

The resulting strain was acclimated to minimal media by sequentially subculturing with a 1% inoculum. Both cell growth and lactate production improved during these transfers. Broth from the last transfer was streaked on solid medium for the isolation of clones. One was selected and designated SZ132.

Construction of Strain SZ186

A further derivative of SZ132 was constructed in which all foreign genes were removed. The *K. oxytoca* casAB and *E. chrysanthemi* celY genes were deleted by homologous recombination using linear DNA. FLP recombinase was used to eliminate antibiotic genes used during constructions. The resulting strain, SZ186, contains only native *E. coli* genes.

Analysis of Lactic Acid Production

Analogous genetic mutations were constructed in derivatives of *E. coli* K-12 and *E. coli* B to produce SZ63 (Zhou et al., 2003) and SZ132, respectively. SZ132 was superior to SZ63 in terms of cell growth and lactate (D isomer) production (see FIG. 1A). In rich medium, SZ132 completed the fermentation of 10% glucose in 48 h to produce over 1 mole lactate/l of fermentation broth, twice that reported previously for *E. coli* K-12-based strains. Fermentations with SZ63 and 10% glucose stalled after 72 h and produced only 840 mmoles lactate/l of broth after 120 h. In rich media, lactate yields were higher for SZ132 (95%) than for the K-12 strain SZ63 (88%). The maximum volumetric productivity for SZ132 was 75 mmoles/l h, 76% higher than for SZ63 (Table 2).

TABLE 2

Summary of Lactic Acid Fermentations

| E. coli strains | Substrate | Lactic Acid Produced | | | Co-products produced (mM) | | |
|---|---|---|---|---|---|---|---|
| | | Concentration (mM) | Base adjusted concentration (mM) | Yield (%) | Succinate | Acetate | Ethanol |
| SZ132 | NBS 10% Glu | 556.01 ± 0.54 | 614.09 ± 0.54 | 91 | 32.11 ± 1.49 | 13.95 ± 0.57 | ≦1 |
| SZ132 | NBS 10% Glu + Betaine | 792.23 ± 8.67 | 930.30 ± 8.67 | 86 | 78.92 ± 2.45 | 11.56 ± 0.75 | ≦1 |
| SZ132 | NBS 10% Suc | 556.88 ± 33.21 | 609.78 ± 33.21 | 92 | 2.79 ± 0.02 | ≦1 | ≦1 |
| SZ132 | NBS 10% Suc + Betaine | 889.06 ± 157.53 | 1045.95 ± 157.53 | 88 | 38.00 ± 7.33 | 12.24 ± 3.72 | ≦1 |
| SZ186 | NBS 10% Glu | 600.41 ± 2.67 | 670.31 ± 2.94 | 99 | ≦1 | ≦1 | ≦1 |
| SZ186 | NBS 10% Glu + Betaine | 658.75 ± 21.37 | 744.39 ± 24.15 | 98 | ≦1 | ≦1 | ≦1 |
| SZ186 | NBS 10% Suc | 573.27 ± 21.98 | 635.76 ± 24.38 | 95 | ≦1 | ≦1 | ≦1 |
| SZ186 | NBS 10% Glu + Betaine | 638.41 ± 33.59 | 718.06 ± 38.19 | 96 | ≦1 | ≦1 | ≦1 |
| SZ194 (Deposit No. NRRL B-30863) | NBS 10% Glu + Betaine | 717.60 + 51.51 | 823.85 + 65.48 | 96 | ≦1 | ≦1 | ≦1 |
| SZ194 | LB pH 6.5 10% Glu + Betaine | 607.52 + 6.17 | 676.77 + 6.87 | 92 | ≦1 | ≦1 | ≦1 |
| SZ194 | LB pH 7.0 10% Glu + Betaine | 714.06 + 7.38 | 813.35 + 9.61 | 95 | ≦1 | ≦1 | ≦1 |
| SZ194 | LB pH 7.5 10% Glu + Betaine | 913.16 + 25.73 | 1070.19 + 27.57 | 97 | ≦1 | ≦1 | ≦1 |
| SZ194 | LB pH 8.0 10% Glu + Betaine | 903.22 + 21.51 | 1060.38 + 25.26 | 96 | ≦1 | ≦1 | ≦1 |
| SZ194 | NBS pH 7.5 10% glu + betaine | 864.31 + 4.93 | 1019.89 + 5.81 | 95 | ≦1 | ≦1 | ≦1 |
| SZ194 | NBS pH 7.5 12% glu + betaine | 1012.18 + 27.41 | 1227.60 + 31.16 | 95 | ≦1 | ≦1 | ≦1 |
| SZ194 | NBS pH 7.5 14% glu + betaine | 1001.08 + 9.48 | 1217.02 + 13.51 | 95 | ≦1 | ≦1 | ≦1 |
| SZ194 | NBS pH 7.5 6 + 3 + 3% glu + betaine | 1003.65 + 12.74 | 1216.45 + 16.48 | 93 | ≦1 | ≦1 | ≦1 |

In NBS mineral salts medium containing 5% glucose, cell yield and volumetric productivity for SZ132 were twice that of SZ63 (see FIG. 1B). Strain SZ132 completed the fermentation of 5% glucose within 36 h, less than ¼ of the time required for SZ63. Under these conditions, cell yield and volumetric productivity for fermentations with NBS mineral salts medium were only 25-35% of those with rich medium and 10% glucose.

Neither strain SZ132 nor SZ63 completed the fermentation of 10% glucose in NBS mineral salts medium within 144 h (see FIG. 1C). Lactate yields for both strains were over 90% based on metabolized sugar. With NBS mineral salts medium containing 10% glucose, cell yield (0.83 g/l), lactate production (700 mmoles/l of fermentation broth), and volumetric productivity (11.2 mmoles lactate/l h) for SZ132 were approximately two-fold higher than for SZ63. With NBS mineral salts medium and 10% glucose, volumetric productivity for SZ132 was less than 20% of that observed in rich medium.

Sucrose was fermented more slowly than glucose in rich medium and in NBS mineral salts medium. Previous studies have shown that SZ63 (pLOI3501) required 36 h to complete the fermentation of 5% sucrose in rich medium but was unable to complete the fermentation of 10% sucrose in this medium. SZ132 completed the fermentation of 10% sucrose in rich medium within 120 h and produced over 1 mole lactate/l of fermentation broth (see FIG. 1D), almost twice that previously reported for SZ63 harboring the sucrose plasmid.

Volumetric productivity for SZ132 in NBS mineral salts medium containing 10% sucrose (9.3 mmoles/l h) was ⅓ of that observed in rich medium with sucrose, less than ⅛ that observed in rich medium containing 10% glucose (Table 2). Although 5% sucrose was fermented to completion in NBS mineral salts medium within 72 h (see FIG. 1E), 10% sucrose was not fully metabolized in this medium even with extended incubation times (FIG. 1F). Based on sugar metabolized, yields for sucrose ranged from 86% to 93% in both media.

These results demonstrate that high levels of organic acids can be produced from glucose and/or sucrose by modified strains of *E. coli* B. Maximum volumetric productivity was estimated at 75 mmoles lactate/l h in rich medium (LB), over 3-fold higher than with NBS mineral salts medium. Many opportunities remain for improvement. Incubation times required to complete the metabolism of 10% sucrose were 3-fold longer than for 10% glucose in complex medium, longer still in mineral salts medium. Reducing fermentation times without the costly addition of complex nutrients may be essential. Identifying the constituents that increase growth and productivity could substantially reduce costs associated with fermentation and also offer an opportunity to reduce expenses associated with lactate purification and waste treatment.

FIGS. 2-5 illustrate progress of lactic acid (D isomer) production by various embodiments, namely SZ132, SZ186, and SZ194 (Deposit No. NRRL B-30863) of the invention under various fermentation conditions in NBS mineral salts medium.

EXAMPLE 2

Preparation of *E. Coli* Strain SZ194

Strains and plasmids used in the preparation of Strain SZ194 are listed in Table 3. Cultures were grown at 37° C. in modified Luria broth (per liter: 10 g Difco tryptone, 5 g Difco yeast extract, 5 g sodium chloride) (Miller, J. H. 1992 *A Short Course in Bacterial Genetics: A Laboratory Manual and Handbook for Escherichia coli and Related Bacteria*. Cold Spring Harbor Press, Cold Spring Harbor, N.Y.) or in NBS mineral salts medium (Causey, T. B. et al. 2004, "Engineering *Escherichia coli* for efficient conversion of glucose to pyruvate," *Proc. Natl. Acad. Sci. USA* 101:2235-2240) supplemented with 1 mM betaine and 2%-14% (w/v) sugar (glucose or sucrose). When needed, ampicillin (50 mg/L) and kanamycin (50 mg/L) were used for strain constructions.

TABLE 3

*E. coli* Strains and Plasmids

| | Relevant Characteristics | Sources |
|---|---|---|
| Strains | | |
| SZ132 | Δ(focA-*Z. mobilis* pdc-adhB-pflB) adhE::FRT Δack::FRTΔfrd, frdA:: *E. chrysanthemi* celY lacY::*K. oxytoca* casAB | Zhou et al. (2005) |
| SZ136 | SZ132, selected for rapid growth and fermentation in 10% sucrose | This example |
| SZ162 | SZ136, Δ frdBC::FRT Δ adhE::FRT | This example |
| SZ186 | SZ162, Δ casAB::FRT Δ celY::FRT | This example |
| SZ186 | SZ186, selected for rapid growth and fermentation in 10% glucose | This example |
| Plasmids | | |
| pKD46 | Bla γ β exo (Red recombinase), temperature conditional pSC101 replicon | Datsenko and Wanner (2000) |
| pFT-A | Bla flp temperature conditional pSC101 replicon | Posfai et al. (1997) |
| pLOI2511 | colE1, FRT-kan-FRT, bla | |
| pLOI3924 | colE1, bla kan lacY'-FRT-Kan-FRT-lacYA | |

Standard methods were used for DNA amplification, enzyme digestion, purification and plasmid construction (Miller et al., 1992; Sambrook and Russell, 2001). Methods for chromosomal gene deletion and integration have been previously described (Causey et al., 2004; Datsenko and Wanner, 2000; Martinez-Morales et al., 1999; Zhou et al., 2003a).

Plasmid pLOI3924 was constructed to facilitate deletion of the casAB genes by cloning lacY and lacA genes using ORFmers (Sigma-Genosis, The Woodlands, Tex.), and inserting the FRT-kan-FRT cassette (SmaI digestion) from pLOI2511 between the NdeI site in the carboxyterminus of lacY and the N-terminal ATG of lacA. The amplified fragment (forward ORFmer for lacY; reverse ORFmer for lacA) from this plasmid was used for chromosomal integration, deleting the casAB genes. Hybrid primers used for additional gene deletions and contained sequence corresponding to approximately 45 base pairs of the beginning or end of the target gene plus 20 base pair of DNA sequence corresponding to the FRT-flanked kanamycin cassette are described in Table 4.

TABLE 4

Primers

| Primer | SEQ ID NO: | Sequence |
|---|---|---|
| sense primer for frdBC deletion | 1 | ATGGCTGAGATGAAAAACCTGAAAAT TGAGGTGGTGCGCTATAACGTGTAGGC TGGAGCTGCTTC |

TABLE 4-continued

Primers

| Primer | SEQ ID NO: | Sequence |
|---|---|---|
| antisense primer for frdBC deletion | 2 | TTACCAGTACAGGGCAACAAACAGGA TTACGATGGTGGCAACCACCATATGAA TATCCTCCTTAG |
| sense primer for adhE deletion | 3 | ATGGCTGTTACTAATGTCGCTGAACTT AACGCACTCGTAGAGCGTGTGTAGGCT GGAGCTGCTTC |
| antisense primer for adhE deletion | 4 | TTAAGCGGATTTTTTCGCTTTTTTCTCA GCTTTAGCCGGAGCAGCCATATGAATA TCCTCCTTAG |
| sense primer for celY deletion | 5 | GATAAGGCGGAAGCAGCCAATAAGAA GGAGAAGGCGAATGGCTGAGTGTAGG CTGGAGCTGCTTC |
| antisense primer for celY deletion | 6 | CCAGAATACCGGTTCGTCAGAACGCTT TGGATTTGGATTAATCATCATATGAAT ATCCTCCTTAG |

Unless otherwise specified, NBS mineral salts medium (Causey et al., 2004) containing 1 mM betaine and 10% sugar (glucose or sucrose) was used in all fermentations (pH 7.0). Seed cultures were prepared as described previously (Zhou et al., 2003) and used to inoculate 500 ml fermentation vessels (350 ml working volume, 35° C., 150 rpm agitation) to an initial density of 33 mg cdw l$^{-1}$. Where indicated, betaine (1 mM) was also added. Broth pH was maintained by automatic addition of 6 N KOH. A total of 12% (w/v) glucose was used in the fed batch fermentations (6%+3%+3%) as follows: 308 ml of NBS medium containing 21 grams of glucose. After 24 h and 48 h, 21 ml of 50% glucose was slowly added into each vessel.

Cells from pH-controlled fermentations were serially transferred at various times (24 or 48 h) to facilitate metabolic evolution through growth-based selection. Sequentially transferred cultures were inoculated at an initial density of 33 mg cdw l$^{-1}$. Clones isolated at the end of selections were assigned new strain designations.

Cell mass was estimated by measuring optical density at 550 nm using a Bausch & Lomb Spectronic 70 spectrophotometer. Total organic acid production (primarily lactate) was estimated by base (KOH) consumption for pH maintenance. Acidic products and chiral purity were analyzed at the end of fermentation by high-performance liquid chromatography (Zhou et al., 2003a). Plotted data represent an average of 2 or more replicates. Bars denoting the standard deviation are included for averages of 3 or more fermentations.

Analysis of Lactic Acid Production

Figures 6A, 6B:
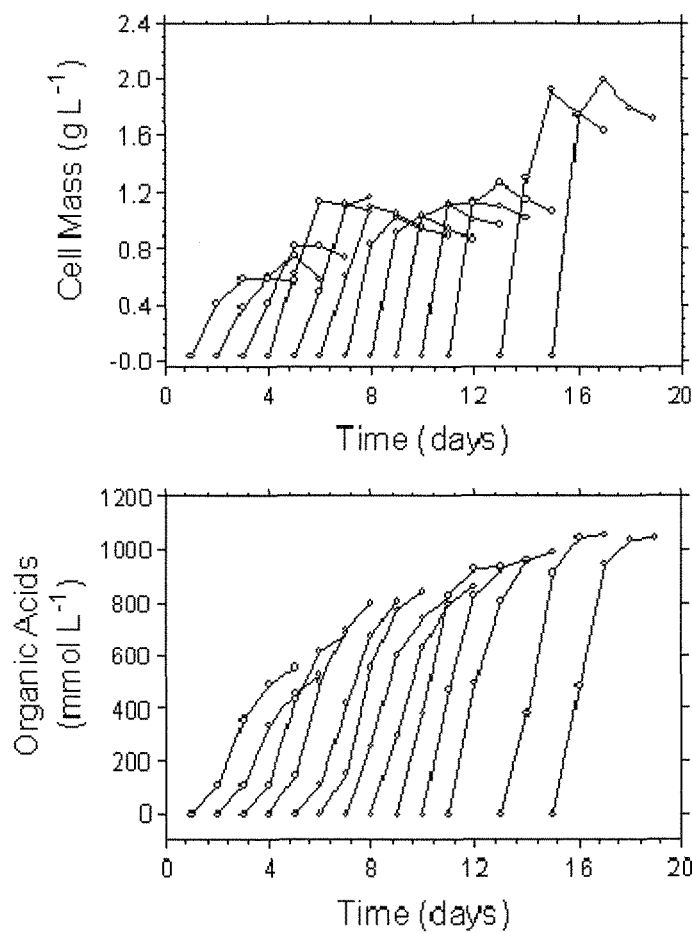
FIG. 6A shows cell mass.
FIG. 6B shows total organic acids (base consumed).

Betaine, a protective osmolyte, was highly beneficial for cell growth and lactate production by SZ132 in mineral salts medium containing high sugar concentrations, presumably due to insufficient carbon partitioning into the biosynthesis of native osmolytes such as glutamate and trehalose (Purvis et al., 2005). Serial transfers of SZ132 were carried out in mineral salts medium containing 10% sucrose to select for strains with equivalent performance in the absence of betaine (FIGS. 6A and 6B). Energy production for growth in strain SZ132 is dependent on glycolytic flux with lactate as the dominant route for NADH oxidation, providing a growth-basis selection. Growth and acid production (base consumption) improved steadily during serial transfers. In the final transfers, 10% sucrose was fermented to completion without added betaine. A clone was isolated from this culture and designated strain SZ136. This strain produced twice the cell yield of the parent, SZ132, and 3-fold higher titers of lactate after 96 h (FIG. 6). However, SZ136 also produced higher levels of succinate and ethanol than SZ132 (Table 5), reducing lactate yield (based on metabolized sugar).

TABLE 5

Products from glucose fermentations

| | | Lactate | | Co-products (mmol l$^{-1}$) | | |
|---|---|---|---|---|---|---|
| Strain | Conditions[a] | mmol l$^{-1}$ | Yield (%)[b] | Succinate | Acetate | Ethanol |
| SZ132 | NBS + betaine | 930 ± 9 | 86 | 79 ± 2 | 12 ± 1 | <1 |
| SZ136 | NBS | 739 | 67 | 126 | 8 | 115 |
| SZ162 | NBS | 660 ± 27 | 96 | <1 | <1 | <1 |
| SZ186 | NBS | 670 ± 3 | 99 | <1 | <1 | <1 |
| SZ186 | NBS + betaine | 744 ± 24 | 98 | <1 | <1 | <1 |
| SZ194 | NBS + betaine | 824 + 65 | 96 | <1 | <1 | <1 |
| SZ194 | Luria broth pH 6.5 | 677 ± 7 | 92 | <1 | <1 | <1 |
| SZ194 | Luria broth pH 7.0 | 813 ± 10 | 95 | <1 | <1 | <1 |
| SZ194 | Luria broth pH 7.5 | 1070 ± 28 | 97 | <1 | <1 | <1 |
| SZ194 | Luria broth pH 8.0 | 1060 ± 25 | 96 | <1 | <1 | <1 |
| SZ194 | NBS, pH 7.5 + betaine | 1020 ± 6 | 95 | <1 | <1 | <1 |
| SZ194 | NBS pH 7.5 12% glucose + betaine | 1228 ± 31 | 95 | <1 | <1 | <1 |
| SZ194 | NBS, pH 7.5 14% glucose + betaine | 1217 ± 14 | 95 | <1 | <1 | <1 |
| SZ194 | NBS, pH 7.5 glucose | 1216 ± 17 | 93 | <1 | <1 | <1 |

TABLE 5-continued

| | | Products from glucose fermentations | | | | |
|---|---|---|---|---|---|---|
| | | Lactate | | Co-products (mmol l$^{-1}$) | | |
| Strain | Conditions[a] | mmol l$^{-1}$ | Yield (%)[b] | Succinate | Acetate | Ethanol |
| | (6 + 3 + 3%) + betaine | | | | | |

[a]NBS mineral salts medium containing 10% glucose (pH 7.0) unless specified otherwise. Where indicated, 1 mM betaine was also added.
[b]Yields are based on metabolized sugar assuming a maximum theoretical yield of 2 moles of lactate per mole of hexose (equal weight conversion).

Improvements in growth in SZ132 on 10% (w/v) sucrose appear to have been accompanied by mutations that improved growth but also partially restored the function of mutated genes for co-product pathways. The fumarate reductase mutation in strain SZ132 is poorly characterized and was originally obtained as a Tn5 deletion (Ohta et al., 1991), followed by insertion of celY between frdA and frdB (Zhou et al., 2005). The alcohol dehydrogenase gene was disrupted by insertion of an antibiotic marker with flanking FRT sites. Flippase was then used to remove the antibiotic gene leaving only an FRT region. Further deletion of coding regions for frdBC and adhE to produce SZ162 eliminated both co-products but also reduced growth and the final lactate titer due to incomplete sugar utilization (Table 5). Additional deletions were also made in this strain to eliminate foreign genes that had been previously integrated for cellulose utilization (Zhou et al., 2005): casAB (cellobiose transporter gene) from *Klebsiella oxytoca* and celY (endoglucanase) from *Erwinia chrysanthemi*. The resulting strain, SZ186, produced negligible levels of co-products but failed to completely utilize 10% sugar in mineral salts medium with or without betaine (FIG. 7A; Table 5). However, yields based on metabolized sugar were high (96%-99%) for both SZ162 and SZ186.

Figure 7A:
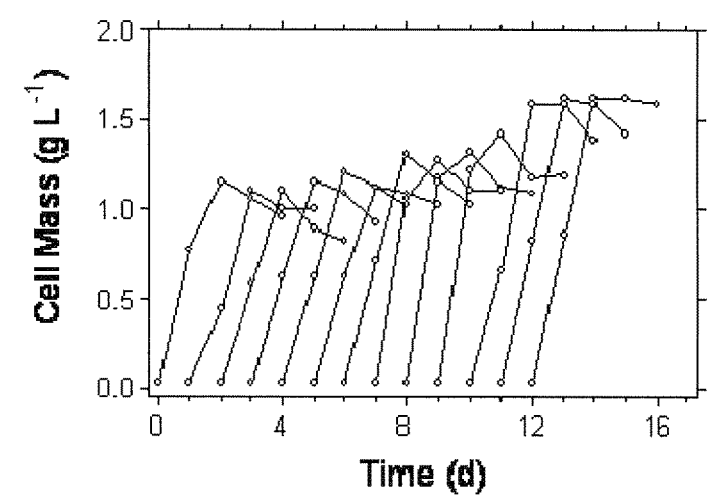
FIG. 7A shows cell mass.
Figure 7B:
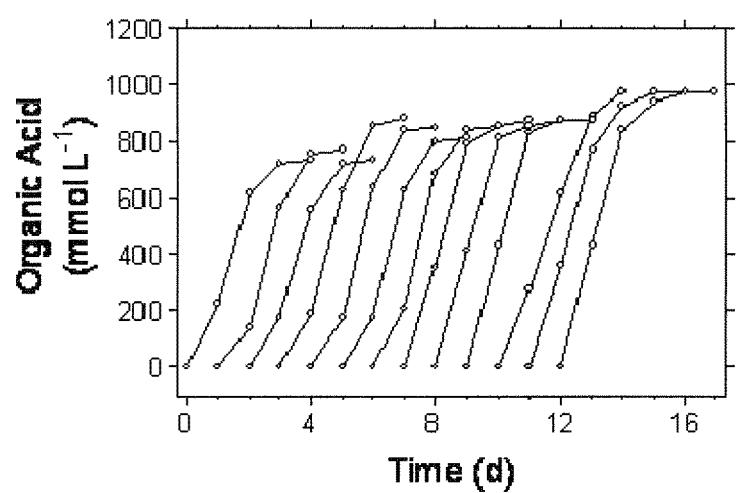
FIG. 7B shows total organic acids (base consumed to maintain pH).

Deletions in SZ136 that eliminated co-product pathways (SZ186) also reduced cell yield by almost half, adversely affecting the partitioning of carbon into biosynthesis. Metabolic evolution was used to co-select a derivative of SZ186 with both improved growth and fermentation performance in the presence of 1 mM betaine and 10% glucose (FIGS. 7A and 7B). Cell yield and organic acid production increased concurrently during the initial rounds of selection. A single clone was isolated from the last enrichment and designated SZ194.

Strain SZ194 grew more rapidly than SZ186 and reached a higher cell yield. Lactate concentrations of up to 900 mM were produced by SZ194 in some fermentations, consistently higher than those of SZ186 (Table 5). Both strains produced lactate from glucose at near theoretical yields with minimal co-products. With both strains, however, sugar remained unused at pH 7.0 even after prolonged incubation. At pH 7.0, the 800-900 mM lactate produced from 10% (w/v) glucose is well above the maximum lactate concentration needed to inhibit growth at pH 7.0 and may also inhibit further glucose metabolism.

Two factors were explored as possible causes for the incomplete fermentation of 10% (w/v) sugar by SZ194: an unknown nutritional defect and lactate tolerance. Replacing mineral salts medium containing 1 mM betaine with Luria broth (rich medium) at pH 7.0 had little effect on lactate yield (Table 5) or lactate production (Table 6). Lactate toxicity was tested by comparing the effect of pH on fermentation (Table 5). The toxicity of weak organic acids such as lactate is related in part to the uncoupling action of the conjugate neutral form (Warnecke et al., 2005), which in turn is inversely related to pH. A similar trend was observed for fermentation. In Luria broth, final lactate titers were lowest at pH 6.5 and highest at pH 7.5 and pH 8.0. Changes in pH had less effect on cell yield. At pH 7.5, 10% (w/v) glucose was fermented to completion in 72 h using Luria broth.

TABLE 6

| | | Comparison of lactate productivity | | | | |
|---|---|---|---|---|---|---|
| Strain | Fermentation conditions[a] | Lactate titer (mmol l$^{-1}$) | Cell yield (g l$^{-1}$) | Volumetric[b] productivity (mmol l$^{-1}$h$^{-1}$) | Specific[b] productivity (mmol g$^{-1}$h$^{-1}$) | Volumetric[b] productivity (g l$^{-1}$h$^{-1}$) |
| SZ132 | pH 7.0 | 930 | 2.07 | 24.6 | 11.9 | 2.21 |
| SZ194 | pH 7.0 | 824 | 1.73 | 18.5 | 10.7 | 1.67 |
| SZ194 | pH 7.5 | 1020 | 1.67 | 23.8 | 14.2 | 2.14 |
| SZ194 | Luria broth, pH 7.5 no betaine added | 1070 | 1.75 | 24.7 | 14.1 | 2.22 |

[a]Mineral salts (NBS) containing 10% (w/v) glucose and 1 mM betaine unless otherwise specified.
[b]Averaged values for the most productive 24-h period.

Figure 3A:
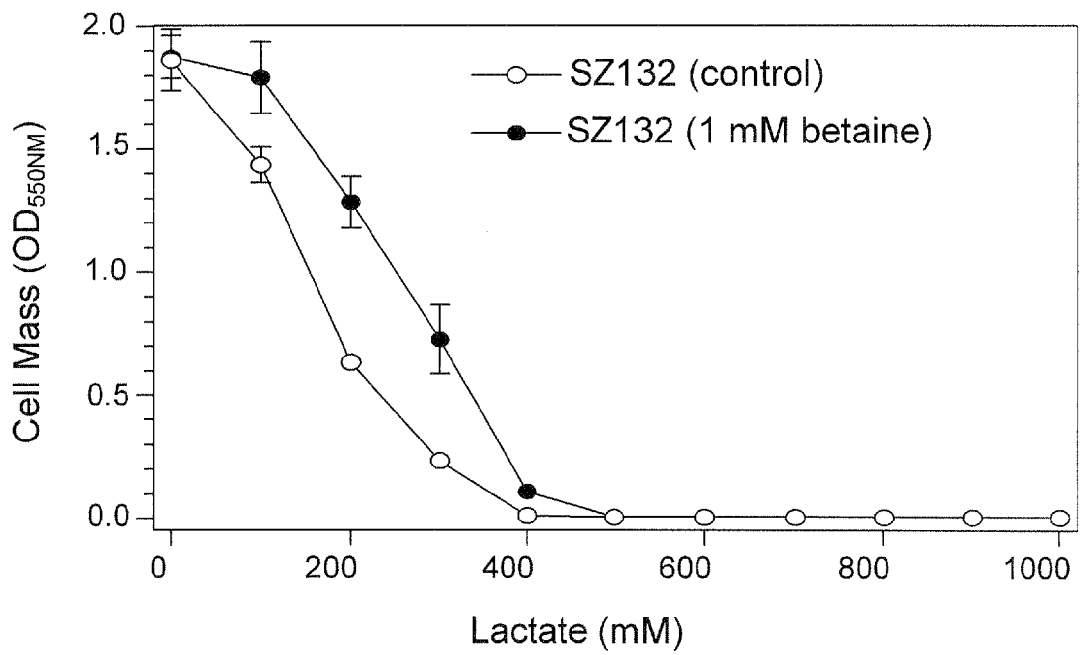
FIGS. 3A-3B illustrate the ability of betaine to increase acid and sugar tolerance during lactic acid production by one embodiment of the invention.
Figure 3B:
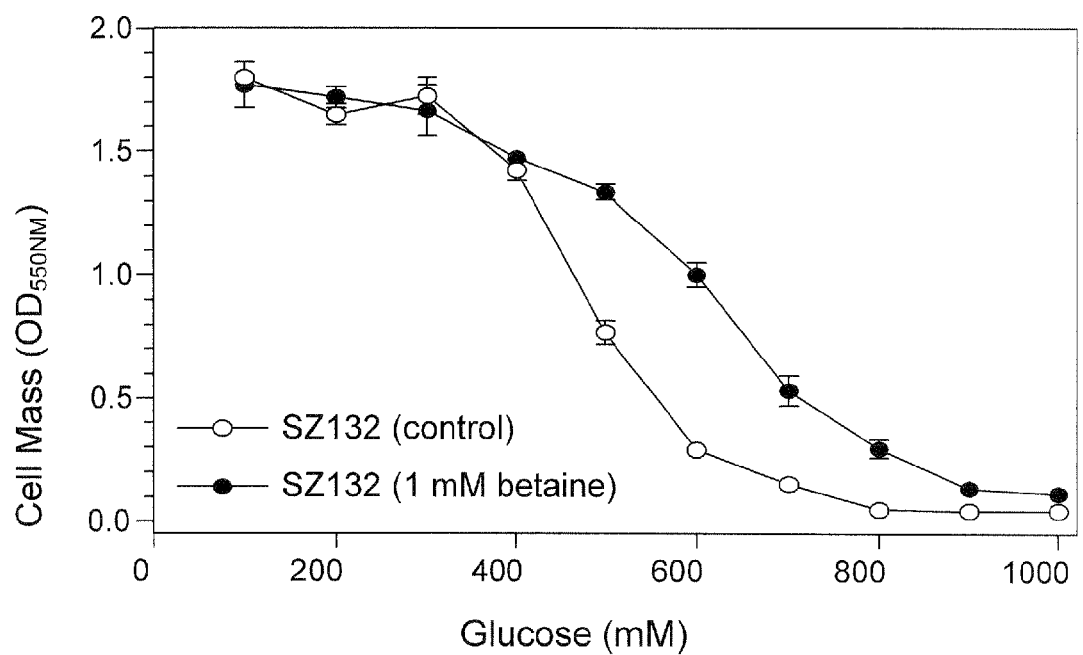
Figure 4A:
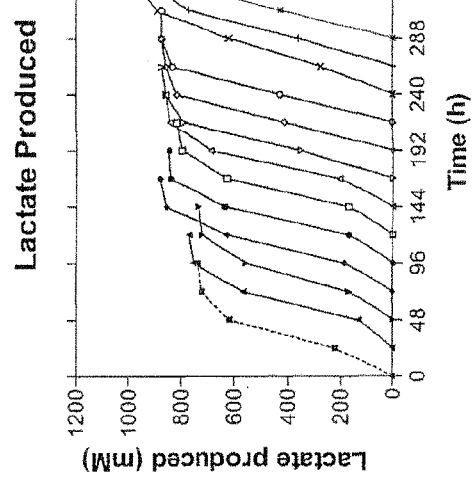
FIGS. 4A-4B illustrate the ability of one embodiment of the invention to acclimatize to mineral media.
Figure 4B:
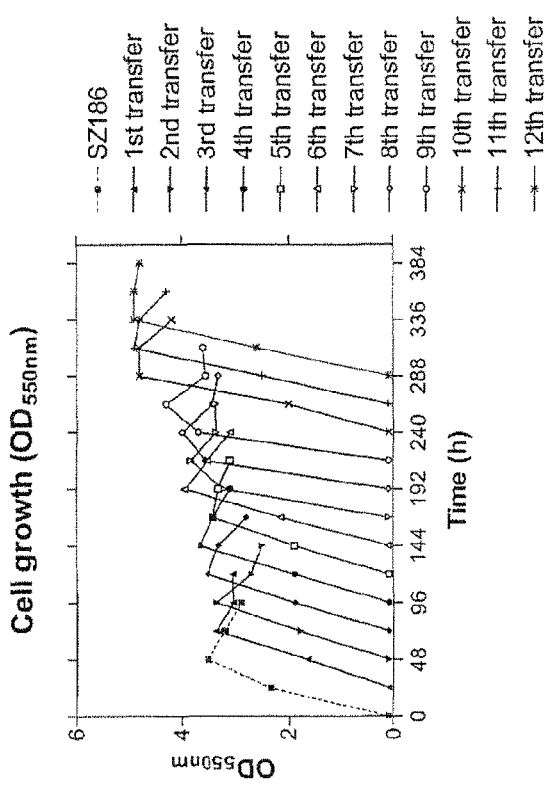
Figure 5A:
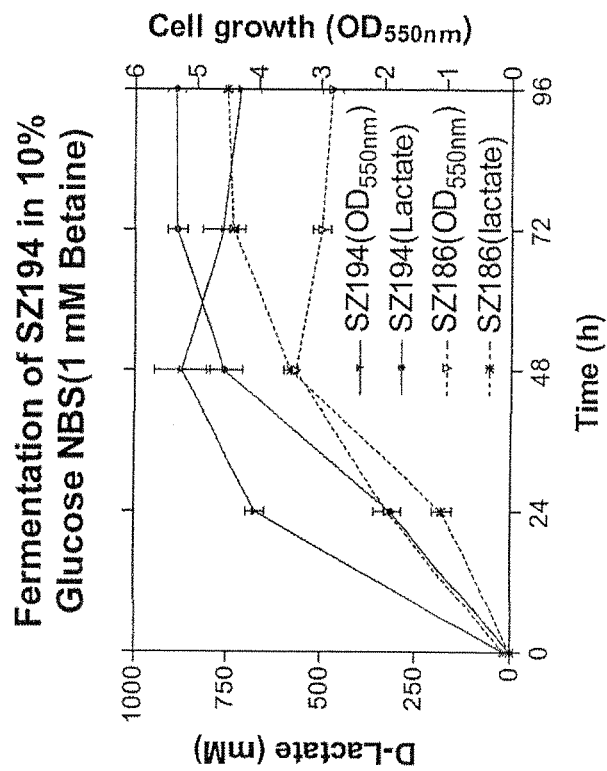
FIGS. 5A-5G illustrate progress of lactic acid production by yet another embodiment of the invention under various fermentation conditions.
Figure 5B:
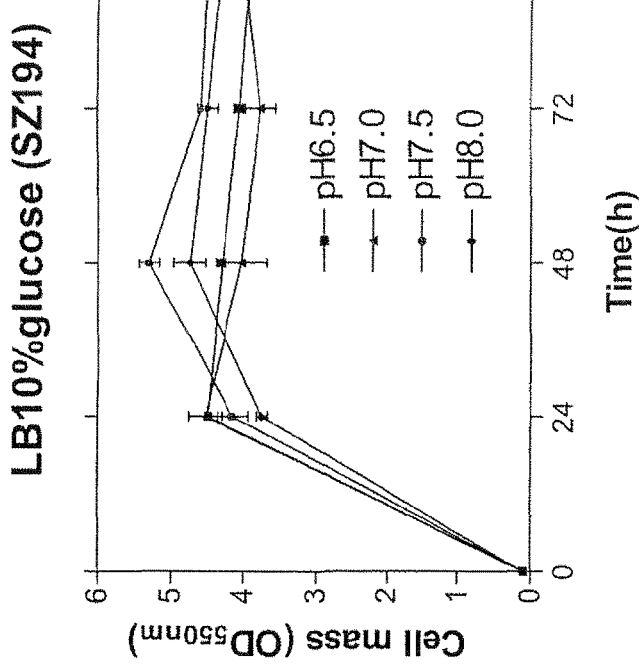
Figure 5C:
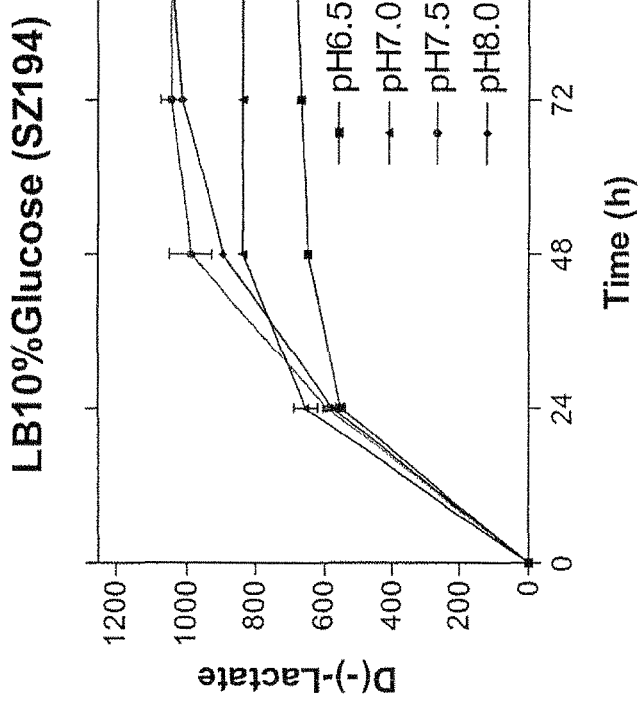
Figure 5E:
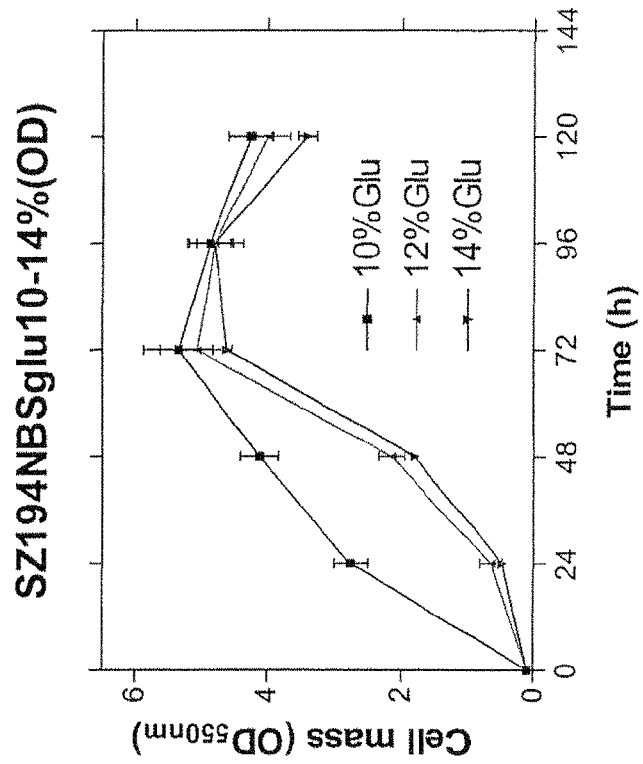
Figure 5D:
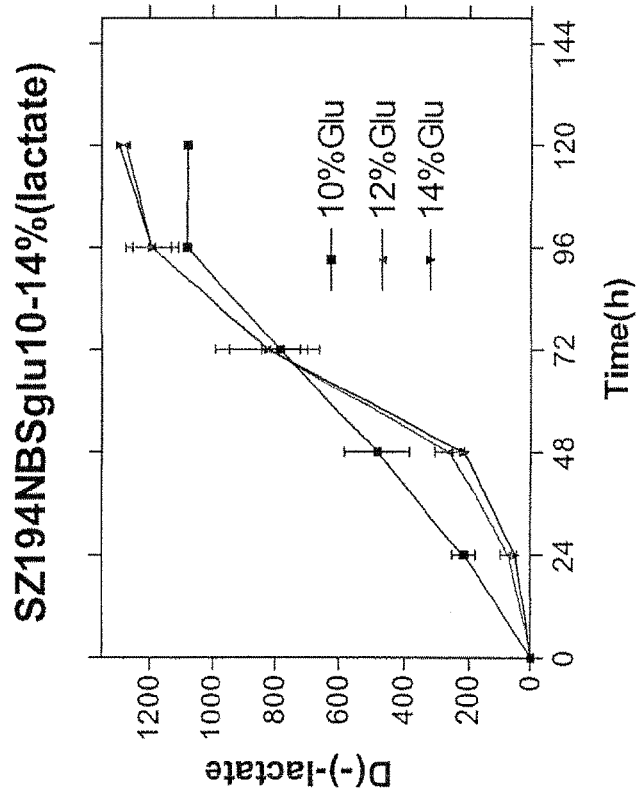
Figure 5G:
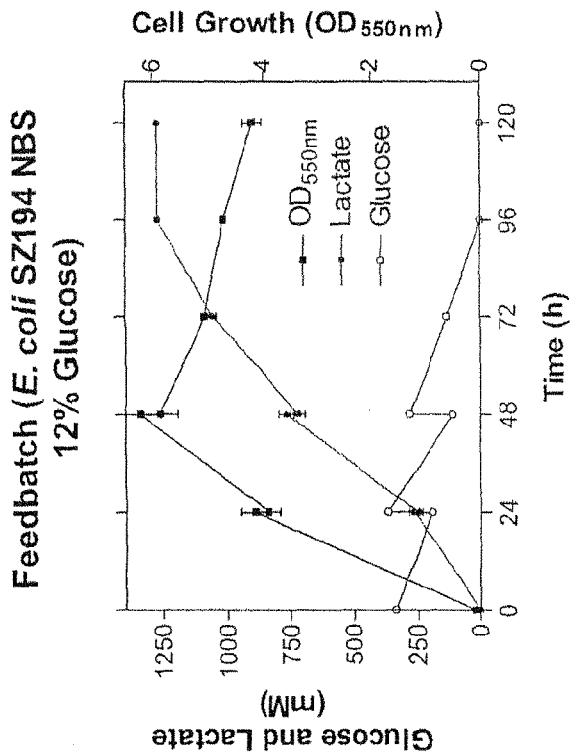
Figure 5F:
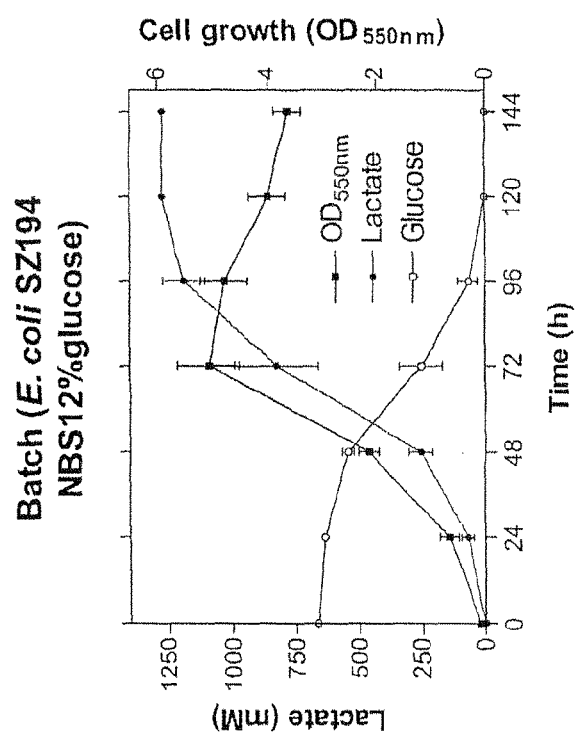
Figures 8A, 8B:
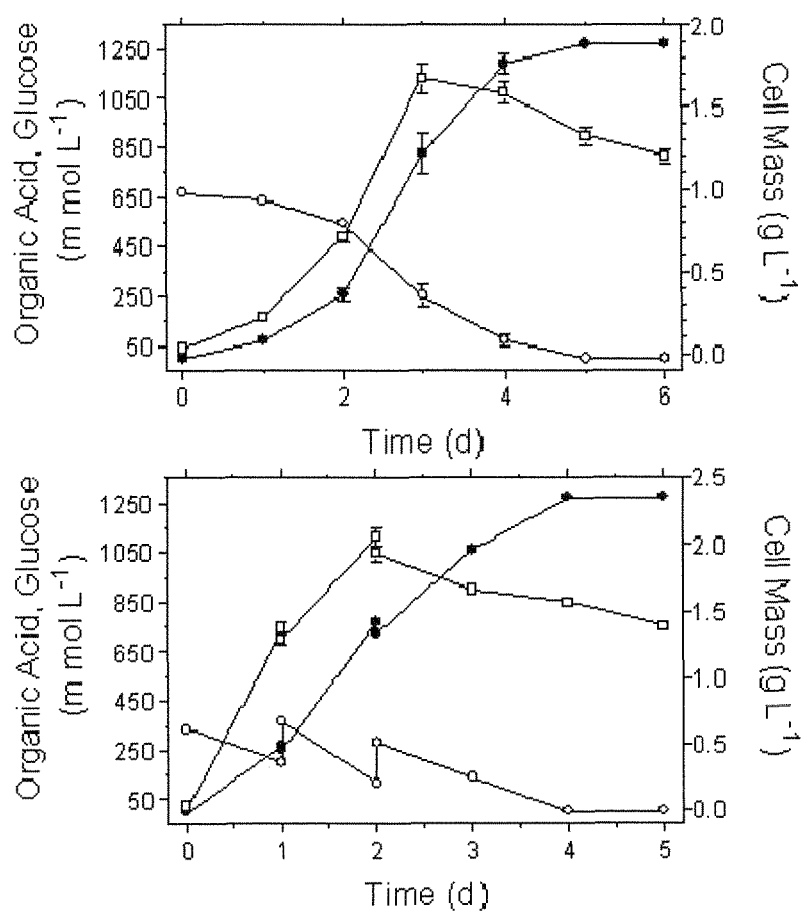
FIG. 8A shows simple batch fermentation containing 12% (w/v) glucose.
FIG. 8B shows fed-batch fermentation. Symbols for all: □, cell mass; ●, total organic acids (base consumed to maintain pH); ○, glucose.

The benefit of this increase in pH was confirmed in mineral salts medium containing 1 mM betaine (FIG. 8; Table 5). At pH 7.5, 10% and 12% (w/v) glucose were fermented to completion, producing over 1 mol lactate $l^{-1}$ with only trace amounts of co-products (FIG. 3A). Product yields of 0.95 g lactate per g glucose represent 95% of the maximum theoretical yield based on total sugar added to the fermentation. Addition of higher levels of sugar did not further increase final lactate titers. Similar final titers were observed during fed-batch experiments (FIG. 8B) and did not increase further when additional sugar was added. Final lactate titers of approximately 1.0-1.2 M appear to represent an upper limit for sugar metabolism at pH 7.5 by SZ194 (Table 5).

It is interesting to note that pH 7.5, the optimal pH for fermentation, is very close to that reported for the cytoplasm of E. coli (Axe et al., 1995; Warnecke et al., 2005). Although no lactate transporter genes have been identified in E. coli, several studies have provided evidence for their presence in E. coli and lactic acid bacteria (Axe et al., 1995; Konings, 2002; Poolman, 2002). These transporters are presumed to be lactate/$H^+$ symporters, activities that may increase in efficiency with increases in external pH. According to the "energy recycling model" (Michels et al., 1979), carrier-mediated efflux of metabolic end products such as lactate can lead to generation of an electrochemical proton gradient across the membrane and contribute to ATP production. Lactate efflux in lactic acid bacteria has been estimated to contribute 30% of total cellular energy (van Maris et al., 2004a). Since E. coli SZ194 and lactic acid bacteria metabolize glucose by similar pathways, it is possible that additional ATP is also produced by lactate efflux in E. coli.

The chiral purity of lactate produced by SZ194 was examined and found to be greater than 95% D-lactate. Although good, this chiral purity is lower than that of the parent strain, SZ132 (99.5% D-lactate) (Zhou et al., 2005). The source of this chiral impurity is unknown.

According to the subject invention, lactate titers of over 1 M can be produced by E. coli SZ194 at pH 7.5 in mineral salts medium supplemented with 1 mM betaine. In this medium, lactate productivity and cell yield for SZ194 were equivalent to that in Luria broth (Table 6). The final lactate titer of 110 g $l^{-1}$ and yield (0.95 g lactate g glucose$^{-1}$) for strain SZ194 compare favorably with lactic acid bacteria such as L. helveticus (Kyla-Nikkila et al., 2000) and L. delbrueckii (Demirci et al., 1992) and exceed the performance of previously engineered biocatalysts in rich medium or in mineral salts (Dien et al., 2001; Porro et al., 1999; Saitoh et al. 2005; van Maris et al., 2004b).

EXAMPLE 3

Materials and Methods

Strains, Plasmids, Media and Growth Conditions

E. coli strains, plasmids and primers utilized in this study are listed in Table 7. Strain SZ194 was previously constructed from a derivative of E. coli B (ATCC 11303) and served as a starting point for constructions (see Example 2 and Zhou et al., 2006). During strain constructions, cultures were grown aerobically at 30° C., 37° C., or 39° C. in Luria broth (per liter: 10 g Difco tryptone, 5 g Difco yeast extract and 5 g sodium chloride) (Miller 1992) containing 2% (w/v) glucose or arabinose. Ampicillin (50 mg/L), tetracycline (12.5 or 6.25 mg/L), or kanamycin (25 or 50 mg/L) were added as needed. For fermentation tests, strains were grown without antibiotics at 37° C. in NBS mineral salts medium (Causey et al., 2004) supplemented with 1 mM betaine and 2-12% (w/v) glucose. MOPS buffer (100 mM, pH 7.4) was added to solid and liquid medium under conditions which lacked pH control (plates, tubes, shaken flasks).

Genetic Methods

Manufacturer protocols and standard methods (Miller 1992, Sambrook and Russell 2001) were followed for DNA purification (Qiagen), restriction endonuclease digestion (New England Biolabs), DNA amplification (Stratagene and Invitrogen) and transformation. Methods for chromosomal deletions and integration have been described previously (Causey et al., 2004, Zhou et. al, 2003, Datsenko and Wanner 2000, Martinez-Morales et al., 1999). Hybrid primers (Table 7) containing sequence homologous to the 50 nucleotides of the beginning or end of the mgsA gene (italics) plus 20 nucleotides corresponding to the sequence of the FRT-flanked kanamycin cassette (underlined) of pKD4 were used for deletion of the native mgsA gene. Plasmid pLOI2398 was constructed previously to facilitate integration of Pediococcus acidilactici ldhL into the chromosomal ldhA gene of E. coli (Zhou et al., 2003a).

Fermentations

Pre-inoculum was grown by inoculating a colony into a 250-ml flask (100 ml NBS medium with 2% (w/v) glucose and 100 mM MOPS, pH 7.4). After 16 h (37° C., 120 rpm), this pre-inoculum was diluted into 500-ml fermentation vessels containing 350 ml NBS media (5-12% sugar, with or without 1 mM betaine) to provide 33 mg dcw $l^{-1}$. After 24-h (37° C., 150 rpm, pH controlled at 7.0), this culture was used to provide a starting inoculum of 33 mg dcw $l^{-1}$. Volumetric productivity is reported for the most active 24-h period. Specific productivity was calculated as the quotient of volumetric productivity divided by cell mass at 24 h.

Metabolic Evolution

Cells from pH-controlled fermentations were serially transferred at 24 or 48 h intervals to facilitate metabolic evolution though competitive, growth-based selection. At each transfer, inocula were diluted (1/100 to 1/350) into prewarmed, fresh media. Clones isolated from these selections were assigned new strain designations.

Analyses

Cell mass was estimated by measuring the optical density at 550 nm using a Bausch & Lomb Spectronic 70 spectrophotometer. Total organic acid production, primarily lactate, was estimated by KOH consumption used to maintain pH 7.0. Acidic products and chiral purity were analyzed at the end of fermentation by high-performance liquid chromatography. Estimates of organic acid by base consumption were consistently lower than measurements of lactate by HPLC, presumably due to mineral metabolism.

Results and Discussion

Restoring Chiral Purity for D-(−)-Lactate Production

Figure 9A:
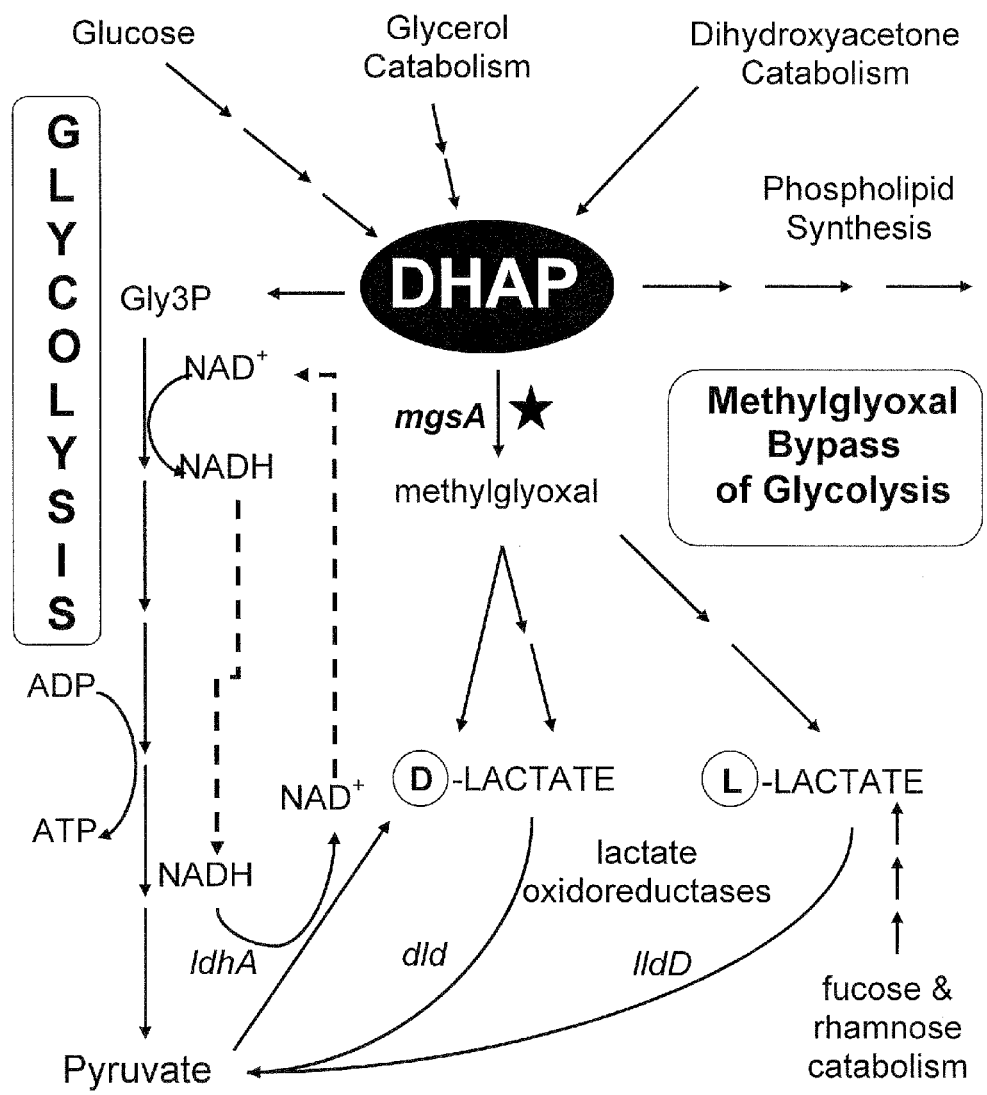
FIGS. 9A-9B show native pathways for lactate production in E. coli.
Figure 9B:
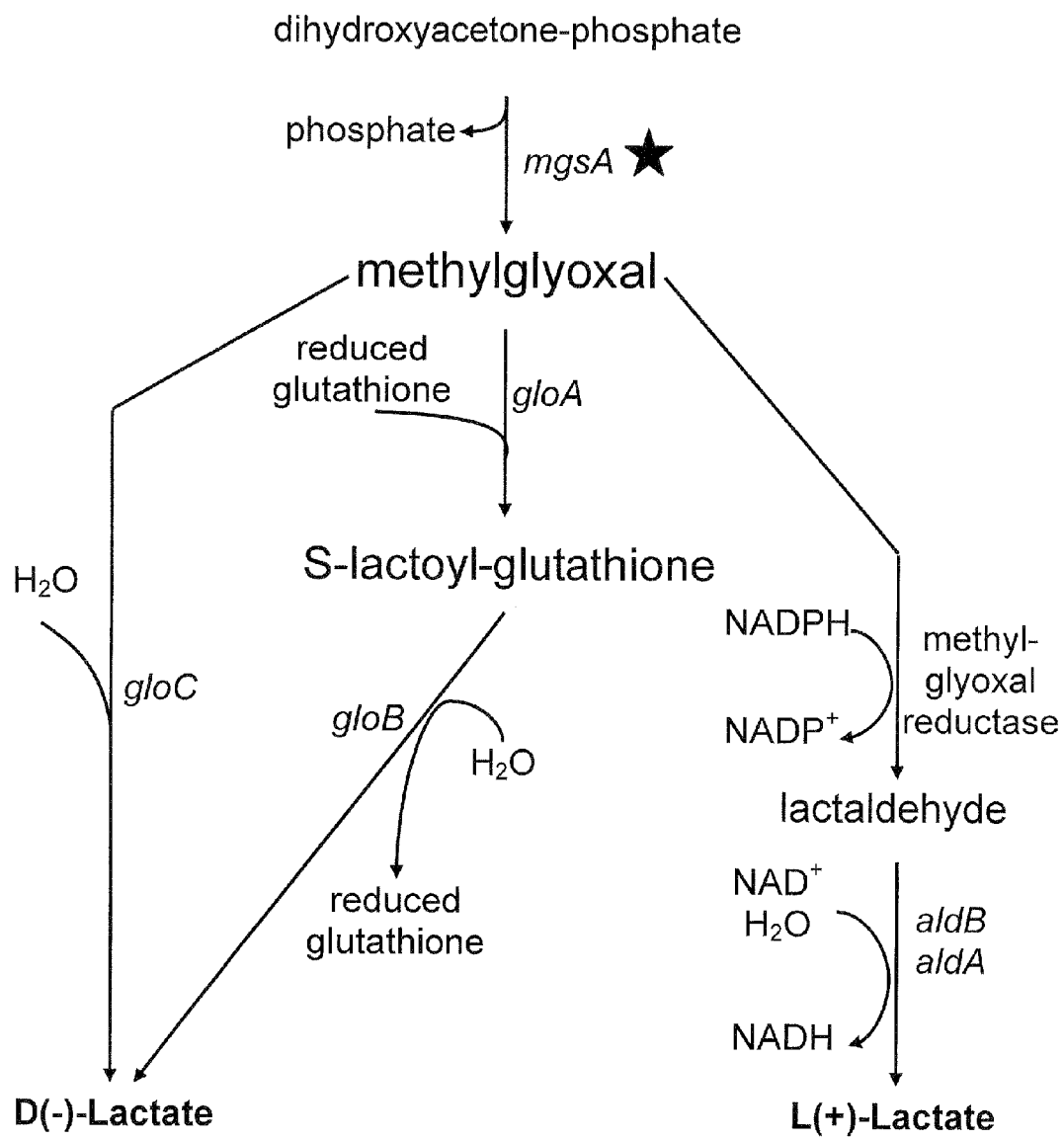
Figure 10A:
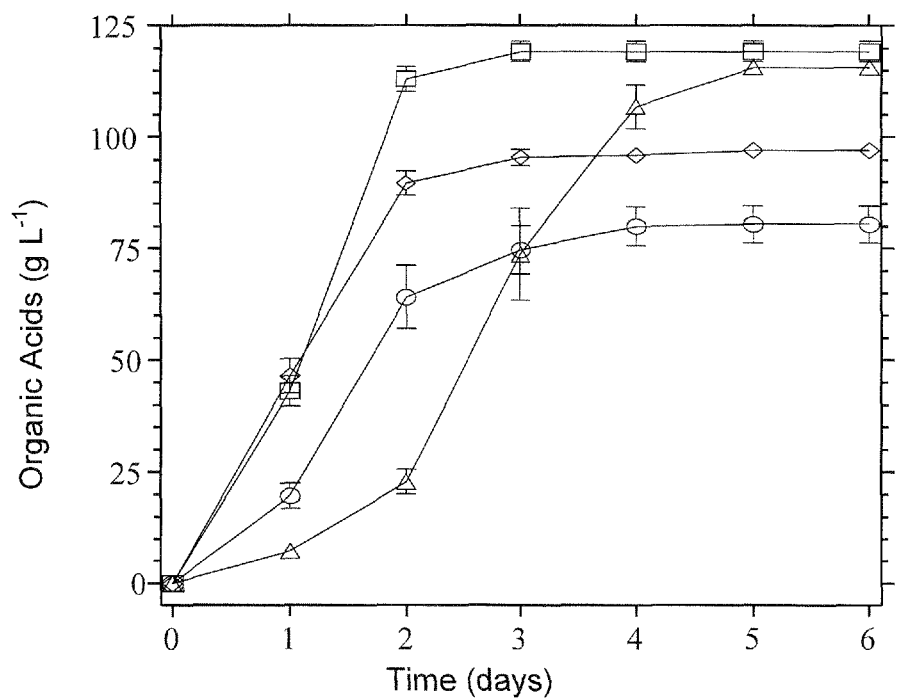
FIGS. 10A-10F show fermentation of 12% (w/v) glucose (NBS mineral salts medium+1 mM betaine) to lactate by recombinant E. coli.
Figure 10B:
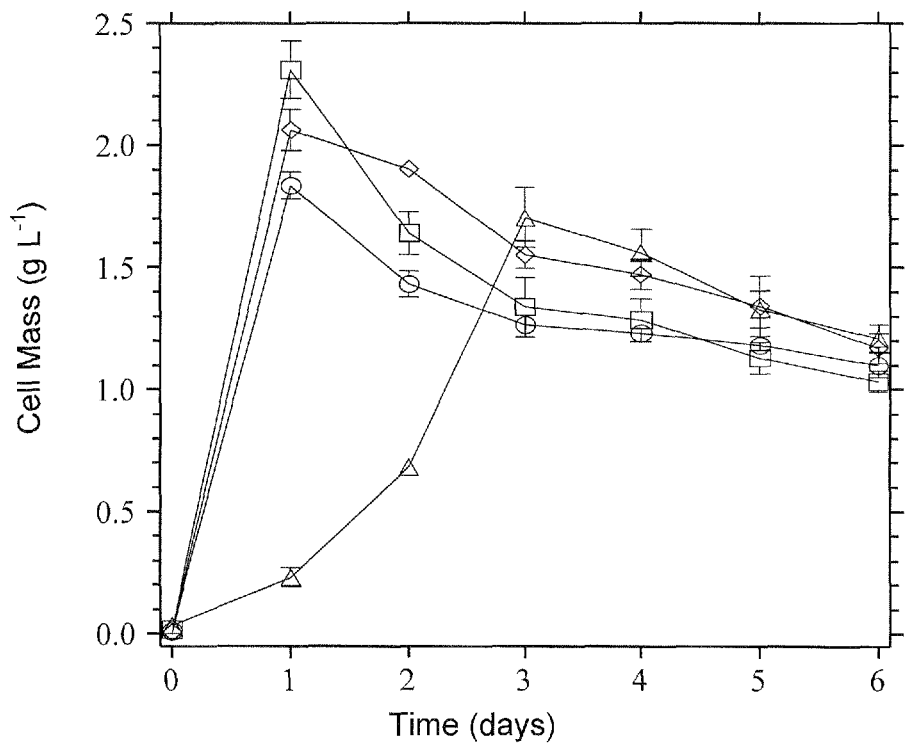

Strain SZ194 has been shown to efficiently produce D-(−)-lactate from glucose at 99% chiral purity in mineral salts medium (Zhou et al., 2006). Betaine increased lactate productivity (titer and rate) with high concentrations of sugar but also decreased chiral purity to 95% (Table 8). There are several possible sources of L-(+)-lactate in E. coli (FIG. 9A). L-(+)-lactate can be produced from lactaldehyde, an intermediate in the catabolism of rhamose or fucose (Badia et al., 1991), both absent in our media, and as a product from the Methylglyoxal Bypass of glycolysis (FIGS. 9A and 9B). The Methylglyoxal Bypass represents a short spillover pathway that is induced by accumulation of dihydroxyacetone-phosphate during rapid glycolysis, and by a phosphate limitation for ATP synthesis. Both the accumulation of dihydroxyacetone-phosphate and phosphate limitation could be exacerbated by high rates of glycolytic flux. To test this hypothesis, the mgsA gene encoding the first committed step, methylglyoxal synthase, was deleted. The resulting strain, TG112, produced chirally pure D-(−)-lactate (Tables 8 and 9; FIGS. 10A and 10B). Growth and initial productivity were increased by this deletion in comparison to SZ194. Yields based on HPLC analyses were similar (Table 8).

Figures 11A, 11B:
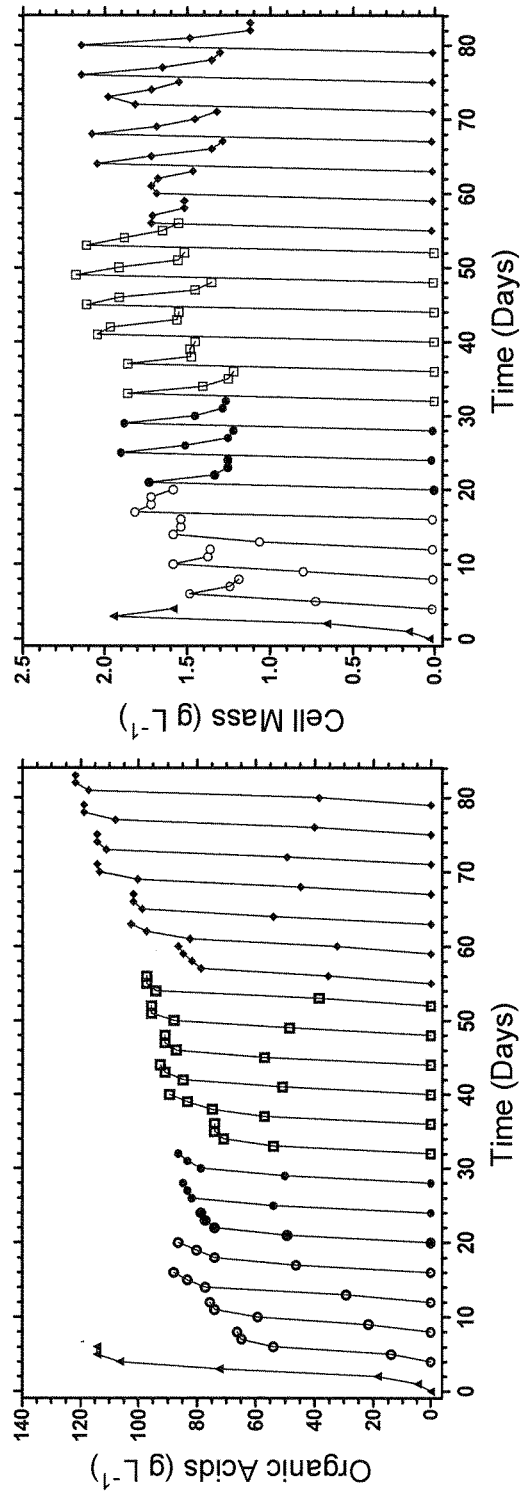
FIGS. 11A-11B show metabolic evolution for improved D-(−)-lactate production and growth. E. coli strain TG112 was sequentially transferred every 24 or 48 hours in a mineral salts medium containing 10% or 12% (w/v) glucose and 1 mM betaine to select for spontaneous mutants with improved growth, hardiness and lactate production. One clone, TG113, was isolated as an intermediate from TG112 transfer number 28 (day 29) and another clone, TG114, from the final culture on day 81. For clarity, graphs from every fourth 24-hour transfer and every other 48-hour transfer are shown. The parent, SZ194, was included for comparison.

Further improvements in TG112 were selected by metabolic evolution during 81 days of growth (FIG. 11). Fermenting cultures were serially transferred in mineral salts medium containing 10% (w/v) glucose, 12% (w/v) glucose, and 12% (w/v) glucose with 1 mM betaine. One clone was isolated at day 28 (TG113) and another at the end of enrichment (TG114). D-(−)-lactate productivity (rate, titer, and yield) and cell yield improved during this process (FIGS. 10A and 10B; Table 8 and Table 9). Fermentation with SZ114 was substantially complete within 48 h in most experiments, with a final yield of 0.98 g D-(−)-lactate $g^{-1}$ glucose. High inocula provided a modest further improvement in specific and volumetric productivities. Co-products and chiral impurities were below detection (<0.1%) with these mgsA-deleted strains. Production of D-(−)-lactate by TG114 compares favorably with other biocatalysts and offers high productivity, titer, yield and chiral purity with simple media and fermentation conditions (Table 10).

Production of Chirally Pure L-(+)-lactate

Figure 10C:
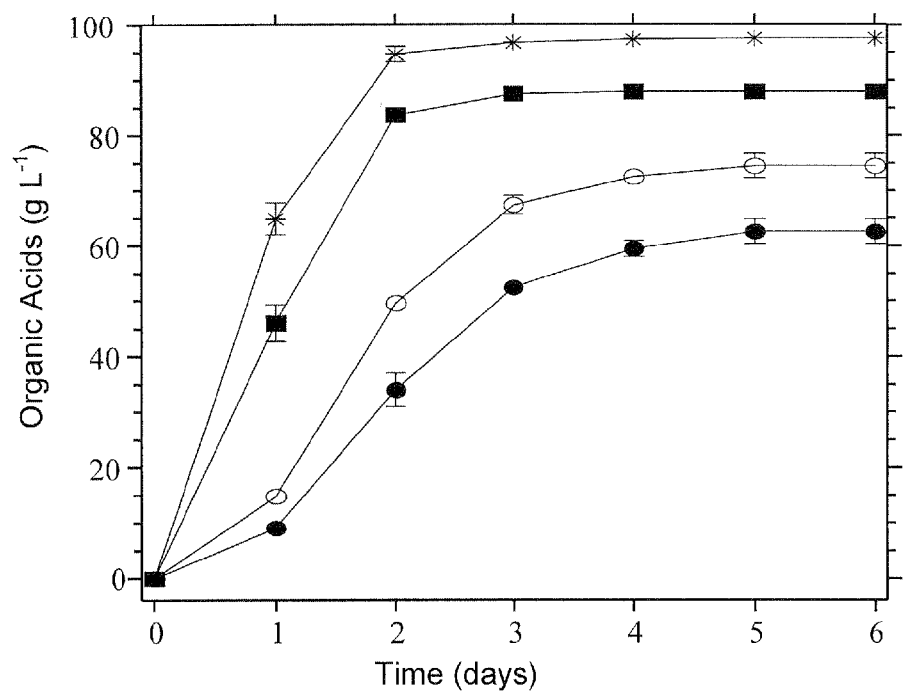
Figure 10D:
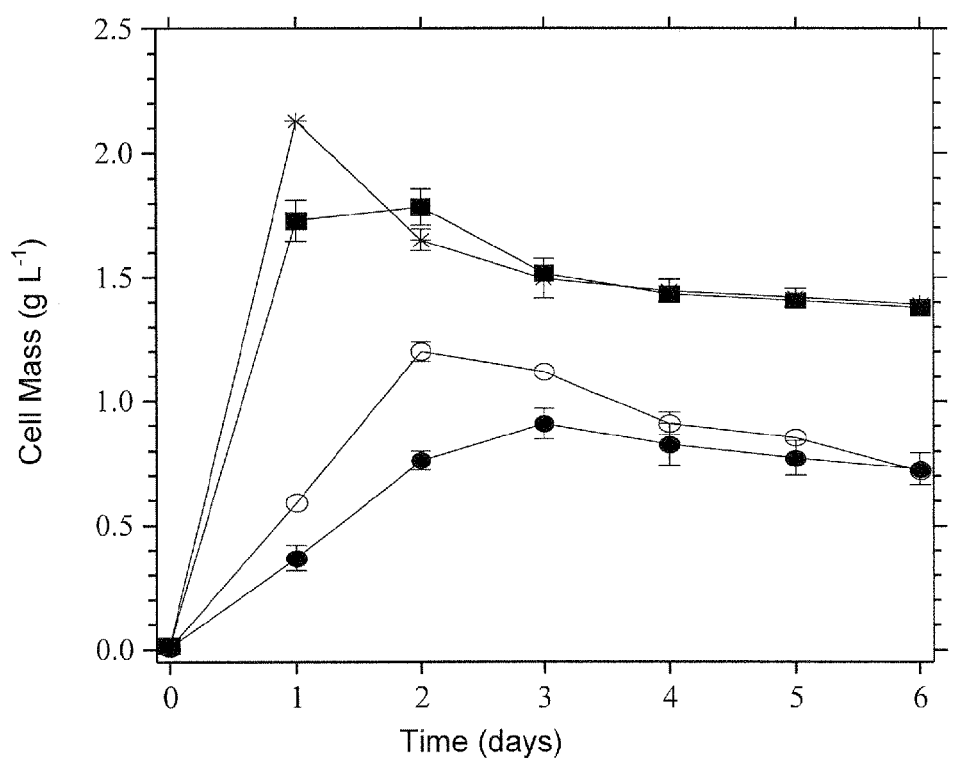
Figure 10E:
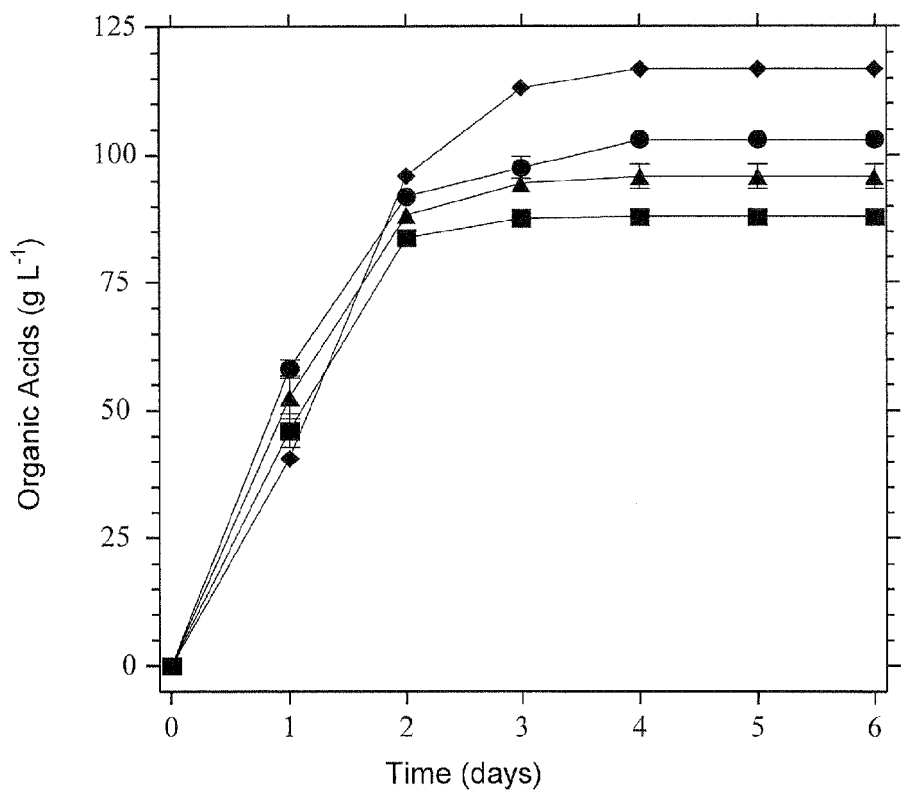
Figure 10F:
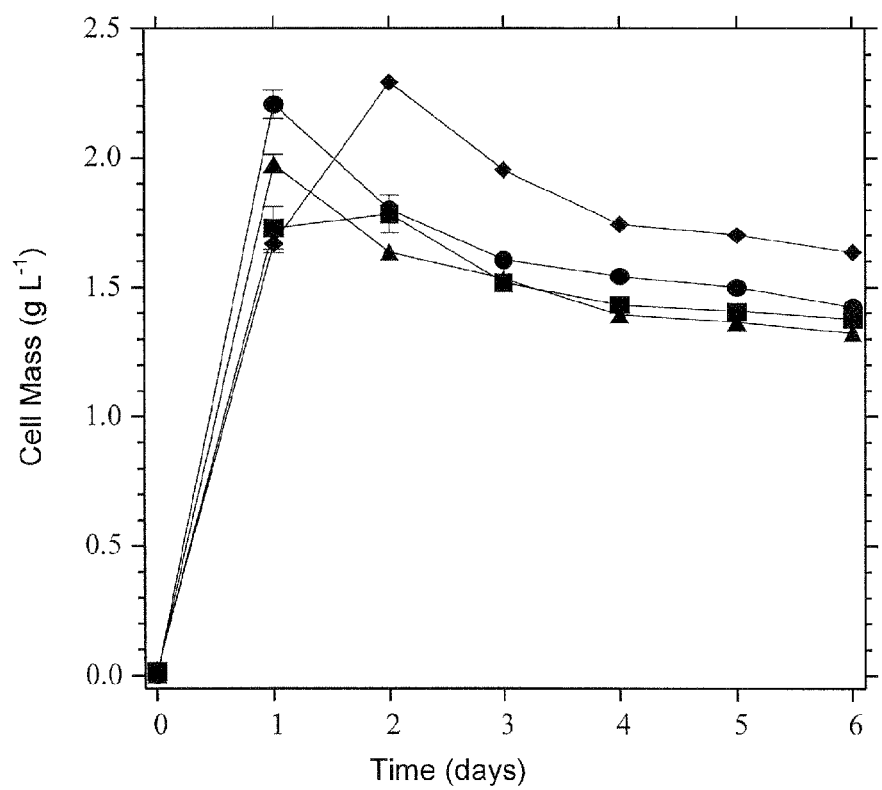

The D-(−)-lactate strain, SZ194, was re-engineered to produce primarily L-(+)-lactate by replacing the native ldhA gene encoding a D-(−)-lactate dehydrogenase with the ldhL gene from P. acidilactici encoding L-(+)-lactate dehydrogenase (Zhou et al., 2003a). The resulting strain, TG102 produced primarily L-(+)-lactate and was serially transferred in minimal medium containing 5% (w/v) glucose, 10% (w/v) glucose and 10% (w/v) glucose containing 1 mM betaine to select for improved growth and productivity. After 24 days, one clone was selected and designated TG103. Although lactate productivity improved due to an increase in glycolytic flux (FIGS. 10C and 10D; Table 9), L-(+)-lactate was contaminated with 5% D-(−)-lactate (Table 8). Since the Methylglyoxal Bypass has the potential to produce both chiral forms of lactate, mgsA was identified as the most likely source of chiral impurity. Absolute chiral purity was restored after deletion of mgsA. The resulting strain, TG105, produced only L-(+)-lactate (FIGS. 10 and 10D; Table 8). Further improvements were by co-selecting growth and productivity during serial transfers in mineral salts medium containing 10%-12% (w/v) glucose and 1 mM betaine (inoculum dilution of 1:100 to 1:350). TG106 and TG107 were isolated as intermediate strains after 10 and 22 transfers, respectively (FIGS. 10E and 10F). Strain TG108 was isolated after 99 days. All produced only L-(+)-lactate at high yields with minimum levels of co-products (Table 8). Volumetric productivities in 12% (w/v) glucose and cell yield increased during strain selection although specific productivity remained essentially constant (Table 9). Small increases in maximum volumetric productivity (most active 24-h period) were observed with higher inocula.

Strain TG108 was compared to other biocatalysts for L-(+)-lactate production (Table 10). The titer and yield for this strain were higher than those reported for other organisms. Other advantages include simple fermentation conditions and medium, and chiral purity.

Conclusions

High titers (>100 $gl^{-1}$ in 48 h) of chirally pure L-(+) and D-(−)-lactate (>99.9% chiral purity) can be readily produced by recombinant E. coli B in mineral salts medium supplemented with 1 mM betaine. Elimination of the Methylglyxal Bypass was essential to eliminate impurities in both the D-(+) and L-(−) enantiomers of lactate.

EXAMPLE 4

Construction of TG128 by Removal of all Foreign DNA from TG114

To facilitate commercial application of recombinant E. coli strains for lactate production, a further derivative of TG114 was constructed in which all extraneous DNA that had been left behind in the chromosome during previous genetic engineering was removed. DNA removed included scar regions containing the FRT recognition site for the flippase (recombinase) used to remove antibiotic markers, small fragments of DNA from Zymomonas mobilis, part of Klebsiella oxytoca casAB, and part of Erwinia chrysanthemi celY. These foreign DNA segments were completely eliminated leaving only native chromosomal DNA in which central regions of selected genes have been deleted to improve the production of lactate.

Strains, Plasmids, Media and Growth Conditions

E. coli strains, plasmids and primers used in this study a listed in Table 11. Strain TG114 was formerly constructed from a derivative of E. coli B (ATCC 11303) and served as a starting point for constructions (Grabar et al., 2006). During strain constructions, cultures were grown aerobically at 30° C., 37° C., or 39° C. in Luria broth (per liter: 10 g Difco tryptone, 5 g Difco yeast extract and 5 g sodium chloride) (Miller 1992) containing 2% (w/v) glucose or arabinose or 10% sucrose. Ampicillin (50 mg/L), chlorotetracycline (10 mg/L), or chloramphenicol (40 mg/L) were added as needed.

Cultures were maintained on plates containing NBS mineral salts medium (Causey et al., 2004) supplemented with 2% (w/v) glucose. MOPS buffer (100 mM, pH 7.4) was added to solid and liquid medium under conditions which lacked pH control (plates, tubes, shaken flasks). For fermentation tests, strains were grown without antibiotics at 37° C. in AM1 mineral salts medium (per liter: 2.63 g $(NH_4)_2HPO_4$, 0.87 g $NH_4H_2PO_4$, 0.37 g $MgSO_4.7H_2O$, 2.4 mg $FeCl_3$, 0.3 mg $CoCl_2.6H_2O$, 0.15 mg $CuCl_2$, 0.3 mg $ZnCl_2.4H_2O$, 0.3 mg $NaMoO_4$, 0.075 mg $H_3BO_3$, 0.075 mg $MnCl_2.4H_2O_2$, 1 mM betaine and 120 g/L glucose).

Genetic Methods

Manufacturer protocols and standard methods (Miller 1992, Sambrook and Russell 2001) were followed for cloning of genes (Invitrogen), DNA purification (Qiagen), restriction endonuclease digestion (New England Biolabs), DNA amplification (Stratagene and Invitrogen) and transformation. Methods for chromosomal deletions and integration have been described previously (Causey et al., 2004, Zhou et. al, 2003, Datsenko and Wanner 2000, Martinez-Morales et al., 1999). A description of the plasmids and the primers used are listed in Table 11.

Plasmid Constructions

Plasmid pLOI4411 was generated by designing primers that amplified within the frdABCD operon of E. coli B gDNA, 'frdA frdB frdC and frdD', and subsequent ligation into the Invitrogen cloning vector, pCR2.1-TOPO (Table 11). Plasmids pLOI4412, pLOI4413, pLOI4415 and pLOI4416 were constructed in a similar approach in order to clone the native genes of interest, ackA, adhE, focA-plfB and mgsA, respectively.

Figure 12A:
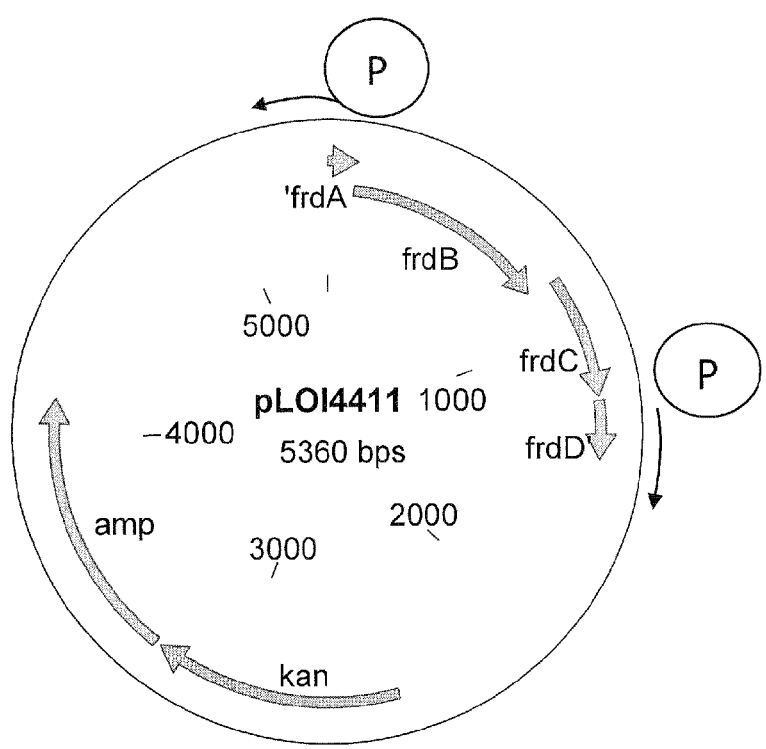
FIGS. 12A-C illustrate the production of pLOI4417. pLOI4417 was generated by performing PCR on pLOI4411 with a primer that annealed to the 3' end of frdA, extending upstream, and a primer that annealed within frdC, extending downstream (FIG. 12A). The resulting 4263 by PCR product was treated with restriction enzyme DpnI to digest the native pLOI4411 plasmid (FIG. 12B). Digested PCR products were subsequently self-ligated in order to generate the new plasmid, pLOI4417 (FIG. 12C).
Figure 12B:
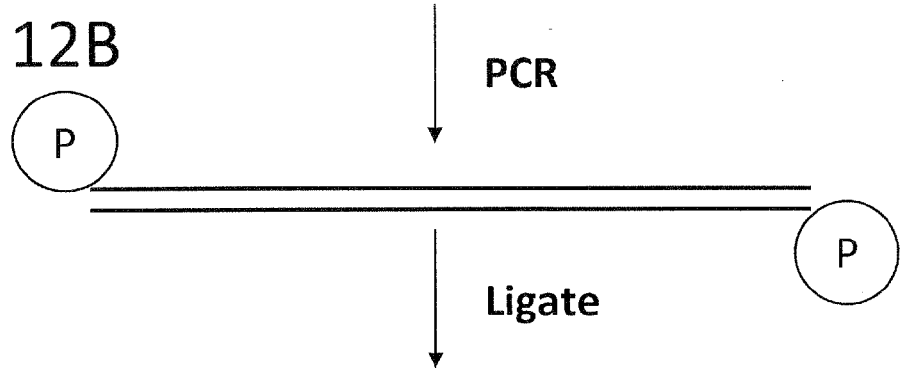
Figure 12C:
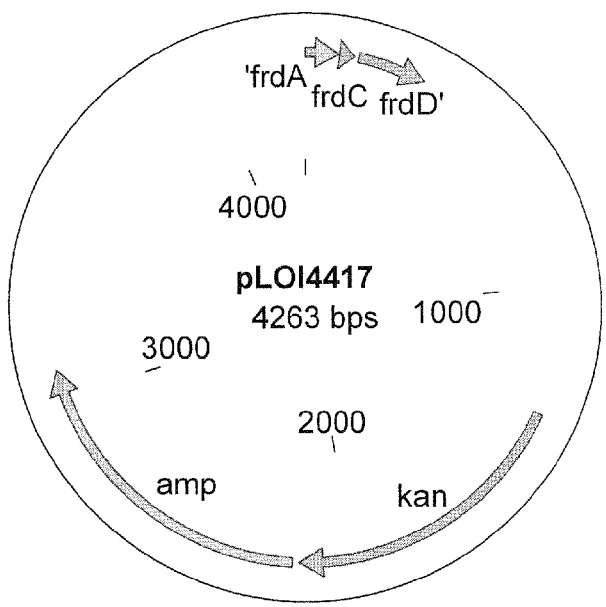

Plasmids encoding the seamless gene knockouts were generated using antisense primers. Antisense primers with 5' phosphate groups were designed to amplify the entire plasmid minus the gene region to be omitted (FIG. 12). For example, pLOI4417 was generated by performing PCR on pLOI4411 with a primer that annealed to the 3' end of frdA, extending upstream, and a primer that annealed to frdC, extending downstream. The resulting 4263 by PCR product was treated with restriction enzyme DpnI to digest the native pLOI4411 plasmid. Digested PCR products were subsequently self-ligated in order to generate the new plasmid, pLOI4417. Plasmids pLOI4418. pLOI4419, pLOI4421 and pLOI4422 were generated in a similar fashion using primer sets listed in Table 11. These plasmids served as a PCR template to amplify linear DNA that contained the desired deletion and was devoid of all heterologous sequence. This linear DNA was used to replace FRT scar regions, heterologous DNA, and sacB by homologous recombination (double cross-over event). In this way, seamless deletions of selected genes were made on the chromosome.

Removal of FRT Scar and Heterologous DNA from TG114

The ~85 by FLP recognition target (FRT) scars left behind by the one-step deletion method of Datsenko and Wanner (2000) were removed by a two-step approach. First, the FRT sites were individually targeted by a circular FRT-cat-sacB cassette resulting in a single cross-over integration of this cassette into an FRT scar on the chromosome (FRT-cat-sacB-FRT). Circular DNA containing the cat-sacB-FRT cassette was constructed as follows: 1. PCR amplification of the FRT-cat-sacB cassette using plasmid pLOI4151 as the template. The amplified cassette included flanking PstI sites; 2) Digestion with PstI followed by self-ligation to produce closed circles incapable of autonomous replication. This circular DNA was used for integration. Expression of the cat gene conferred chloramphenicol resistance and allowed direct selection of cells containing the integration.

In the second step, the sacB gene allowed a direct selection of cells in which the DNA region containing sacB has been removed by homologous recombination (double cross-over event). Cells expressing sacB in the presence of 10% sucrose (Ausubel et al., 2005; Lee et al., 2001) were killed and lysed by the intracellular production of polysaccharide. With this method, recombinants in which DNA had been inserted to replace sacB could be selected from large populations. In this example, integration of a linear DNA fragment via a double-crossover event resulted in a clean knockout strain containing only native DNA or native DNA with deletions, lacking all heterologous DNA. Native DNA sequence or native sequence containing a desired gene deletion was used in this second step to completely remove FRT scar regions and all heterologous DNA from strain TG114.

Following electroporation with the linear DNA fragment, the cells were incubated with shaking at 37° C. for 4 hours in 1 mL SOC medium. After the 4 hour outgrown, the cells were incubated for 16-20 hours in 50 mL LB with no salt (per liter: 10 g Difco tryptone, 5 g Difco yeast extract) supplemented with 10% (w/v) sucrose. Then the cells were struck onto salt-less LB agar plates supplemented with 5% sucrose. The majority of cells retaining the FRT-cat-sacB were not viable after prolonged periods in the presence of sucrose. Viable cells forming colonies were devoid of sacB, and scar regions.

This method was used sequentially to eliminate all 5 FRT scars present in TG114 and to restore the lac operon. Primers, plasmids, and strains used in this process are summarized in Table 11. The casAB genes integrated into lacA were also removed and replaced with wild type sequence in this region using a modification of this two-step method. Fragments of *Erwinia chrysanthemi* celY (and *Z. mobilis* DNA) integrated into frdA were removed during the construction of the seamless frdBC deletion. The resulting strain, TG128, is devoid of FRT scars and contains only native DNA sequence with deleted regions in the genes indicated in Table 11. A comparison of the original sequence in the region of gene deletions is shown for TG114 and TG128 (Table 12).

Restoration of Native lac Operon

TG114 contained segments of heterologous DNA (DNA fragments from *Zymononas mobilis, Klebsiella oxytoca* casAB, and part of *Erwinia chrysanthemi* celY) from prior constructions in the lacy, lacA region (Grabar et al., 2006). These were removed from TG120 to produce TG122 and are absent in subsequent derivatives of TG122. Primers for this construction are listed in Table 11. To accomplish this, the native lacZ' to cynX region was amplified from *E. coli* B and cloned into pCR2.1-TOPO to produce pLOI3956. To facilitate selection of recombinants, the central region of pLOI3956 (lacZ'-lacA') was replaced with a cassette containing cat and sacB genes as follows. With pLOI3956 as a template, antisense primers containing an NheI sites were used to amplify lacZ', pCR2.1, and cynX (omitting part of lacZ, lacy, lacA and part of cynX'). A second set of primers containing NheI sites was used to amplify a cat-sacB cassette from plasmid pEL04 (originally known as pK04, Ausubel et al., 2005 and Lee et al., 2001). After digestion with NheI, these PCR products were ligated to produce pLOI3957, a derivative of pCR2.1 that contains lacZ'-sacB-cat-cynX'. Using plasmid pLOI3957 as a template, the lacZ'-sacB-cat-cynX' region was amplified by PCR and integrated into TG120 with selection for chloramphenicol resistance to produce TG121. Using pLOI3956 as a template, the wild type lacZ'-lacY-lacA-cynX' region was amplified by PCR and integrated into TG121. Integrants containing the native sequence of the lacZYA operon were selected by the absence of sacB function during growth in the presence of sucrose. One of these was designated TG122. Strain TG122 was an intermediate strain during the construction of TG128.

Fermentations

Pre-inoculum was grown by inoculating a colony into a 250-ml flask containing 100 ml of NBS medium (Causey et al., 2004) with 2% (w/v) glucose and 100 mM MOPS (pH 7.4). After 16 h (37° C., 120 rpm), this pre-inoculum was diluted into 500-ml fermentation vessels containing 350 ml AF1 mineral salts media (12% sugar) to provide 33 mg dcw/L. After 24-h (37° C., 150 rpm, pH controlled at 7.0), the resulting culture was used to provide a starting inoculum of 33 mg dcw/L and incubated under the same conditions for 96 h. Samples were removed for analyses.

Analyses

Cell mass was estimated by measuring the optical density at 550 nm using a Bausch & Lomb Spectronic 70 spectrophotometer. Total organic acid production, primarily lactate, was estimated by KOH consumption used to maintain pH 7.0. Acidic products and chiral purity were analyzed at the end of fermentation by high-performance liquid chromatography. Estimates of organic acid by base consumption were consistently lower than measurements of lactate by HPLC, presumably due to mineral metabolism.

Fermentation of Glucose by TG128

Strain TG114 was subjected to intensive genetic manipulation to remove FRT scars and other extraneous DNA. The resulting organism, strain TG128, contains only native, wild-type DNA sequence and seamless deletions of genes to eliminate unwanted fermentation products. Fermentation performance of this strain was essentially equivalent to that for TG114, lactate yields of 96-98% of the maximum theoretical yield (Table 13).

Selection of Thermotolerant Mutants for Lactate Production by Metabolic Evolution Metabolic evolution was used to select strains capable of efficient lactate production at elevated temperatures. Cells from pH-controlled fermentations were serially transferred at 24 h intervals to facilitate metabolic evolution though competitive, growth-based selection. At each transfer, inocula were diluted (1/100 to 1/350) into pre-warmed, fresh media. Incubation temperature was increased by a fraction of a degree as growth permitted to facilitate the isolation of thermotolerant strains. Strain TG128 ferments optimally at 37° C. Mutants were obtained by incrementally increasing the incubation temperature during successive transfers. With this approach, new strains were selected from TG128 that are now capable of efficient fermentation at 39° C. (strain TG129) and 43° C. (strain TG130). Yields for both thermotolerant strains at elevated temperature were equivalent to TG114 at 37° C. (Table 13).

Fermentation of Glucose by TG128

Strain TG114 was subjected to intensive genetic manipulation to remove FRT scars and other extraneous DNA. The resulting organism, strain TG128, contains only native, wild-type DNA sequence and seamless deletions of genes to eliminate unwanted fermentation products. Fermentation performance of this strain was essentially equivalent to that for TG114, lactate yields of 96-98% of the maximum theoretical yield (Table 13).

Selection of Thermotolerant Mutants for Lactate Production

Metabolic evolution was used to select strains capable of efficient lactate production at elevated temperatures. Serial transfers into fermentors in which temperature was increased by a fraction of a degree allowed the isolation of TG129 which ferments optimally at 39° C. and TG130 which ferments optimally at 43° C. Yields for both at elevated temperature were equivalent to TG114 at 37° C. (Table 13).

TABLE 7

E. coli strains, plasmids and primers used in this study

| Plasmid or Strain | Relevant Characteristics | Sources |
|---|---|---|
| Strains | | |
| SZ194 | pflB frd adhE ackA | Zhou et al. (2006) |
| TG102 | SZ194, ΔldhA::ldhL-FRT | This study |
| TG103 | Mutant of TG102 with improved growth and ldhL activity | This study |
| TG105 | TG103, ΔmgsA::FRT | This study |
| TG106, TG107 and TG108 | Mutants of TG105 with improved growth and ldhL activity | This study |
| TG112 | SZ194, ΔmgsA::FRT | This study |
| TG113 and TG114 | Mutants of TG112 with improved growth and ldhA activity | This study |
| Plasmids | | |
| pKD46 | bla γ β exo (Red recombinase), temperature conditional pSC101 replicon | Datsenko and Wanner (2000) |
| pFT-A | bla flp temperature conditional pSC101 replicon | Posfai et al. (1997) |
| pKD4 | bla kan; R6K ori; FRT-kan-FRT cassette | Datsenko and Wanner (2000) |
| PLO12398 | kan; ldhA'-ldhL-FRT-tet-FRT-'ldhA; R6K ori | Zhou et al. (2003) |
| Primers | | |
| Sense primer for mgsA deletion | Atgtacattatggaactgacgactcgcactttacctgcgcgg aaacatatgtgtaggctggagctgcttc (SEQ ID NO: 7) | This study |
| Antisense primer for mgsA deletion | Ttacttcagacggtccgcgagataacgctgataatcgggga tcagaatatcatatgaatatcctccttag (SEQ ID NO: 8) | This study |

TABLE 8

Products from glucose fermentations

| Strain | Conditions[a] | Lactate mmol l[-1] | Yield (%)[b] | Chiral Purity (%) | Succinate | Acetate | Ethanol |
|---|---|---|---|---|---|---|---|
| SZ194 | NBS, pH 7.5 + betaine | 1228 ± 31 | 95 | 95 | <1 | <1 | <1 |
| TG102 | NBS 5% glucose | 555 ± 6 | 99 | 99.5 | <1 | <1 | <1 |
| TG102 | NBS 10% glucose | 697 ± 13 | 96 | 99.5 | <1 | <1 | <1 |
| TG102 | NBS 10% glucose + betaine | 1025 ± 18 | 94 | 95 | <1 | <1 | <1 |
| TG103 | NBS 10% glucose + betaine | 1080 ± 15 | 95 | 95 | <1 | <1 | <1 |
| TG105 | NBS + betaine | 969 ± 20 | 95 | >99.9 | <1 | <1 | <1 |
| TG106 | NBS + betaine | 1055 ± 19 | 95 | >99.9 | <1 | <1 | <1 |
| TG107 | NBS + betaine | 1135 ± 18 | 96 | >99.9 | <1 | <1 | <1 |
| TG108 | NBS + betaine | 1287 ± 15 | 98 | >99.9 | <1 | <1 | <1 |
| TG112 | NBS 10% glucose + betaine | 926 ± 13 | 95 | >99.9 | <1 | <1 | <1 |
| TG113 | NBS + betaine | 1068 ± 32 | 95 | >99.9 | <1 | <1 | <1 |
| TG114 | NBS + betaine | 1314 ± 48 | 98 | >99.9 | <1 | <1 | <1 |

[a]NBS mineral salts medium containing 12% (w/v) glucose (pH 7.0) unless specified otherwise. Where indicated, 1 mM betaine was also added. Bold strains produce D-(−)-lactate. Underlined strains produce L-(+)-lactate.
[b]Yields are based on metabolized sugar assuming a maximum theoretical yield of 2 moles of lactate per mole of hexose (equal weight conversion).

TABLE 9

Lactate productivity by engineered *E. coli* B

| Strain[a] | Lactate titer (mmol l[-1]) | Cell yield (g l[-1]) | Volumetric[f] productivity (mmol l[-1]h[-1]) | Specific[f] productivity (mmol g[-1]h[-1]) | Volumetric[f] productivity (g l[-1]h[-1]) |
|---|---|---|---|---|---|
| SZ194[b] | 1228 | 1.70 | 23.3 | 13.7 | 2.10 |
| TG103[e] | 1083 | 2.12 | 30.1 | 14.2 | 2.71 |
| TG105[e] | 969 | 1.84 | 21.1 | 11.5 | 1.90 |
| TG106 | 1055 | 1.98 | 24.1 | 12.1 | 2.17 |
| TG107 | 1135 | 2.21 | 26.7 | 12.1 | 2.40 |
| TG108 | 1287 | 2.29 | 26.2 | 11.4 | 2.29 |
| TG108[c] | 1273 | 2.15 | 26.4 | 12.3 | 2.37 |
| TG108[d] | 1268 | 2.36 | 30.0 | 12.7 | 2.70 |
| TG112[e] | 926 | 1.84 | 20.4 | 11.1 | 1.84 |
| TG113 | 1068 | 1.90 | 21.3 | 11.2 | 1.92 |
| TG114 | 1314 | 2.31 | 32.2 | 13.9 | 2.88 |
| TG114[c] | 1204 | 2.05 | 33.9 | 16.6 | 3.05 |
| TG114[d] | 1202 | 2.16 | 36.1 | 16.7 | 3.25 |

[a]Mineral salts (NBS) containing 12% (w/v) glucose, 1 mM betaine, controlled at pH 7.0 (unless otherwise specified). Bold strains produce D-(−)-lactate. Underlined strains produce L-(+)-lactate.
[b]pH controlled at 7.5.
[c]5% inoculum.
[d]10% inoculum.
[e]10% glucose.
[f]Averaged values for the most productive 24-h period.

TABLE 10

Chiral lactate production from glucose by bacteria, yeasts and fungi

| Organisms | Media, substrate and process conditions | Lactate (g l[-1]) | Yield (%) | Volumetric Productivity (g l[-1]h[-1]) | Isomer and Purity | Reference |
|---|---|---|---|---|---|---|
| *E. coli* TG114 | salts, 1 mM betaine batch, glucose, 120 g l[-1] | 118 | 98 | 2.88 | D-(−) >99.9% | This study |
| *E. coli* JP203 | rich medium (LB) two-stage, fed batch glucose, 115 g l[-1] | 62 | 54 | 1.09 | D-(−) Not reported | Chang et al. 1999 |

TABLE 10-continued

Chiral lactate production from glucose by bacteria, yeasts and fungi

| Organisms | Media, substrate and process conditions | Lactate (gl$^{-1}$) | Yield (%) | Volumetric Productivity (gl$^{-1}$h$^{-1}$) | Isomer and Purity | Reference |
|---|---|---|---|---|---|---|
| Lactobacillus delbrueckii mutant DP3 | yeast extract, fed-batch glucose, 210 gl$^{-1}$ | 117 | 56 | 6.5 | D-(−) Not reported | Demirci et al. 1992 |
| Kluyveromyces marxianus CD590 | rich medium (YPD), microaerobic glucose, 100 g l$^{-1}$ | 81 | 81 | 1.5 | D-(−) 99% | Rajgarhia et al. 2004 |
| E. coli TG108 | salts, 1 mM betaine batch, glucose, 120 gl$^{-1}$ | 116 | 98 | 2.3 | L-(+) >99.9% | This study |
| E. coli JP204 (pLS65) | rich medium (LB), two-stage, fed-batch glucose, 155 g l$^{-1}$ | 47 | 30 | 0.7 | L-(+) Not reported | Chang et al. 1999 |
| E. coli FBR11 (pVALDH1) | rich medium (LB), simple batch, glucose, 100 g l$^{-1}$ | 73 | 73 | 2.3 | L-(+) Not reported | Dien et al. 2001 |
| Kluyveromyces lactis BM3-12D (pLAZ10) | yeast extract and vitamins fed-batch, aeration glucose, 110 g l$^{-1}$ | 60 | 55 | Not reported | L-(+) Not reported | Bianchi et al. 2001 |
| Kluyveromyces lactis PMI/C1 (pEPL2) | yeast extract and corn steep liquor, fed-batch with aeration, glucose, 200 g l$^{-1}$ | 109 | 55 | Not reported | L-(+) Not reported | Porro et al. 1999 |
| Saccharomyces cerevisiae RWB850-2 | vitamin-supplemented, two-stage glucose, 18 g l$^{-1}$ | 12 | 67 | Not reported | L-(+) Not reported | Van Maris et al. 2004b |
| Saccharomyces cerevisiae OC2T T165R | yeast extract, cane juice sugars, 200 gl$^{-1}$ | 122 | 61 | Not reported | L-(+) 99.9% | Saitoh et al. 2005 |
| Saccharomyces cerevisiae RWB876 | vitamin-supplement, simple batch glucose, 74 gl$^{-1}$ | 61 | 82 | Not reported | L-(+) Not reported | Liu et al. 2005 |
| Lactobacillus helveticus GRL89 | yeast extract simple batch lactose, 81 g l$^{-1}$ | 75 | 92 | 3.2 | L-(+) Not reported | Kyla-Nikkila et al. 2000 |
| Lactabacillus sp. NRRL B-30574 | yeast extract simple batch glucose, 130 g l$^{-1}$ | 103 | 79 | Not reported | L-(+) 100% | Eddington et al. 2004 |
| Rhizopus oryzae ADM 34.31 | urea and rich medium air-lift batch glucose, 120 g l$^{-1}$ | 109 | 89 | 1.3 | L-(+) Not reported | Liaw 2003 |

TABLE 11

E. coli strains, plasmids and primers used in this study

| Plasmid or Strain | Relevant Characteristics | Sources |
|---|---|---|
| TG114 | ΔfocA-pflB::FRT, ΔadhE::FRT, ΔackA::FRT, frdA::E. chrysanthemi celY, ΔfrdBC::FRT, lacA::K. oxytoca cas AB, ΔmgsA::FRT | Grabar, et al. 2006 |
| TG117 | TG114, ΔfrdBC::FRT-cat-sacB-FRT | This study |
| TG118 | ΔfocA-pflB::FRT, ΔadhE::FRT, ΔackA::FRT, ΔfrdBC, lacA::K. oxytoca cas AB, ΔmgsA::FRT | This study |
| TG119 | TG118, ΔackA::FRT-cat-sacB-FRT | This study |
| TG120 | ΔfocA-pflB::FRT, ΔadhE::FRT, ΔackA, ΔfrdBC, lacA::K. oxytoca cas AB, ΔmgsA::FRT | This study |
| TG121 | TG120, ΔlacZ-cynX(lacZ'-sacB-cat-cynX') | This study |
| TG122 | ΔfocA-pflB::FRT, ΔadhE::FRT, ΔackA, ΔfrdBC, ΔmgsA::FRT | This study |
| TG123 | TG122, ΔmgsA::FRT-cat-sacB-FRT | This study |

TABLE 11-continued

*E. coli* strains, plasmids and primers used in this study

| | Relevant Characteristics | Sources |
|---|---|---|
| TG124 | ΔfocA-pflB::FRT, ΔadhE::FRT, ΔackA, ΔΔfrdBC, ΔmgsA | This study |
| TG125 | TG124, ΔfocA-pflB:FRT-cat-sacB-FRT | This study |
| TG126 | ΔfocA-pflB, ΔadhE::FRT, ΔackA, ΔfrdBC, ΔmgsA | This study |
| TG127 | TG126, ΔadhE::FRT-cat-sacB-FRT | This study |
| TG128 | ΔfocA-pflB, ΔadhE, ΔackA, ΔfrdBC, ΔmgsA | This study |
| TG129 | TG128, improved growth at 39° C. | This study |
| TG130 | TG129, improved growth at 43° C. | This study |
| Plasmids | | |
| pKD46 | bla γ β exo (Red recombinase), temperature conditional pSC101 replicon | Datsenko and Wanner (2000) |
| pFT-A | bla flp temperature conditional pSC101 replicon | Posfai et al. (1997) |
| pEL04 | cat sacB | Lee et al. (2001); Ausubel et al. (2005 |
| pLOI4151 | FRT cat sacB | This study |
| PLOI3956 | 'lacZ' lacY lacA cynX' TOPO cloned | This study |
| PLOI3957 | 'lacZ' sacB cat cynX' | This study |
| pLOI4411 | 'frdA frdB frdC frdD' TOPO cloned | This study |
| pLOI4412 | 'ackA' TOPO cloned | This study |
| pLOI4413 | ychE' adhE ychG' TOPO cloned | This study |
| pLOI4415 | focA-pflB TOPO cloned | This study |
| pLOI4416 | 'yccT mgsA' helD TOPO cloned | This study |
| pLOI4417 | pLOI4411, ΔfrdBC | This study |
| pLOI4418 | pLOI4412, ΔackA | This study |
| pLOI4419 | pLOI4413, ΔadhE | This study |
| pLOI4421 | pLOI4415, ΔfocA-pflB | This study |
| pLOI4422 | pLOI4416, ΔmgsA | This study |
| Primers | | |
| Sense primer for amplification of FRT-cat-sacB | tgtgctgcaaggcgattaag (SEQ ID NO: 9) | This study |
| Antisense primer for amplification of FRT-cat-sacB | ttcgatcacggcacgatcat (SEQ ID NO: 10) | This study |
| Sense primer for amplification of cat-sacB with 5' NheI site | ttagctagcatgtgacggaag (SEQ ID NO: 11) | This study |
| Antisense primer for amplification of cat-sacB with 5' NheI site | ccgctagcatcaaagggaaaa (SEQ ID NO: 12) | This study |

TABLE 11-continued

E. coli strains, plasmids and primers used in this study

| | Relevant Characteristics | Sources |
|---|---|---|
| Sense primer for cloning frdABCD | ctggagtacagcgacgtgaagat (SEQ ID NO: 13) | This study |
| Antisense primer for cloning frdABCD | cagaacgcgctcgtagctca (SEQ ID NO: 14) | This study |
| Sense primer for cloning ackA | gaactgcggtagttcttcactg (SEQ ID NO: 15) | This study |
| Antisense primer for cloning ackA | gcgtcttgcgcgataaccag (SEQ ID NO: 16) | This study |
| Sense primer for cloning lacZ-cynX | gaagtgaccagcgaatacct (SEQ ID NO: 17) | This study |
| Antisense primer for cloning lacZ-cynX | ggtgatgccttcggtgatta (SEQ ID NO: 18) | This study |
| Sense primer for cloning mgsA | gctattccaccgcagtctca (SEQ ID NO: 19) | This study |
| Antisense primer for cloning mgsA | ttatggaagaggcgctactgc (SEQ ID NO: 20) | This study |
| Sense primer for cloning focA-pflB | agatcgccagccgctgcaat (SEQ ID NO: 21) | This study |
| Antisense primer for cloning focA-pflB | aaccgttggtgtccagacag (SEQ ID NO: 22) | This study |
| Sense primer for cloning adhE | ccgctgtctgataactggtc (SEQ ID NO: 23) | This study |
| Antisense primer for cloning adhE | gcataagcggatggtcactg (SEQ ID NO: 24) | This study |
| Sense primer for deleting frdBC | P-gtggttgccaccatcgtaat (SEQ ID NO: 25) | This study |
| Antisense primer for deleting frdBC | P-cgccttctccttcttattgg (SEQ ID NO: 26) | This study |
| Sense primer for deleting ackA | P-ctggacgctgttgtattcactg (SEQ ID NO: 27) | This study |
| Antisense primer for deleting ackA | P-gttgagcgcttcgctgtgag (SEQ ID NO: 28) | This study |
| lacZ antisense primer with 5' NheI site | acgctagctctgacaatggca (SEQ ID NO: 29) | This study |
| cynX antisense primer with 5' NheI site | acgctagcattgccgctgata (SEQ ID NO: 30) | This study |
| Sense primer for deleting mgsA | P-agcgttatctcgcggaccgt (SEQ ID NO: 31) | This study |
| Antisense primer for deleting mgsA | P-aagtgcgagtcgtcagttcc (SEQ ID NO: 32) | This study |
| Sense primer for deleting focA-pflB | P-gcagcaggacgttattactc (SEQ ID NO: 33) | This study |
| Antisense primer for deleting focA-pflB | P-gcctacattgcgtaggctatt (SEQ ID NO: 34) | This study |
| Sense primer for deleting adhE | P-gctgctccggctaaagctga (SEQ ID NO: 35) | This study |
| Antisense primer for deleting adhE | P-acgctctacgagtgcgttaag (SEQ ID NO: 36) | This study |

TABLE 12

Partial Sequence of Region of Deletions

| Strain/gene | Partial Sequence [a] | Foreign DNA (bp) |
|---|---|---|
| TG114 frdABC | GCCAATAACAAGGAGAAGGCGAATGGATCTGATAGATTGTTTTTAAAAAATTGTTTTTGG CTCTCGACAATTTCCAACAACATCCCTATATTTATCCCATCTAAAAGGCCTCTACCTTGA AAAGGCGAGGCTACCTGCTTGTTTTTCGGGACAGGATCCTCTAGAGTCAACCTGCTTGTT ACTCGTGATCCCATTCACAAGGGCGAATTAATTCCCCCTTCTGTTCCGTTACCAACACTG *AGCCGGACAGTAATGGGAAAGCCAAGTGTAGGCTGGAGCTGCTTCGAAGTTCCTATACTT TCTAGAGAATAGGAACTTCGGAATAGGAACTAAGGAGGATATTCATATG*GTGGTTGCCAC CATCGTAATCCTGTT [b] (SEQ ID NO: 37) | 322 |
| TG128 frdABC | GCCAATAAGAAGGAGAAGGCG-GTGGTTGCCACCATCGTAATCCTGTT [c] (SEQ ID NO: 38) | 0 |
| TG114 ackA | CTCACAGCGAAGCGCTCAACTTTATCGTTAATACTATTCTGGCACAAAAACCAGAACTGT CTGCGCAGCTGACTGCTATCGGTCACCGTATCGTACACGGCGGCGAAAAGTATACCAGCT CCGTAGTGATCGATGAGTCTGTTATTCAGGGTATCAAAGATGCAGCTTCTTTTGCACCGC TGCACAACCCGGCTCACCTGATCGGTATCGAAGAAGCTCTGAAATCTTTCCCACAGCTGA AAGACAAAAACGTTGCTGTATTTGACACCGCGTTCCACCAGACTATGCCGGAAGAGTCTT ACCTCTACGCCCTGCCTTACAACCTGTACAAAGAGCACGGCATCCGTCGTTACGGCGCGC ACGGCACCAGCCACTTCTATGTAACCCAGGAAGCGGCAAAAATGCTGAACAAACCGGTAG AAGAACTGAACATCATCACCTGCCACCTGGGCAACGGTGGTTCCGTTTCTGCTATCCGCA ACGGTAAATGCGTTGACACCTCTATGGGCCTGACCCCGCTGGAAGGTCTGGTCATGGGTA CCCCTTCTGGTGAT*GGGGAGCTTGTCGACAATTCGAAGTTCCTATACTTTCTAGAGAATA GGAACTTCGGATCAATTCATCGGGCGCGGGAATTCGAGCTCGGTACCC*ATCGATCCGGCG ATCATCTTCCACCTGCACGACACCCTGGGCATGAGCGTTGACGCAATCAACAAACTGCTG ACCAAAGAGTCTGGCCTGCTGGGTCTGACCGAAGTGACCAGCGACTGCCGCTATGTTGAA GACAACTACGCGACGAAAGAAGACGCGAAGCGCGCAATGGACGTTTACTGCCACCGCCTG GCGAAATACATCGGTCCCTACACTGCGCTGATGGATGGTCGTCTGGACGCTGTTGTATTC (SEQ ID NO: 39) | 94 |
| TG128 ackA | CTCACAGCGAAGCGCTCAA-CTGGACGCTGTTGTATTC (SEQ ID NO: 40) | 0 |
| TG114 mgsA | ATGGAACTGACGACTCGCACTTTACCTGCGCGGAAACATAT*GTGTAGGCTGGAGCTGCTT CGAAGTTCCTATACTTTCTAGAGAATAGGAACTTCGGAATAGGAACTAAGGAGGATATTC ATATGA*TATTCTGATCCCCGATTATCAGCGTTATCTCGCGGACCGTCTGA (SEQ ID NO: 41) | 85 |
| TG128 mgsA | ATGGAACTGACGACTCGCACTT-AGCGTTATCTCGCGGACCGTCTGA (SEQ ID NO: 42) | 0 |
| TG114 focA-pflB | ATAGCCTACGCAATGTAGGCTTAATGATTAGTCTGAGTTATATTACGGGGCGTTTTTTTA ATGCCCCGCTTTACATATATTTGCATTAATAAAATAATTGTAATTATAAGGTTAAATATC GGTAATTTGTATTTAATAAATACGATCGATATTGTTACTTTATTCGCCTGATGCTCCCTT TTAATTAACTGTTTTAGCGGAGGATGCGGAAAAAATTCAACTCATTTGTTAATTTTTAAA ATTTATTTTTATTTGGATAATCAAATATTTACTCCGTATTTCCATAAAAACCATGCCAGT TACGGGCCTA*TAAGTGTAGGCTGGAGCTGCTTCGAAGTTCCTATACTTTCTAGAAATAG GAACTTCGGAATAGGAACTAAGGAGGATATTCATAT*GAGAACAGCAGCAGGACGTTAT (SEQ ID NO: 43) | 85 |
| TG128 focA-pflB | ATAGCCTACGCAATGTAGGC-GCAGCAGGACGTTAT (SEQ ID NO: 44) | 0 |
| TG114 adhE | AACGCACTCGTAGAGCGT*GTGTAGGCTGGAGCTGCTTCGAAGTTCCTATACTTTCTAGAG AATAGGAACTTCGGAATAGGAACTAAGGAGGATATTCATATG*GCTGCTCCGGCTAAAGCT (SEQ ID NO: 45) | 84 |
| TG128 adhE | AACGCACTCGTAGAGCGT-GCTGCTCCGGCTAAAGCT (SEQ ID NO: 46) | 0 |

[a] Shown in bold are partial sequences of the 5' and 3' region of the gene(s), in italics is the FRT scar and underlined is the region deleted in strain TG128.
[b] This region also contained partial sequence from a *Z. mobilis* promoter as well as partial sequence from *E. chrysanthemi* celY gene (shown in underlined regular type).
[c] The dash indicates the region of the deletion.

TABLE 13

Products from glucose fermentations

| Strain | Conditions[a] | Lactate | | | Co-products (mmol l$^{-1}$) | | |
| --- | --- | --- | --- | --- | --- | --- | --- |
| | | mmol l$^{-1}$ | Yield (%)[b] | Chiral Purity (%) | Succinate | Acetate | Ethanol |
| TG114 | AM1, 37° C. | 1314 ± 48 | 98 | >99.9 | <1 | <1 | <1 |
| TG128 | AM1, 37° C. | 1157 ± 37 | 96 | >99.9 | <1 | <1 | <1 |
| TG128 | AM1, 39° C. | 865 ± 12 | 95 | >99.9 | <1 | <1 | <1 |
| TG128 | AM1, 43° C. | 343 ± 68 | 95 | >99.9 | <1 | <1 | <1 |
| TG129 | AM1, 39° C. | 1063 ± 26 | 96 | >99.9 | <1 | <1 | <1 |
| TG129 | AM1, 43° C. | 934 ± 18 | 94 | >99.9 | <1 | <1 | <1 |
| TG130 | AM1, 43° C. | 1149 ± 49 | 97 | >99.9 | <1 | <1 | <1 |

[a]Mineral salts (NBS) containing 12% (w/v) glucose, 1 mM betaine, controlled at pH 7.0.
[b]Yield are based on metabolized sugar assuming a maximum theoretical yield of 2 moles of lactate per mole of hexose (equal weight conversion).

All patents, patent applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

U.S. Pat. No. 4,963,486
U.S. Published Patent Application No. 20040005677
U.S. Published Patent Application No. 20030003553
U.S. Published Patent Application No. 20050112737
U.S. Published Patent Application No. 20040029256
WO 99/14335
Adachi et al. (1998) "Modification of metabolic pathways of *Saccharomyces cerevisiae* by the expression of lactate dehydrogenase and deletion of pyruvate decarboxylase genes for the lactic acid fermentation at low pH value" *J. Ferment. Bioeng.* 86:284-289.
Agrawal, A. K. (2003) "Advances in the production of poly (lactic acid) fibers. A review." *J. Macromolec. Science-Polymer Rev.,* 4:479-503.
Arntzen, C. E., Dale, B. E. (1999) *Biobased industrial products, priorities for research and commercialization,* National Academy Press, Washington, D.C.
Ausubel, F. M. et al. (1995) *Current Protocols in Molecular Biology,* John Wiley & Sons, Inc.
Ausubel, F. M., R. Brent, R. E. Klingston, D. D. Moore, J. G. Deidman, J. A. Smith and K. Struhl (eds.) (2005) *Current protocols in molecular biology.* John Wiley & Sons, Inc. New York, N.Y.
Axe, D. D. and J. E. Bailey (1995) "Transport of lactate and acetate through the energized cytoplasmic membrane of *Escherichia coli*" Biotechnol. Bioeng. 47:8-19.
Badia, J., Gimenez, R., Baldoma, L., Barnes, E., Fessner, W. D., Aguilar, J. (1991) "L-lyxose metabolism employs the L-rhamnose pathway in mutant-cells of *Escherichia coli*-adapted to grow on xylose" *J. Bacteriol.* 173:5144-5150.
Bianchi, M. M., Brambilla, L., Protani, F., Liu, C., Lievense, Porro, D. (2001) "Efficient homolactic fermentation by *Kluveromyces lactis* strains defective in pyruvate utilization and transformed with heterologous LDH gene" *Appl. Environ. Microbiol.* 67:5621-5625.
Causey, T. B. et al. (2004) "Engineering *Escherichia coli* for efficient conversion of glucose to pyruvate" *Proc. Natl. Acad. Sci. USA* 101:2235-2240.
Chang, D. E. et al. (1999) "Homofermentative production of D-(−) or L-(+) lactate in metabolically engineered *Echerichia coli* RR1" *Appl Environ Microbiol* 65:1384-1389.
Chotani, G. et al. (2000) "The commercial production of chemicals using pathway engineering" *Biochim. Biophys. Acta* 1543:434-455.
Datsenko, K. A., Wanner, B. L. (2000) "One-step inactivation of chromosomal genes in *Escherichia coli* K-12 using PCR products" *Proc. Natl. Acad. Sci. USA* 97:6640-6645.
Datta, R. et al. (1995) "Technological and economic potential of poly(lactic acid) and lactic acid derivatives" *FEMS Microbiol. Rev.* 16:221-231.
Demirci, A. and A. L. Pometto (1992) "Enhanced production of D-(−)-lactic acid by mutants of *Lactobacillus delbrueckii* ATCC9649" *J. Ind. Microbiol. Biotechnol.* 11:23-28.
Dien, B. S. et al. (2001) "Recombinant *Escherichia coli* engineered for production of L-lactic acid from hexose and pentose sugars" *J Ind. Microbiol. Biotechnol.* 27:259-264.
Grabar, T. B. et al. (2006) "Methylglyoxal bypass identified as source of chiral contamination in L(+) and D(−) lactate fermentations by recombinant *Escherichia coli*" *Biotechnology Letters,* in publication.
Hofvendahl, K., and Hahn-Hagerdal, B. (2000) "Factors affecting fermentative lactic acid production from renewable resources" *Enzy. Microbiol. Technol* 26:87-107.
Konings, W. N. (2002) "The cell membrane and the struggle for life of lactic acid bacteria" *Antonie van Leeuwenhoek* 82:3-27.
Kyla-Nikkila, K. et al. (2000) "Metabolic engineering of *Lactobacillus helveticus* CNR32 for production of pure L-(+)-lactic acid" *Appl. Environ. Microbiol.* 66:3835-3841.
Lee, E-C., Yu, K., Martinez de Velasco, J., Tessarollo, L., Swing, D. A., Court, D. L., Jenkins, N. A., and Copeland, N. G. (2001) "A highly efficient *Escherichia coli*-based chromosome engineering system adapted for recombinogenic targeting and subcloning of BAC DNA" *Genomics* 73: 56-65.
Maniatis, T. et al. (1989) *Molecular Cloning: A Laboratory Manual,* Cold Springs Harbor Laboratory.
Martinez-Morales, F. et al. (1999) "Chromosomal integration of heterologous DNA in *Escherichia coli* with precise removal of markers and replicons during construction" *J. Bacteriol.,* 181:7143-7148.

Michels, P. A. M. et al. (1979) "Generation of an electrochemical proton gradient in bacteria by the excretion of metabolic end products" *FEMS Microbial. Lett.* 5:357-364.

Miller, J. H. (1992) *A short course in bacterial genetics: A laboratory manual and handbook for Escherichia coli and related bacteria*, Cold Spring Harbor Press.

Moniruzzaman, M. et al. (1997) "Isolation and molecular characterization of high-performance cellobiose-fermenting spontaneous mutants of ethanologenic *Escherichia coli* K011 containing the *Klebsiella oxytoca* casAB operon" *Appl. Environ. Microbiol.* 63:4633-4637.

Narayanan et al. (2004) "L-(+) lactic acid fermentation and its product polymerization," *Elect. J. Beiotechnol.* 7:167-179.

Ohara, H. et al. (2001) "Development of industrial production of high molecular weight poly-L-lactate from renewable resources" *Nippon Kagaku Kaishi* 6:323-331.

Ohta, K. et al. (1991) "Genetic improvement of *Escherichia coli* for ethanol production by chromosomal integration of *Zymomonas mobilis* genes encoding pyruvate decarboxylase and alcohol dehydrogenase II" *Appl Environ Microbiol.* 57:893-900.

Poolman, B. (2002) "Transporters and their roles in LAB cell physiology" *Antonie van Leeuwenhoek* 82:147-164.

Porro, D. et al. (1999) "Replacement of a metabolic pathway for large-scale production of lactic acid from engineered yeasts" *Appl. Environ. Microbiol.* 65:4211-4215.

Posfai, G., Koob, M. D., Kirkpatrick, H. A., Blattner, F. C. (1997) "Versatile insertion plasmids for targeted genome manipulations in bacteria: Isolation, deletion, and rescue of the pathogenicity island LEE of the *Escherichia coli* O157:H7 genome" *J. Bacteriol.* 179:4426-4428.

Purvis, J. E. et al. (2005) "Enhanced trehalose production improves growth of *Escherichia coli* under osmotic stress" *Appl. Environ. Microbiol.* 71:3761-3769.

Saitoh, S. et al. (2005) "Genetically engineered wine yeast produces a high concentration of L-lactic acid of extremely high optical purity" *Appl. Environ. Microbiol.* 71:2789-2792.

Sambrook, J. et al. (1989) *Molecular Cloning: A Laboratory Manual, Second Edition*, Cold Spring Harbor Laboratory Press.

Sambrook, J. and Russell, D. W. (2001) *Molecular cloning: A laboratory manual*, Cold Spring Harbor Press.

Shukla, V. B. et al. (2004) "Production of D-(−)-lactate from sucrose and molasses," *Biotechnol Lett.*, 26:689-693.

van Maris, A. J. A. et al. (2004a) "Microbial export of lactic and 3-hydroxypropanoic acid: implications for industrial fermentation processes" *Metabolic Engineering* 6:245-255.

van Maris, A. J. A. et al. (2004b) "Homofermentative lactate production cannot sustain anaerobic growth of engineered *Saccharomyces cerevisiae*: possible consequence of energy-dependent lactate export" *Appl. Environ. Microbiol.* 70(5):2898-2905.

Warnecke, T. and R. T. Gill (2005) "Organic acid toxicity, tolerance, and production of *Escherichia coli* biorefining applications" *Microbial Cell Factories* 4:25.

Zhou S., Ingram L. O. (1999) "Engineering endoglucanase-secreting strains of ethanologenic *Klebsiella oxytoca* P2" *J Ind. Microbiol. Biotechnol.* 22:600-607.

Zhou, S. et al. (2003) "Production of optically pure D-lactic acid in mineral salt medium by metabolically engineered *Escherichia coli* W3110 " *Appl Environ Microbiol.* 69:399-407.

Zhou, S. et al. (2003a) "Productions of optically pure D-lactic acid in mineral salt medium by metabolically engineered *Escherichia coli* D-(−)-lactate dehydrogenase gene (ldhA) with the L-(+)-lactate dehydrogenase gene (ldhL) from *Pediococcus acidilactici*" *Appl. Environ. Microbiol.* 69:2237-2244.

Zhou, S., Yomano, L. P., Shanmugam, K. T., Ingram, L. O. (2005) "Fermentation of 10% (w/v) sugar to D-(−)-lactate by engineered *Escherichia coli* B" *Biotechnol. Lett.* 27:1891-1896.

Zhou, S., Shanmugam, K. T., Yomano, L. P., Grabar, T. B., Ingram, L. O. (2006) "Fermentation of 12% (w/v) glucose to 1.2 M lactate by *Escherichia coli* B strain SZ194 using mineral salts medium" *Biotechnol. Lett.* In Press.

Zhu, J. and Shimizu, K. (2004) "The effect of pfl gene knockout on the metabolism for optically pure D-lactate production by *Escherichia coli*" *Appl Microbiol and Biotechnol.* 64:367-375.

---

We claim:

1. A genetically modified *E. coli* strain comprising the following modifications:
   i) inactivation or deletion of an acetate kinase gene;
   ii) inactivation or deletion of a fumarate reductase gene;
   iii) inactivation or deletion of a pyruvate formatelyase gene;
   iv) inactivation or deletion of an alcohol dehydrogenase gene;
   v) inactivation or deletion of a methylglyoxal synthase gene; and
   vi) insertion of a heterologous L-(+) lactate dehydrogenase (ldhL) gene.

2. The genetically modified *E. coli* stain according to claim 1, wherein said heterologous L-(+) lactate dehydrogenase gene replaces the native ldhA gene encoding a D-(−) lactate dehydrogenase.

3. The genetically modified *E. coli* strain according to claim 1, wherein said heterologous L-(+) lactate dehydrogenase gene is derived from *Pediococcus Acidilactici*.

4. The genetically modified *E. coli* strain according to claim 1, wherein said *E. coli* strain is selected from a group consisting of TG105, TG106, TG107 and TG108.

5. A method of producing lactate or lactic acid comprising culturing the genetically modified *E. coli* strain according to claim 1 under conditions that allow for the production of lactic acid and optionally neutralizing the lactic acid to form lactate.

6. The method according to claim 5, wherein said method produces L-(+)-lactate or L-(+)-lactic acid with a chiral purity of at least 99.9%.

7. The method according to claim 5, wherein lactate or lactic acid is produced at concentrations of at least 0.5M.

8. A composition comprising culture medium and a genetically modified *E. coli* strain according to claim 1.

* * * * *

UNITED STATES PATENT AND TRADEMARK OFFICE
CERTIFICATE OF CORRECTION

PATENT NO. : 8,426,191 B2  
APPLICATION NO. : 12/632041  
DATED : April 23, 2013  
INVENTOR(S) : Shengde Zhou et al.

Page 1 of 3

It is certified that error appears in the above-identified patent and that said Letters Patent is hereby corrected as shown below:

In the Specification

Column 28,  
Line 8, "in the lacy," should read --in the *lacY*,--.  
Line 20, "lacZ, lacy," should read --*lacZ'*, *lacY*,--.

Column 39,  
Table 12, Column Partial Sequence, Row TG114 *frdABC*,  
"GCCAATAACAAGGAGAAGGCGAATGGATCTGATAGATTGTTTTTAAAAAATTGTTTTT GGCTCTCGACAATTTCCAACAACATCCCTATATTTATCCCATCTAAAAGGCCTCTACCT TGAAAAGGCGAGGCTACCTGCTTGTTTTTCGGGACAGGATCCTCTAGAGTCAACCTGCT TGTTACTCGTGATCCCATTCACAAGGGCGAATTAATTCCCCCTTCTGTTCCGTTACCAA CACTGAGCCGGACAGTAATGGGAAAGCCAAGTGTAGGCTGGAGCTGCTTCGAAGTTCCT *ATACTTTCTAGAGAATAGGAACTTCGGAATAGGAACTAAGGAGGATATTCATATG*GTGG TTGCCACCATCGTAATCCTGTT[b] (SEQ ID NO: 37)"

should read

--GCCAATAAGAAGGAGAAGGCGAATGGATCTGATAGATTGTTTTTAAAAAATTGTTTTT GGCTCTCGACAATTTCCAACAACATCCCTATATTTATCCCATCTAAAAGGCCTCTACCT TGAAAAGGCGAGGCTACCTGCTTGTTTTTCGGGACAGGATCCTCTAGAGTCAACCTGCT TGTTACTCGTGATCCCATTCACAAGGGCGAATTAATTCGCCCTTCTGTTCCGTTACCAA CACTGAGCCGGACAGTAATGGGAAAGCCAAGTGTAGGCTGGAGCTGCTTCGAAGTTCCT *ATACTTTCTAGAGAATAGGAACTTCGGAATAGGAACTAAGGAGGATATTCATATG*GTGG TTGCCACCATCGTAATCCTGTT[b] (SEQ ID NO: 37)--.

Signed and Sealed this  
Nineteenth Day of November, 2013

Teresa Stanek Rea  
*Deputy Director of the United States Patent and Trademark Office*

CERTIFICATE OF CORRECTION (continued)
U.S. Pat. No. 8,426,191 B2

Column 39,
Table 12, Column Partial Sequence, Row TG114ackA,
"**CTCACAGCGAAGCGCTCAACTTTATCGTTAATACTATTCTGGCACAAAAACCAGAACTG
TCTGCGCAGCTGACTGCTATCGGTCACCGTATCGTACACGGCGGCGAAAAGTATACCAG
CTCCGTAGTGATCGATGAGTCTGTTATTCAGGGTATCAAAGATGCAGCTTCTTTTGCAC
CGC**TGCACAACCCGGCTCACCTGATCGGTATCGAAGAAGCTCTGAAATCTTTCCCACAG
CTGA**AAGACAAAAACGTTGCTGTATTTGACACCGCGTTCCACCAGACTATGCCGGAAGA
GTCTT**ACCTCTACGCCCTGCCTTACAACCTGTACAAAGAGCACGGCATCCGTCGTTACG
GCGCG**CACGGCACCAGCCACTTCTATGTAACCCAGGAAGCGGCAAAAATGCTGAACAAA
CCGGTAGAAGAACTGAACATCATCACCTGCCACCTGGGCAACGGTGGTTCCGTTTCTGC
TATCCGCA**ACGGTAAATGCGTTGACACCTCTATGGGCCTGACCCCGCTGGAAGGTCTGG
TCATGGGTACCCCTTCTGGTGAT*GGGGAGCTTGTCGACAATTCGAAGTTCCTATACTTT
CTAGAGAATAGGAACTTCGGATCAATTCATCGGGCGCGGGAATTCGAGCTCGGTACCC****A
TCGATCCGGCGATCATCTTCCACCTGCACGACACCCTGGGCATGAGCGTTGACGCAATC
AACAAACTGCTGACCAAAGAGTCTGGCCTGCTGGGTCTGACCGAAGTGACCAGCGACTG
CCGCTATGTTGAAGACAACTACGCGACGAAAGAAGACGCGAAGCGCGCAATGGACGTTT
ACTGCCACCGCCTG**GCGAAATACATCGGTCCCTACACTGCGCTGATGGATGGTCGTCTG
GACGCTGTTGTATTC (SEQ ID NO: 39)"

should read

--**CTCACAGCGAAGCGCTCAACTTTATCGTTAATACTATTCTGGCACAAAAACCAGAACT
GTCTGCGCAGCTGACTGCTATCGGTCACCGTATCGTACACGGCGGCGAAAAGTATACCA
GCTCCGTAGTGATCGATGAGTCTGTTATTCAGGGTATCAAAGATGCAGCTTCTTTTGCA
CCGC**TGCACAACCCGGCTCACCTGATCGGTATCGAAGAAGCTCTGAAATCTTTCCCACA
GCTGA**AAGACAAAAACGTTGCTGTATTTGACACCGCGTTCCACCAGACTATGCCGGAAG
AGTCTT**ACCTCTACGCCCTGCCTTACAACCTGTACAAAGAGCACGGCATCCGTCGTTAC
GGCGCG**CACGGCACCAGCCACTTCTATGTAACCCAGGAAGCGGCAAAAATGCTGAACAA
ACCGGTAGAAGAACTGAACATCATCACCTGCCACCTGGGCAACGGTGGTTCCGTTTCTG
CTATCCGCA**ACGGTAAATGCGTTGACACCTCTATGGGCCTGACCCCGCTGGAAGGTCTG
GTCATGGGTACCCGTTCTGGTGAT*GGGGAGCTTGTCGACAATTCGAAGTTCCTATACTT
TCTAGAGAATAGGAACTTCGGATCAATTCATCGGGCGCGGGAATTCGAGCTCGGTACCC***
**ATCGATCCGGCGATCATCTTCCACCTGCACGACACCCTGGGCATGAGCGTTGACGCAAT
CAACAAACTGCTGACCAAAGAGTCTGGCCTGCTGGGTCTGACCGAAGTGACCAGCGACT
GCCGCTATGTTGAAGACAACTACGCGACGAAAGAAGACGCGAAGCGCGCAATGGACGTT
TACTGCCACCGCCTG**GCGAAATACATCGGTGCCTACACTGCGCTGATGGATGGTCGTCT
GGACGCTGTTGTATTC (SEQ IDNO: 39)--.

CERTIFICATE OF CORRECTION (continued)
U.S. Pat. No. 8,426,191 B2

Column 39,
Table 12, Column Partial Sequence, Row TG114 focA-pflB,
"ATAGCCTACGCAATGTAGGCTTAATGATTAGTCTGAGTTATATTACGGGGCGTTTTTT
TAATGCCCCGCTTTACATATATTTGCATTAATAAAATAATTGTAATTATAAGGTTAAAT
ATCGGTAATTTGTATTTAATAAATACGATCGATATTGTTACTTTATTCGCCTGATGCTC
CCTTTTAATTAACTGTTTTAGCGGAGGATGCGGAAAAAATTCAACTCATTTGTTAATTT
TTAAAATTTATTTTTATTTGGATAATCAAATATTTACTCCGTATTTCCATAAAAACCAT
GCCAGTTACGGGCCTA**TAAGTGTAGGCTGGAGCTGCTTCGAAGTTCCTATACTTTCTAG
AAATAGGAACTTCGGAATAGGAACTAAGGAGGATATTCATATGAGAACAGCAGCAGGAC
GTTAT** (SEQ ID NO:43)"

should read

--ATAGCCTACGCAATGTAGGCTTAATGATTAGTCTGAGTTATATTACGGGGCGTTTTTT
TAATGCCCCGCTTTACATATATTTGCATTAATAAAATAATTGTAATTATAAGGTTAAAT
ATCGGTAATTTGTATTTAATAAATACGATCGATATTGTTACTTTATTCGCCTGATGCTC
CCTTTTAATTAACTGTTTTAGCGGAGGATGCGGAAAAAATTCAACTCATTTGTTAATTT
TTAAAATTTATTTTTATTTGGATAATCAAATATTTACTCCGTATTTGCATAAAAACCAT
GCGAGTTACGGGCCTA**TAAGTGTAGGCTGGAGCTGCTTCGAAGTTCCTATACTTTCTAG
AGAATAGGAACTTCGGAATAGGAACTAAGGAGGATATTCATATGAGAACAGCAGCAGGA
CGTTAT** (SEQ ID NO:43)--.

Column 39,
Line 64, "de_eted" should read --deleted--.

Column 62,
Line 10, "*Acidilactici.*" should read --*acidilactici.*--.

SEQUENCE LISTING

```
<160> NUMBER OF SEQ ID NOS: 46

<210> SEQ ID NO 1
<211> LENGTH: 65
<212> TYPE: DNA
<213> ORGANISM: Artificial Sequence
<220> FEATURE:
<223> OTHER INFORMATION: sense primer for frdBC deletion

<400> SEQUENCE: 1
atggctgaga tgaaaaacct gaaaattgag gtggtgcgct ataacgtgta ggctggagct      60
gcttc                                                                 65

<210> SEQ ID NO 2
<211> LENGTH: 65
<212> TYPE: DNA
<213> ORGANISM: Artificial Sequence
<220> FEATURE:
<223> OTHER INFORMATION: antisense primer for frdBC deletion

<400> SEQUENCE: 2
```

```
ttaccagtac agggcaacaa acaggattac gatggtggca accaccatat gaatatcctc      60
cttag                                                                  65

<210> SEQ ID NO 3
<211> LENGTH: 65
<212> TYPE: DNA
<213> ORGANISM: Artificial Sequence
<220> FEATURE:
<223> OTHER INFORMATION: sense primer for adhE deletion

<400> SEQUENCE: 3
atggctgtta ctaatgtcgc tgaacttaac gcactcgtag agcgtgtgta ggctggagct      60
gcttc                                                                  65

<210> SEQ ID NO 4
<211> LENGTH: 65
<212> TYPE: DNA
<213> ORGANISM: Artificial Sequence
<220> FEATURE:
<223> OTHER INFORMATION: antisense primer for adhE deletion

<400> SEQUENCE: 4
ttaagcggat tttttcgctt ttttctcagc tttagccgga gcagccatat gaatatcctc      60
cttag                                                                  65

<210> SEQ ID NO 5
<211> LENGTH: 65
<212> TYPE: DNA
<213> ORGANISM: Artificial Sequence
<220> FEATURE:
<223> OTHER INFORMATION: sense primer for celY deletion

<400> SEQUENCE: 5
gataaggcgg aagcagccaa taagaaggag aaggcgaatg gctgagtgta ggctggagct      60
gcttc                                                                  65

<210> SEQ ID NO 6
<211> LENGTH: 65
<212> TYPE: DNA
<213> ORGANISM: Artificial Sequence
<220> FEATURE:
<223> OTHER INFORMATION: antisense primer for celY deletion

<400> SEQUENCE: 6
ccagaatacc ggttcgtcag aacgctttgg atttggatta atcatcatat gaatatcctc      60
cttag                                                                  65

<210> SEQ ID NO 7
<211> LENGTH: 70
<212> TYPE: DNA
<213> ORGANISM: Artificial Sequence
<220> FEATURE:
<223> OTHER INFORMATION: sense primer for mgsA deletion

<400> SEQUENCE: 7
atgtacatta tggaactgac gactcgcact ttacctgcgc ggaaacatat gtgtaggctg      60
gagctgcttc                                                             70

<210> SEQ ID NO 8
<211> LENGTH: 70
<212> TYPE: DNA
<213> ORGANISM: Artificial Sequence
```

<220> FEATURE:
<223> OTHER INFORMATION: antisense primer for mgsA deletion

<400> SEQUENCE: 8
ttacttcaga cggtccgcga gataacgctg ataatcgggg atcagaatat catatgaata    60
tcctccttag                                                          70

<210> SEQ ID NO 9
<211> LENGTH: 20
<212> TYPE: DNA
<213> ORGANISM: Artificial Sequence
<220> FEATURE:
<223> OTHER INFORMATION: sense primer for amplification of FRT-cat-sacB

<400> SEQUENCE: 9
tgtgctgcaa ggcgattaag                                               20

<210> SEQ ID NO 10
<211> LENGTH: 20
<212> TYPE: DNA
<213> ORGANISM: Artificial Sequence
<220> FEATURE:
<223> OTHER INFORMATION: antisense primer for amplification of
      FRT-cat-sacB

<400> SEQUENCE: 10
ttcgatcacg gcacgatcat                                               20

<210> SEQ ID NO 11
<211> LENGTH: 21
<212> TYPE: DNA
<213> ORGANISM: Artificial Sequence
<220> FEATURE:
<223> OTHER INFORMATION: sense primer for amplification of cat-sacB with
      5' NheI site

<400> SEQUENCE: 11
ttagctagca tgtgacggaa g                                             21

<210> SEQ ID NO 12
<211> LENGTH: 21
<212> TYPE: DNA
<213> ORGANISM: Artificial Sequence
<220> FEATURE:
<223> OTHER INFORMATION: antisense primer for amplification of cat-sacB
      with 5' NheI site

<400> SEQUENCE: 12
ccgctagcat caaagggaaa a                                             21

<210> SEQ ID NO 13
<211> LENGTH: 23
<212> TYPE: DNA
<213> ORGANISM: Artificial Sequence
<220> FEATURE:
<223> OTHER INFORMATION: sense primer for cloning frdABCD

<400> SEQUENCE: 13
ctggagtaca gcgacgtgaa gat                                           23

<210> SEQ ID NO 14
<211> LENGTH: 20
<212> TYPE: DNA
<213> ORGANISM: Artificial Sequence
<220> FEATURE:
<223> OTHER INFORMATION: antisense primer for cloning frdABCD

```
<400> SEQUENCE: 14
cagaacgcgc tcgtagctca                                               20

<210> SEQ ID NO 15
<211> LENGTH: 22
<212> TYPE: DNA
<213> ORGANISM: Artificial Sequence
<220> FEATURE:
<223> OTHER INFORMATION: sense primer for cloning ackA

<400> SEQUENCE: 15
gaactgcggt agttcttcac tg                                            22

<210> SEQ ID NO 16
<211> LENGTH: 20
<212> TYPE: DNA
<213> ORGANISM: Artificial Sequence
<220> FEATURE:
<223> OTHER INFORMATION: antisense primer for cloning ackA

<400> SEQUENCE: 16
gcgtcttgcg cgataaccag                                               20

<210> SEQ ID NO 17
<211> LENGTH: 20
<212> TYPE: DNA
<213> ORGANISM: Artificial Sequence
<220> FEATURE:
<223> OTHER INFORMATION: sense primer for cloning lacZ-cynX

<400> SEQUENCE: 17
gaagtgacca gcgaatacct                                               20

<210> SEQ ID NO 18
<211> LENGTH: 20
<212> TYPE: DNA
<213> ORGANISM: Artificial Sequence
<220> FEATURE:
<223> OTHER INFORMATION: antisense primer for cloning lacZ-cynX

<400> SEQUENCE: 18
ggtgatgcct tcggtgatta                                               20

<210> SEQ ID NO 19
<211> LENGTH: 20
<212> TYPE: DNA
<213> ORGANISM: Artificial Sequence
<220> FEATURE:
<223> OTHER INFORMATION: sense primer for cloning mgsA

<400> SEQUENCE: 19
gctattccac cgcagtctca                                               20

<210> SEQ ID NO 20
<211> LENGTH: 21
<212> TYPE: DNA
<213> ORGANISM: Artificial Sequence
<220> FEATURE:
<223> OTHER INFORMATION: antisense primer for cloning mgsA

<400> SEQUENCE: 20
ttatggaaga ggcgctactg c                                             21

<210> SEQ ID NO 21
<211> LENGTH: 20
<212> TYPE: DNA
```

-continued

```
<213> ORGANISM: Artificial Sequence
<220> FEATURE:
<223> OTHER INFORMATION: sense primer for cloning focA-pflB

<400> SEQUENCE: 21
agatcgccag ccgctgcaat                                              20

<210> SEQ ID NO 22
<211> LENGTH: 20
<212> TYPE: DNA
<213> ORGANISM: Artificial Sequence
<220> FEATURE:
<223> OTHER INFORMATION: antisense primer for cloning focA-pflB

<400> SEQUENCE: 22
aaccgttggt gtccagacag                                              20

<210> SEQ ID NO 23
<211> LENGTH: 20
<212> TYPE: DNA
<213> ORGANISM: Artificial Sequence
<220> FEATURE:
<223> OTHER INFORMATION: sense primer for cloning adhE

<400> SEQUENCE: 23
ccgctgtctg ataactggtc                                              20

<210> SEQ ID NO 24
<211> LENGTH: 20
<212> TYPE: DNA
<213> ORGANISM: Artificial Sequence
<220> FEATURE:
<223> OTHER INFORMATION: antisense primer for cloning adhE

<400> SEQUENCE: 24
gcataagcgg atggtcactg                                              20

<210> SEQ ID NO 25
<211> LENGTH: 20
<212> TYPE: DNA
<213> ORGANISM: Artificial Sequence
<220> FEATURE:
<223> OTHER INFORMATION: sense primer for deleting frdBC

<400> SEQUENCE: 25
gtggttgcca ccatcgtaat                                              20

<210> SEQ ID NO 26
<211> LENGTH: 20
<212> TYPE: DNA
<213> ORGANISM: Artificial Sequence
<220> FEATURE:
<223> OTHER INFORMATION: antisense primer for deleting frdBC

<400> SEQUENCE: 26
cgccttctcc ttcttattgg                                              20

<210> SEQ ID NO 27
<211> LENGTH: 22
<212> TYPE: DNA
<213> ORGANISM: Artificial Sequence
<220> FEATURE:
<223> OTHER INFORMATION: sense primer for deleting ackA

<400> SEQUENCE: 27
ctggacgctg ttgtattcac tg                                           22
```

```
<210> SEQ ID NO 28
<211> LENGTH: 20
<212> TYPE: DNA
<213> ORGANISM: Artificial Sequence
<220> FEATURE:
<223> OTHER INFORMATION: antisense primer for deleting ackA

<400> SEQUENCE: 28
gttgagcgct tcgctgtgag                                              20

<210> SEQ ID NO 29
<211> LENGTH: 21
<212> TYPE: DNA
<213> ORGANISM: Artificial Sequence
<220> FEATURE:
<223> OTHER INFORMATION: lacZ antisense with 5' NheI site

<400> SEQUENCE: 29
acgctagctc tgacaatggc a                                            21

<210> SEQ ID NO 30
<211> LENGTH: 21
<212> TYPE: DNA
<213> ORGANISM: Artificial Sequence
<220> FEATURE:
<223> OTHER INFORMATION: cynX antisense with 5' NheI site

<400> SEQUENCE: 30
acgctagcat tgccgctgat a                                            21

<210> SEQ ID NO 31
<211> LENGTH: 20
<212> TYPE: DNA
<213> ORGANISM: Artificial Sequence
<220> FEATURE:
<223> OTHER INFORMATION: sense primer for deleting mgsA

<400> SEQUENCE: 31
agcgttatct cgcggaccgt                                              20

<210> SEQ ID NO 32
<211> LENGTH: 20
<212> TYPE: DNA
<213> ORGANISM: Artificial Sequence
<220> FEATURE:
<223> OTHER INFORMATION: antisense primer for deleting mgsA

<400> SEQUENCE: 32
aagtgcgagt cgtcagttcc                                              20

<210> SEQ ID NO 33
<211> LENGTH: 20
<212> TYPE: DNA
<213> ORGANISM: Artificial Sequence
<220> FEATURE:
<223> OTHER INFORMATION: sense primer for deleting focA-pflB

<400> SEQUENCE: 33
gcagcaggac gttattactc                                              20

<210> SEQ ID NO 34
<211> LENGTH: 21
<212> TYPE: DNA
<213> ORGANISM: Artificial Sequence
<220> FEATURE:
<223> OTHER INFORMATION: antisense primer for deleting focA-pflB
```

-continued

```
<400> SEQUENCE: 34
gcctacattg cgtaggctat t                                              21

<210> SEQ ID NO 35
<211> LENGTH: 20
<212> TYPE: DNA
<213> ORGANISM: Artificial Sequence
<220> FEATURE:
<223> OTHER INFORMATION: sense primer for deleting adhE

<400> SEQUENCE: 35
gctgctccgg ctaaagctga                                                20

<210> SEQ ID NO 36
<211> LENGTH: 21
<212> TYPE: DNA
<213> ORGANISM: Artificial Sequence
<220> FEATURE:
<223> OTHER INFORMATION: antisense primer for deleting adhE

<400> SEQUENCE: 36
acgctctacg agtgcgttaa g                                              21

<210> SEQ ID NO 37
<211> LENGTH: 375
<212> TYPE: DNA
<213> ORGANISM: Escherichia coli
<220> FEATURE:
<221> NAME/KEY: misc_feature
<222> LOCATION: (1)..(375)
<223> OTHER INFORMATION: partial sequence of microorganism's genome
      prior to deletion of FRT scar

<400> SEQUENCE: 37
gccaataaga aggagaaggc gaatggatct gatagattgt ttttaaaaaa ttgttttttgg    60 ctctcgacaa tttccaacaa catccctata tttatcccat ctaaaaggcc tctaccttga   120
aaaggcgagg ctacctgctt gtttttcggg acaggatcct ctagagtcaa cctgcttgtt   180
actcgtgatc ccattcacaa gggcgaatta attcgccctt ctgttccgtt accaacactg   240
agccggacag taatgggaaa gccaagtgta ggctggagct gcttcgaagt tcctatactt   300
tctagagaat aggaacttcg gaataggaac taaggaggat attcatatgg tggttgccac   360
catcgtaatc ctgtt                                                   375

<210> SEQ ID NO 38
<211> LENGTH: 47
<212> TYPE: DNA
<213> ORGANISM: Escherichia coli
<220> FEATURE:
<221> NAME/KEY: misc_feature
<222> LOCATION: (21)..(22)
<223> OTHER INFORMATION: partial sequence of microorganism's genome
      after deletion of FRT scar; excision site between nucleotides 21
      and 22

<400> SEQUENCE: 38
gccaataaga aggagaaggc ggtggttgcc accatcgtaa tcctgtt                  47

<210> SEQ ID NO 39
<211> LENGTH: 900
<212> TYPE: DNA
<213> ORGANISM: Escherichia coli
<220> FEATURE:
<221> NAME/KEY: misc_feature
<222> LOCATION: (1)..(900)
<223> OTHER INFORMATION: partial sequence of microorganism's genome
```

-continued prior to deletion of FRT scar

<400> SEQUENCE: 39

```
ctcacagcga agcgctcaac tttatcgtta atactattct ggcacaaaaa ccagaactgt    60
ctgcgcagct gactgctatc ggtcaccgta tcgtacacgg cggcgaaaag tataccagct   120
ccgtagtgat cgatgagtct gttattcagg gtatcaaaga tgcagcttct tttgcaccgc   180
tgcacaaccc ggctcacctg atcggtatcg aagaagctct gaaatctttc ccacagctga   240
aagacaaaaa cgttgctgta tttgacaccg cgttccacca gactatgccg aagagtctt    300
acctctacgc cctgccttac aacctgtaca aagagcacgg catccgtcgt tacggcgcgc   360
acggcaccag ccacttctat gtaacccagg aagcggcaaa aatgctgaac aaaccggtag   420
aagaactgaa catcatcacc tgccacctgg gcaacggtgg ttccgttct gctatccgca    480
acggtaaatg cgttgacacc tctatgggcc tgaccccgct ggaaggtctg gtcatgggta   540
cccgttctgg tgatggggag cttgtcgaca attcgaagtt cctatacttt ctagagaata   600
ggaacttcgg atcaattcat cgggcgcggg aattcgagct cggtacccat cgatccggcg   660
atcatcttcc acctgcacga caccctgggc atgagcgttg acgcaatcaa caaactgctg   720
accaaagagt ctggcctgct gggtctgacc gaagtgacca gcgactgccg ctatgttgaa   780
gacaactacg cgacgaaaga agacgcgaag cgcgcaatgg acgtttactg ccaccgcctg   840
gcgaaataca tcggtgccta cactgcgctg atggatggtc gtctggacgc tgttgtattc   900
```

<210> SEQ ID NO 40
<211> LENGTH: 37
<212> TYPE: DNA
<213> ORGANISM: Escherichia coli
<220> FEATURE:
<221> NAME/KEY: misc_feature
<222> LOCATION: (19)..(20)
<223> OTHER INFORMATION: partial sequence of microorganism's genome
after deletion of FRT scar; excision site between nucleotides 19
and 20

<400> SEQUENCE: 40

```
ctcacagcga agcgctcaac tggacgctgt tgtattc                             37
```

<210> SEQ ID NO 41
<211> LENGTH: 170
<212> TYPE: DNA
<213> ORGANISM: Escherichia coli
<220> FEATURE:
<221> NAME/KEY: misc_feature
<222> LOCATION: (1)..(170)
<223> OTHER INFORMATION: partial sequence of microorganism's genome
prior to deletion of FRT scar

<400> SEQUENCE: 41

```
atggaactga cgactcgcac tttacctgcg cggaaacata tgtgtaggct ggagctgctt    60
cgaagttcct atactttcta gagaatagga acttcggaat aggaactaag gaggatattc   120
atatgatatt ctgatccccg attatcagcg ttatctcgcg gaccgtctga                170
```

<210> SEQ ID NO 42
<211> LENGTH: 46
<212> TYPE: DNA
<213> ORGANISM: Escherichia coli
<220> FEATURE:
<221> NAME/KEY: misc_feature
<222> LOCATION: (22)..(23)
<223> OTHER INFORMATION: partial sequence of microorganism's genome
after deletion of FRT scar; excision site between nucleotides 22
and 23

```
<400> SEQUENCE: 42
atggaactga cgactcgcac ttagcgttat ctcgcggacc gtctga                    46

<210> SEQ ID NO 43
<211> LENGTH: 418
<212> TYPE: DNA
<213> ORGANISM: Escherichia coli
<220> FEATURE:
<221> NAME/KEY: misc_feature
<222> LOCATION: (1)..(418)
<223> OTHER INFORMATION: partial sequence of microorganism's genome
      prior to deletion of FRT scar

<400> SEQUENCE: 43
atagcctacg caatgtaggc ttaatgatta gtctgagtta tattacgggg cgtttttta      60 atgccccgct ttacatatat ttgcattaat aaaataattg taattataag gttaaatatc   120
ggtaatttgt atttaataaa tacgatcgat attgttactt tattcgcctg atgctccctt   180
ttaattaact gttttagcgg aggatgcgga aaaaattcaa ctcatttgtt aatttttaaa   240
atttattttt atttggataa tcaaatattt actccgtatt tgcataaaaa ccatgcgagt   300
tacgggccta taagtgtagg ctggagctgc ttcgaagttc ctatactttc tagagaatag   360
gaacttcgga ataggaacta aggaggatat tcatatgaga acagcagcag gacgttat     418

<210> SEQ ID NO 44
<211> LENGTH: 35
<212> TYPE: DNA
<213> ORGANISM: Escherichia coli
<220> FEATURE:
<221> NAME/KEY: misc_feature
<222> LOCATION: (20)..(21)
<223> OTHER INFORMATION: partial sequence of microorganism's genome
      after deletion of FRT scar; excision site between nucleotides 20
      and 21

<400> SEQUENCE: 44
atagcctacg caatgtaggc gcagcaggac gttat                                35

<210> SEQ ID NO 45
<211> LENGTH: 120
<212> TYPE: DNA
<213> ORGANISM: Escherichia coli
<220> FEATURE:
<221> NAME/KEY: misc_feature
<222> LOCATION: (1)..(120)
<223> OTHER INFORMATION: partial sequence of microorganism's genome
      prior to deletion of FRT scar

<400> SEQUENCE: 45
aacgcactcg tagagcgtgt gtaggctgga gctgcttcga agttcctata ctttctagag    60
aataggaact tcggaatagg aactaaggag gatattcata tggctgctcc ggctaaagct   120

<210> SEQ ID NO 46
<211> LENGTH: 36
<212> TYPE: DNA
<213> ORGANISM: Escherichia coli
<220> FEATURE:
<221> NAME/KEY: misc_feature
<222> LOCATION: (18)..(19)
<223> OTHER INFORMATION: partial sequence of microorganism's genome
      after deletion of FRT scar; excision site between nucleotides 18
      and 19
```

```
<400> SEQUENCE: 46
aacgcactcg tagagcgtgc tgctccggct aaagct                                   36
```